US 11,944,679 B2

(12) United States Patent
Du et al.

(10) Patent No.: US 11,944,679 B2
(45) Date of Patent: Apr. 2, 2024

(54) GENOME-WIDE IDENTIFICATION OF IMMUNE EVASION FUNCTIONS IN A VIRUS

(71) Applicant: The Regents of the University of California, Oakland, CA (US)

(72) Inventors: Yushen Du, Los Angeles, CA (US); Nicholas C. Wu, Los Angeles, CA (US); Ren Sun, Pacific Palisades, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 930 days.

(21) Appl. No.: 16/493,441

(22) PCT Filed: Mar. 14, 2018

(86) PCT No.: PCT/US2018/022465
§ 371 (c)(1),
(2) Date: Sep. 12, 2019

(87) PCT Pub. No.: WO2018/170147
PCT Pub. Date: Sep. 20, 2018

(65) Prior Publication Data
US 2020/0129612 A1  Apr. 30, 2020

Related U.S. Application Data

(60) Provisional application No. 62/471,269, filed on Mar. 14, 2017.

(51) Int. Cl.
*A61K 39/145* (2006.01)
*C07K 14/005* (2006.01)
*C12N 7/00* (2006.01)
*C12N 15/10* (2006.01)

(52) U.S. Cl.
CPC .......... *A61K 39/145* (2013.01); *C07K 14/005* (2013.01); *C12N 7/00* (2013.01); *C12N 15/1058* (2013.01); *C12N 15/1072* (2013.01); *C12N 2760/16121* (2013.01); *C12N 2760/16134* (2013.01); *C12N 2760/16162* (2013.01)

(58) Field of Classification Search
None
See application file for complete search history.

(56) References Cited

U.S. PATENT DOCUMENTS

| | | |
|---|---|---|
| 5,504,005 A | 4/1996 | Bloom et al. |
| 6,669,943 B1 | 12/2003 | Palese et al. |
| 6,699,476 B1 | 3/2004 | Collins et al. |
| 9,387,240 B2 | 7/2016 | Palese et al. |
| 2005/0080034 A1 | 4/2005 | Standring et al. |
| 2005/0260601 A1 | 11/2005 | Whitt et al. |
| 2006/0140975 A1 | 6/2006 | Curtiss et al. |
| 2009/0010962 A1 | 1/2009 | Palese et al. |
| 2011/0070254 A1 | 3/2011 | Brown et al. |
| 2012/0122185 A1 | 5/2012 | Palese et al. |
| 2012/0331576 A1 | 12/2012 | Brass et al. |

FOREIGN PATENT DOCUMENTS

| | | |
|---|---|---|
| CN | 102089423 A | 6/2011 |
| TW | 201736597 A | 10/2017 |
| TW | 201738241 A | 11/2017 |
| WO | 2015157189 | 10/2015 |
| WO | 2015157189 A1 | 10/2015 |
| WO | 2018026547 A1 | 2/2018 |

OTHER PUBLICATIONS

Maamary et al., Attenuated Influenza Virus Construct with Enhanced Hemagglutinin Protein Expression, 2012, Journal of Virology, vol. 86, No. 10, pp. 5782-5790.*
PCT International Search Report & Written Opinion dated Jul. 26, 2018, PCT/US18/22465.
Donelan et al. "A recombinant influenza A virus expressing an RNA-binding-defective NS1 protein induces high levels of beta interferon and is attenuated in mice", J Virol, Dec. 2003, vol. 77, No. 24, pp. 13257-13266.
Talon et al. "Influenza A and B viruses expressing altered NS1 proteins: A vaccine approach", Proc Nat Acad Sci. Apr. 11, 2000, vol. 97, No. 8, pp. 4309-4314.
Wu et al. "High-throughput identification of loss-of-function mutations for anti-interferon activity in the influenza A virus NS segment" J Virol. Sep. 1, 2014, vol. 88, No. 17, pp. 10157-10164.
Extended European Search Report dated Jan. 14, 2021 for European Patent Application No. 18767754.7.
Chinese Office Action dated Nov. 1, 2022 for Chinese Application No. 201880030897.9.
Donelan et al., "A Recombinant Influenza A Virus Expressing an RNA-Binding-Defective NSI Protein Induces High Levels of Beta Interferon and Is Attenuated in Mice". Journal of Virology, Dec. 2003, p. 13257-13266.
Wu et al., "High-Throughput Identification of Loss-of-Function Mutations for Anti-Interferon Activity in the Influenza A Virus NS Segment". Journal of Virology, Sep. 2014 vol. 88 No. 17, p. 10157-10164.
C. Mössler et al., "Phase I/II trial of a replication-deficient trivalent influenza virus vaccine lacking NS1". Vaccine 31 , 6194-6200 (2013).

(Continued)

*Primary Examiner* — Benjamin P Blumel
(74) *Attorney, Agent, or Firm* — GATES & COOPER LLP

(57) ABSTRACT

A protocol has been developed for genetically engineering an attenuated pathogen such as the influenza virus that can grow in cells without interferons but has suppressed growth in cells with the interferons. The protocol comprises systematically identifying immune evasion functions on the pathogen's genome, then eliminating the immune evasion functions while maintaining a certain replication fitness of the pathogen. The resulting attenuated pathogen causes a strong immunologic response and can be used in a live attenuated vaccine.

9 Claims, 37 Drawing Sheets
Specification includes a Sequence Listing.

(56) References Cited

OTHER PUBLICATIONS

Du Y et al., "Genome-wide identification of interferon-sensitive mutations enables influenza vaccine design". Science 359, 290-296 (2018).

Du Y et al., Supplementary Materials for "Genome-wide identification of interferon-sensitive mutations enables influenza vaccine design ". Published Jan. 19, 2018, Science 359, 290 (2018), www.sciencemag.org/content/359/6373/290/suppl/DC1.

H. Jin et al., Multiple amino acid residues confer temperature sensitivity to human influenza virus vaccine strains (flumist) derived from cold-adapted a/ann arbor/6/60. Virology. 306, 18-24 (2003).

K. M. Graef et al., "The PB2 Subunit of the Influenza Virus RNA Polymerase Affects Virulence by Interacting with the Mitochondrial Antiviral Signaling Protein and Inhibiting Expression of Beta Interferon". J. Virol. 84, 8433-8445 (2010).

UCLA Health: The flu vaccine could get a much-needed boost. Jan. 18, 2018, 5 pages, https://www.uclahealth.org/news/the-flu-vaccine-could-get-a-muchneeded-boost.

Vincent et al. "Live attenuated influenza vaccine provides superior protection from heterologous infection in pigs with maternal antibodies without inducing vaccine-associated enhanced respiratory disease". J Virol. Oct. 2012;86(19): 10597-605. doi: 10.1128/JVI.01439-12. Epub Jul. 18, 2012.

Blanchard et al., "Modified vaccinia virus Ankara undergoes limited replication human cells and lacks several immunomodulatory proteins: implications for use as a human vaccine". Journal of General Virology ( 1998), 79, 1159-1167.

Cidoncha et al., "An Unbiased Genetic Screen Reveals the Polygenic Nature of the Influenza Virus Anti-Interferon Response". Journal of Virology p. 4632-4646, May 2014 vol. 88 No. 9.

Chinese Office Action dated Sep. 15, 2023 for Chinese Application No. 201880030897.9.

* cited by examiner

FIG. 1A

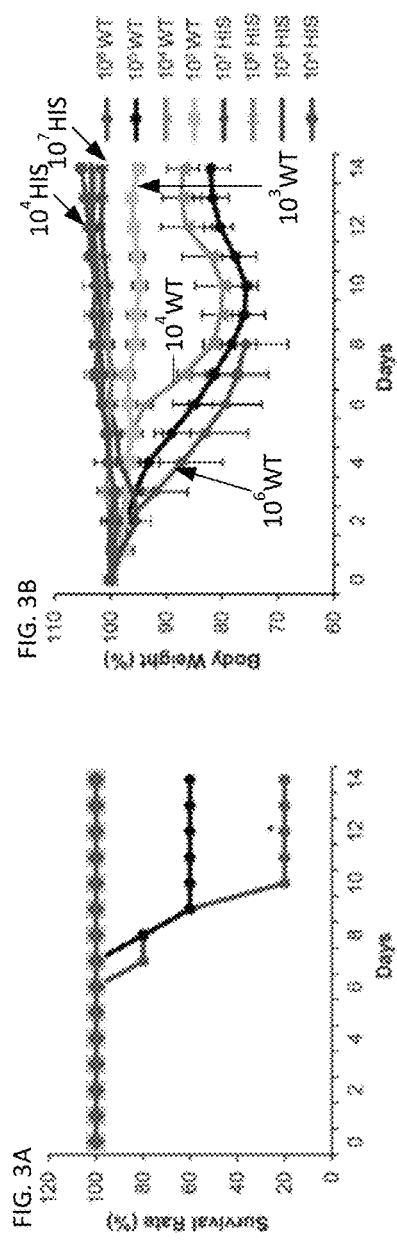
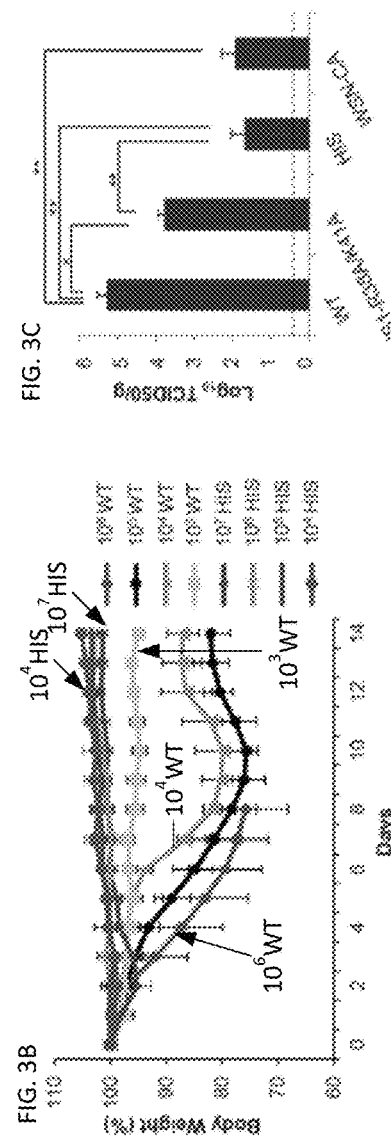
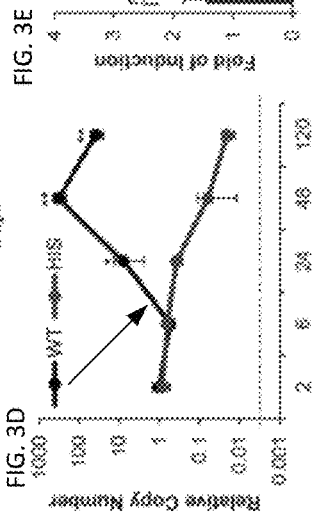
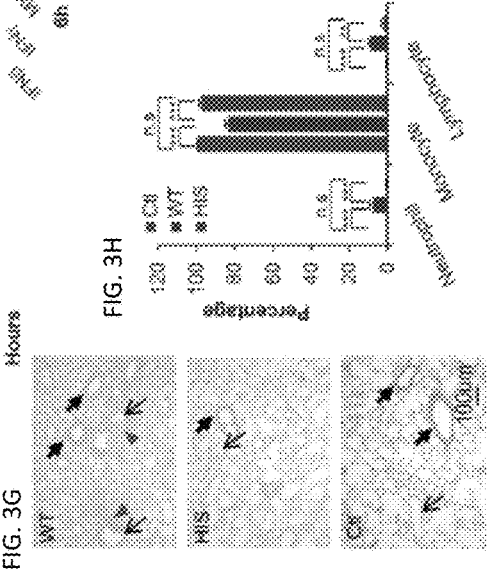
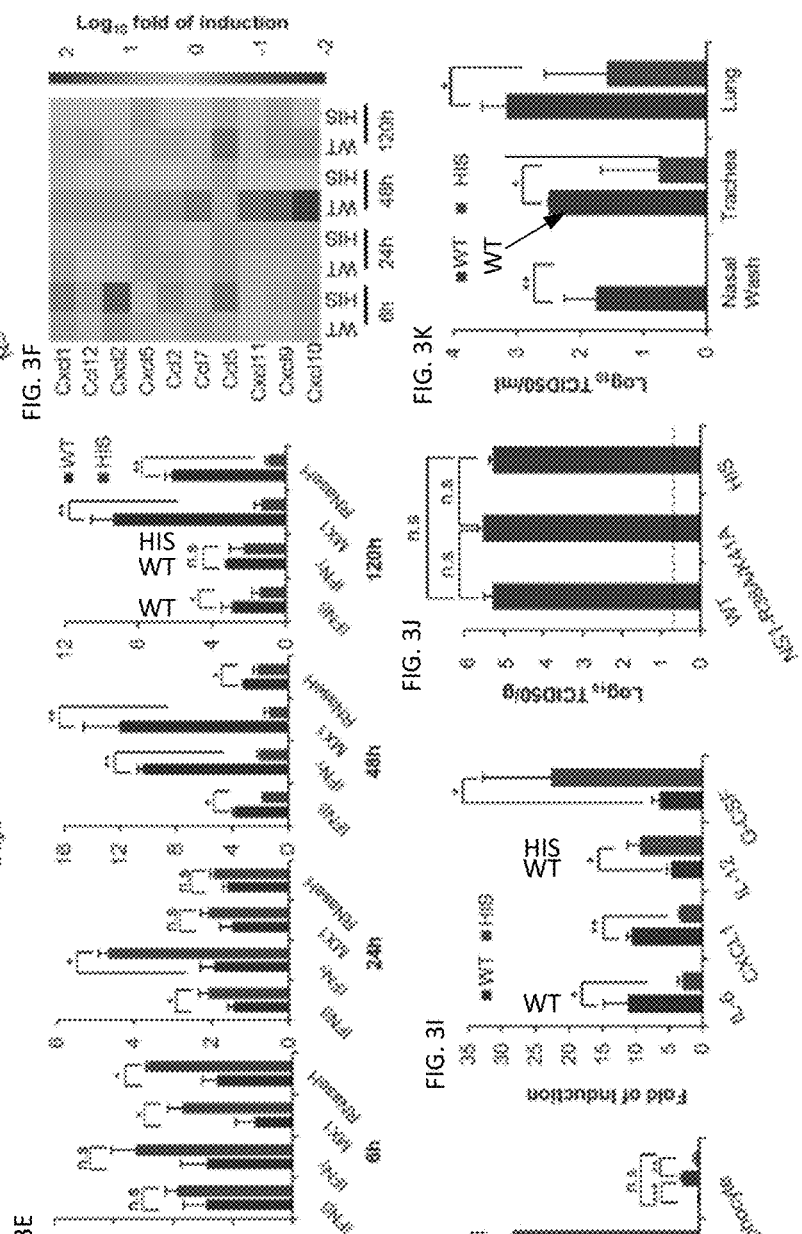
FIG. 3A
FIG. 3B
FIG. 3C
FIG. 3D
FIG. 3E
FIG. 3F
FIG. 3G
FIG. 3H
FIG. 3I
FIG. 3J
FIG. 3K

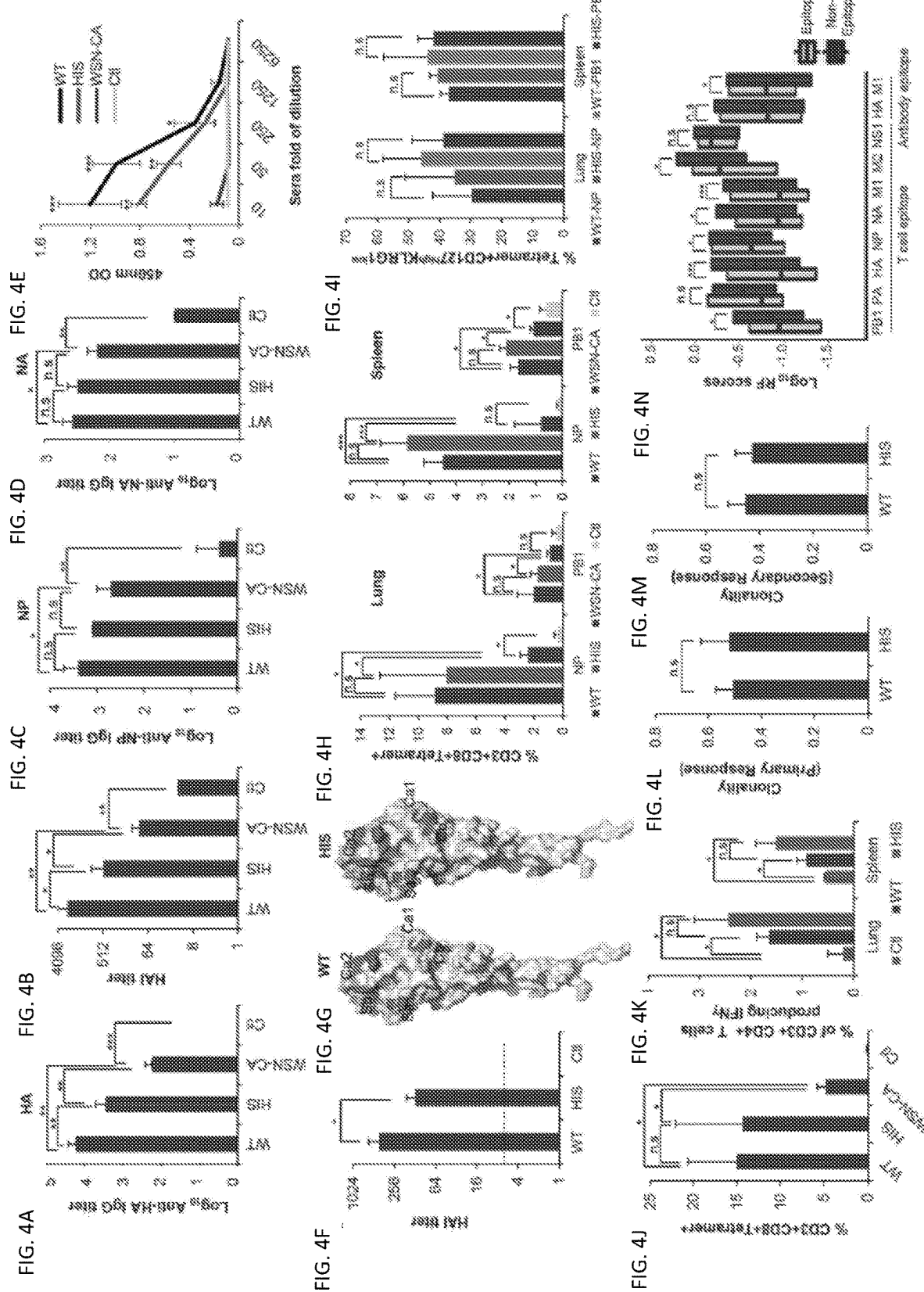

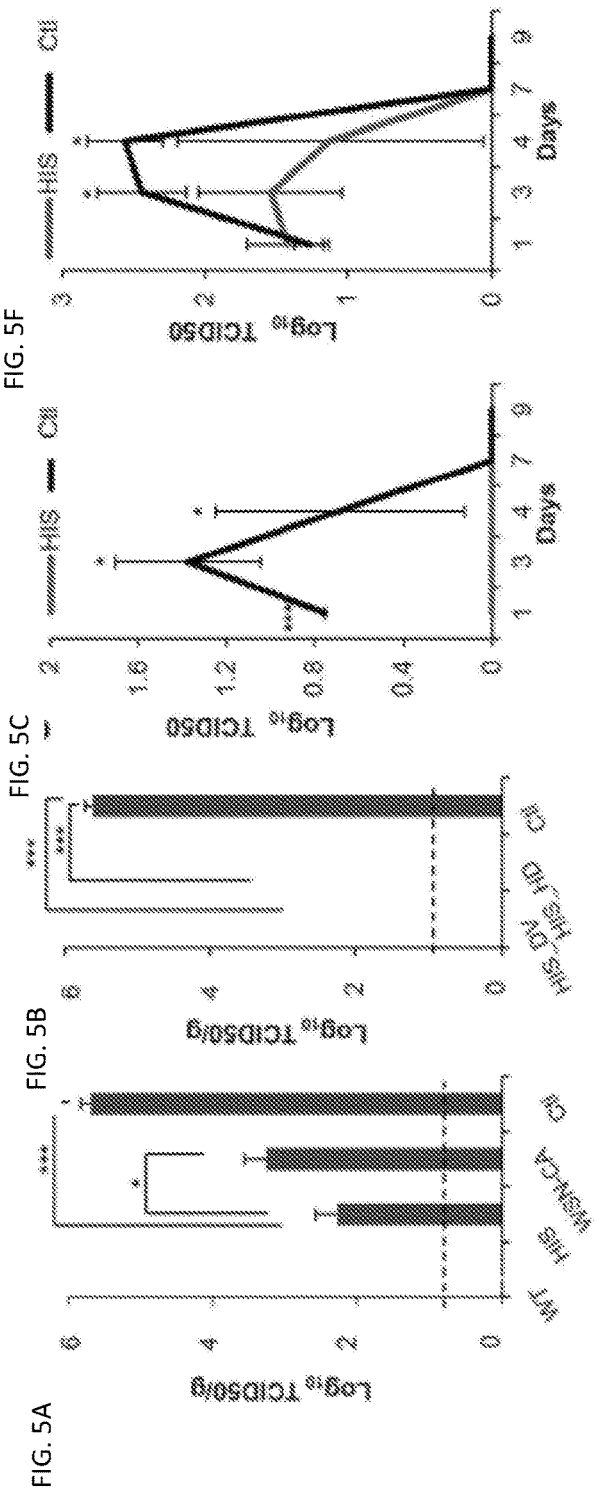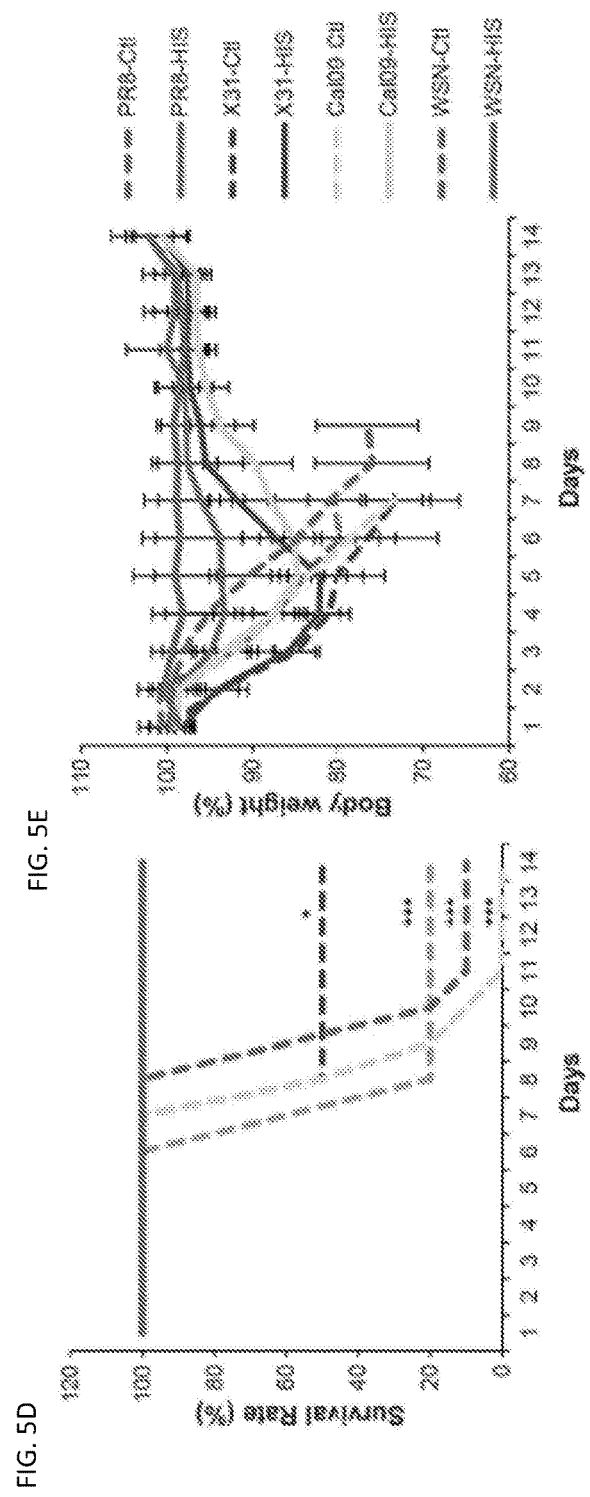

FIG. 6

FIG. 9A
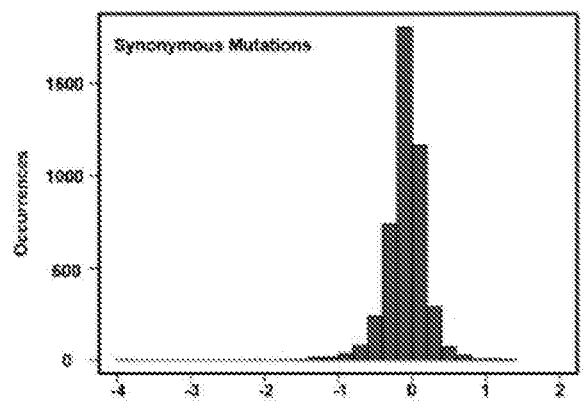
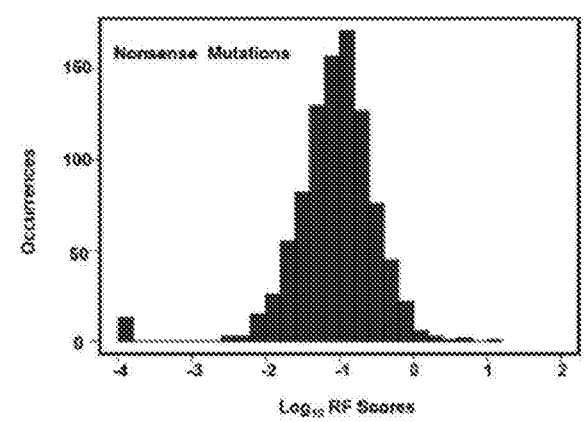
FIG. 9B
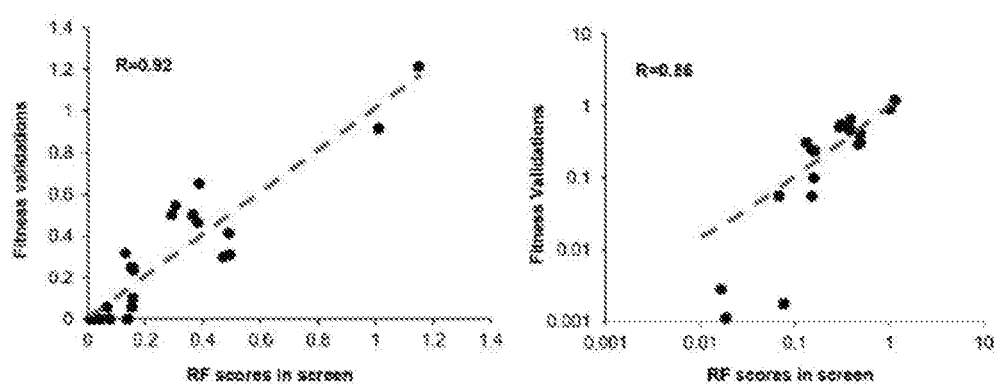

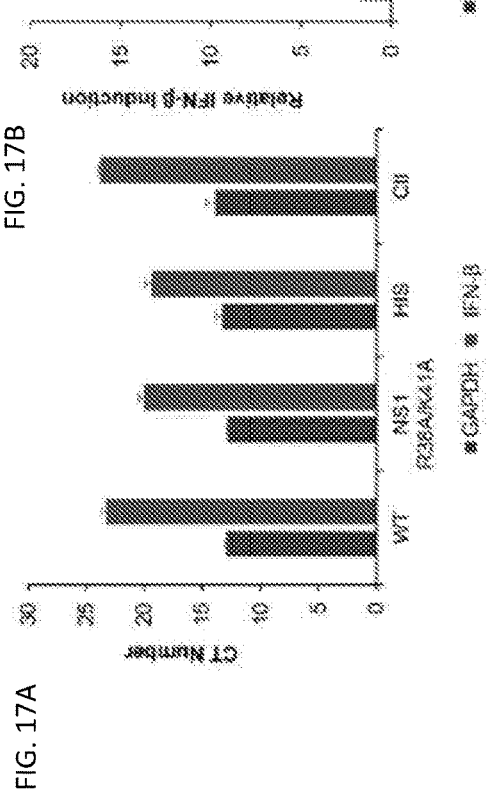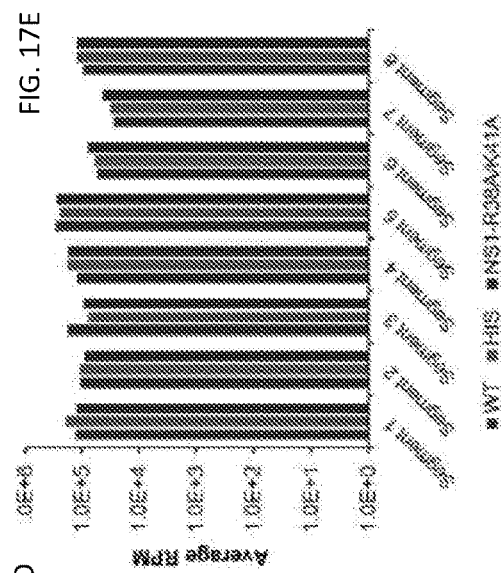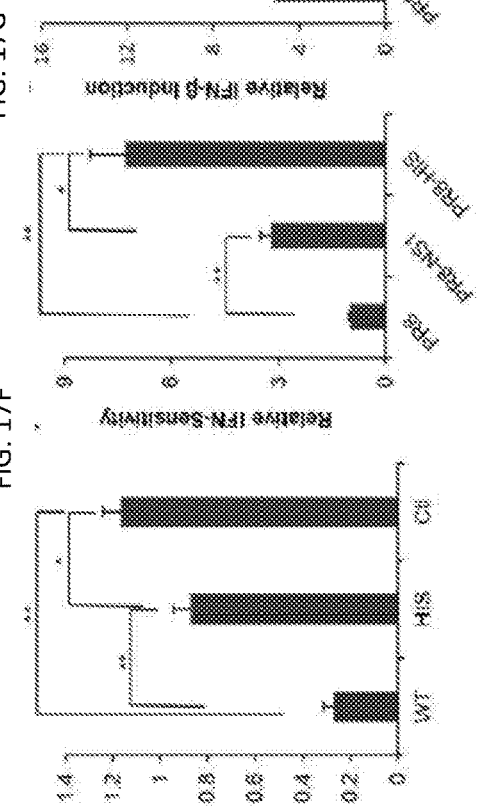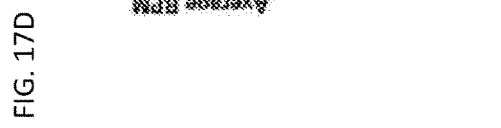
FIG. 17A FIG. 17B FIG. 17C FIG. 17D FIG. 17E FIG. 17F FIG. 17G

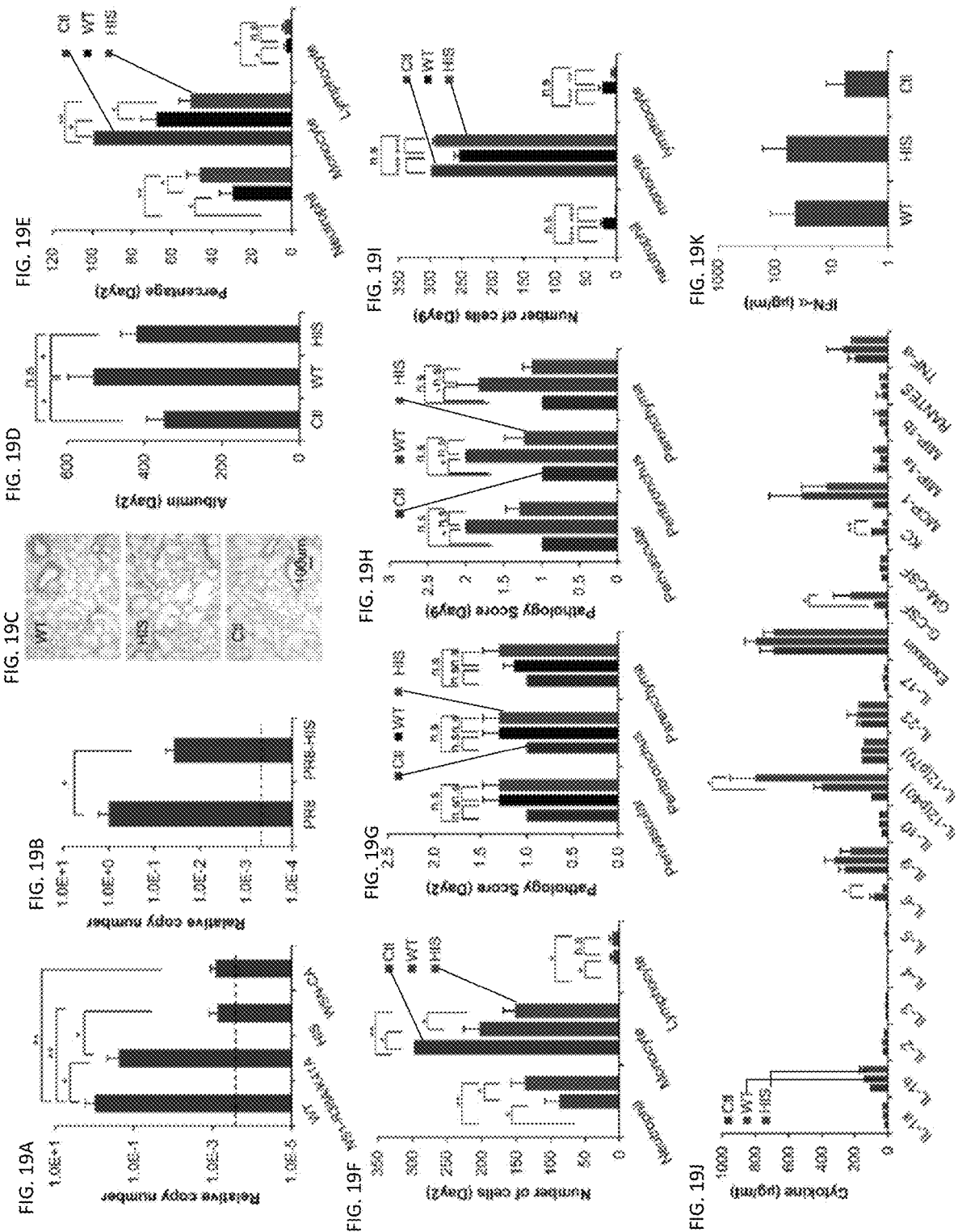

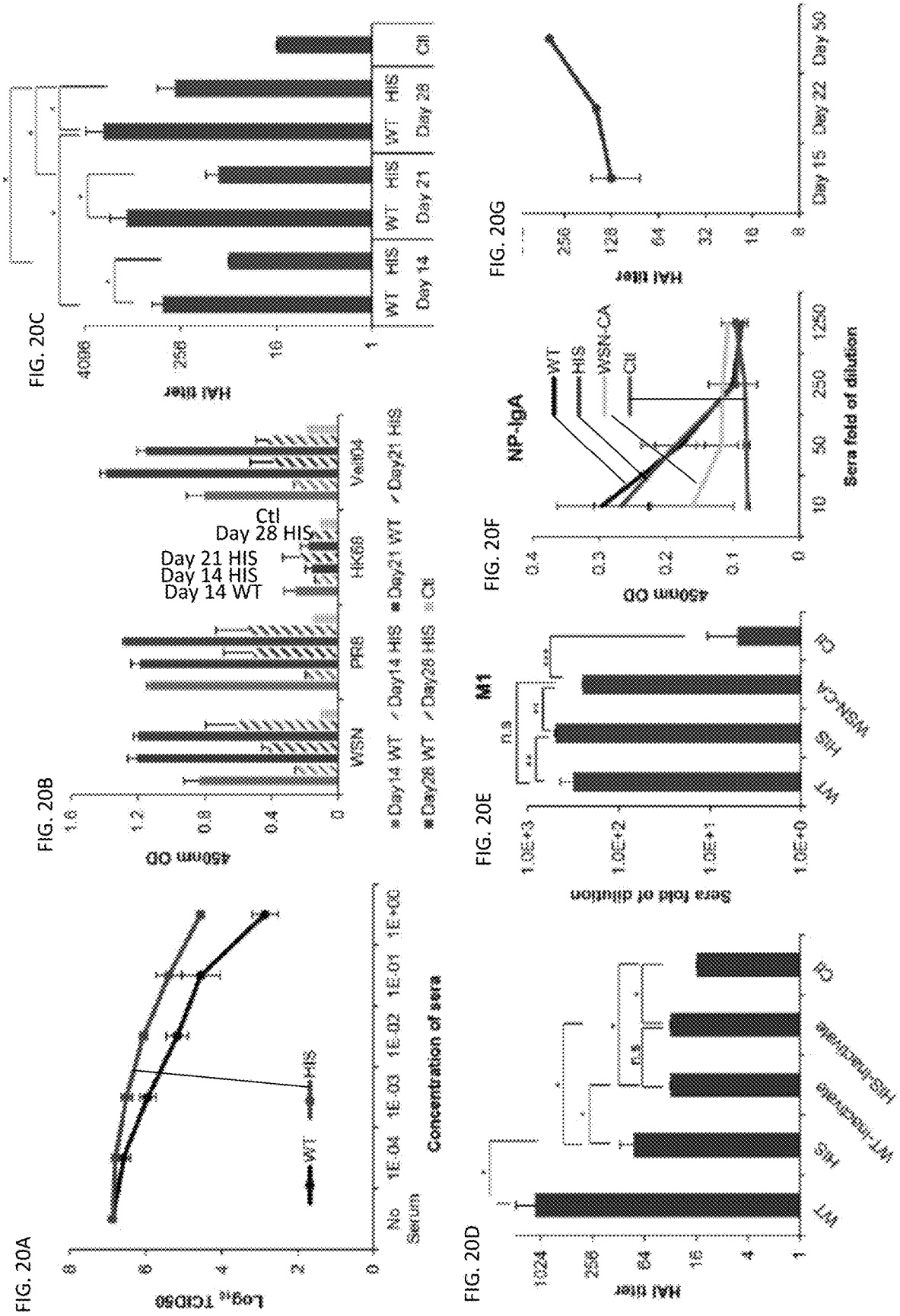

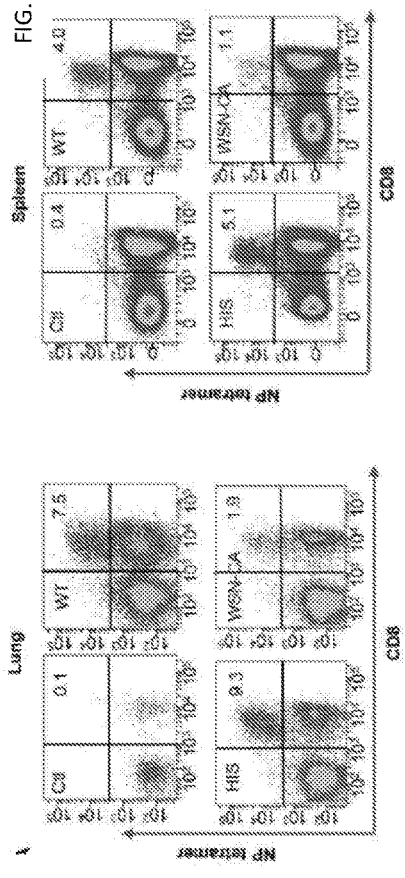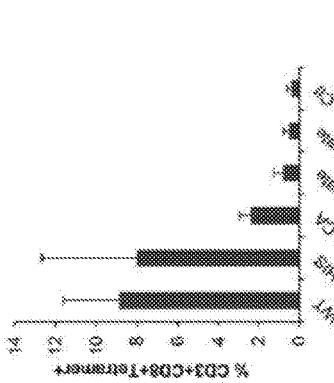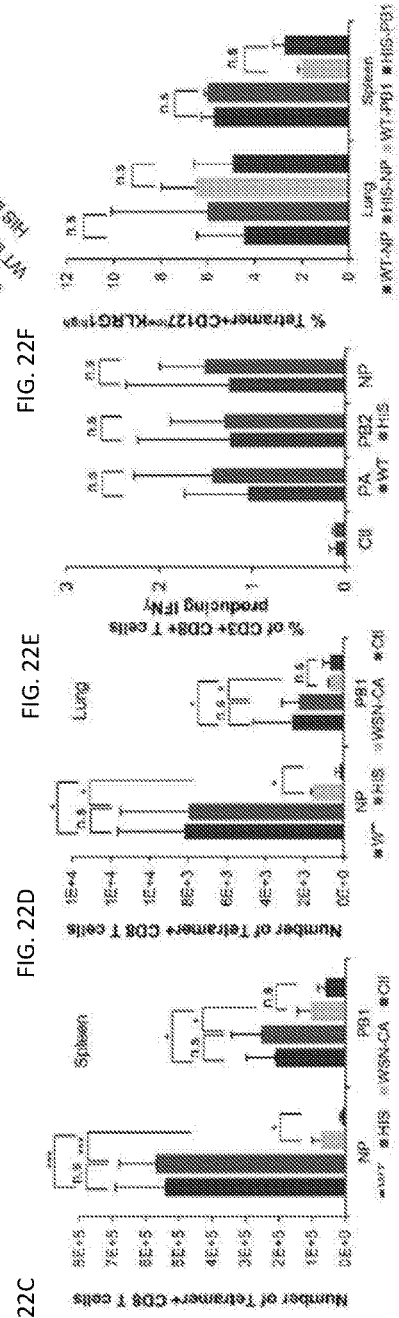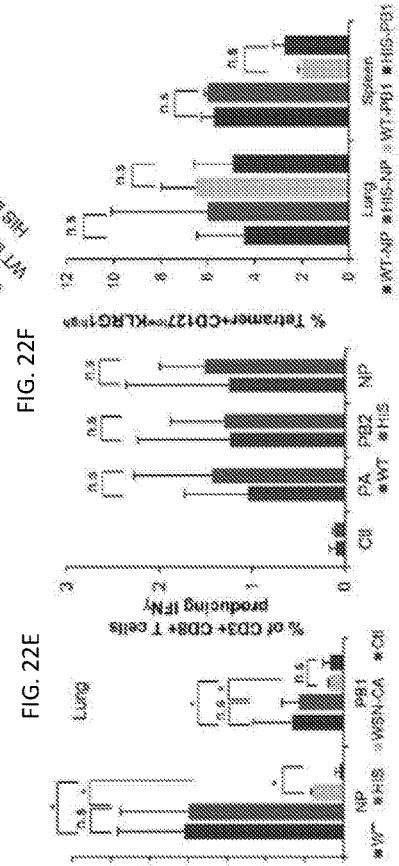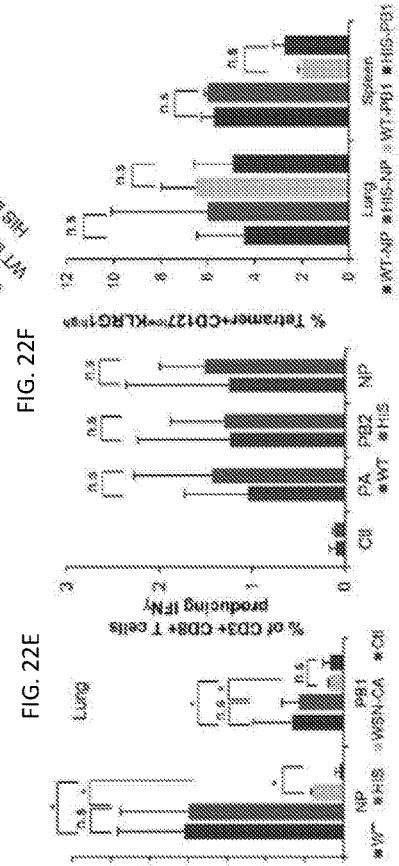
FIG. 22A
FIG. 22B
FIG. 22C
FIG. 22D
FIG. 22E
FIG. 22F
FIG. 22G
FIG. 22H
FIG. 22I

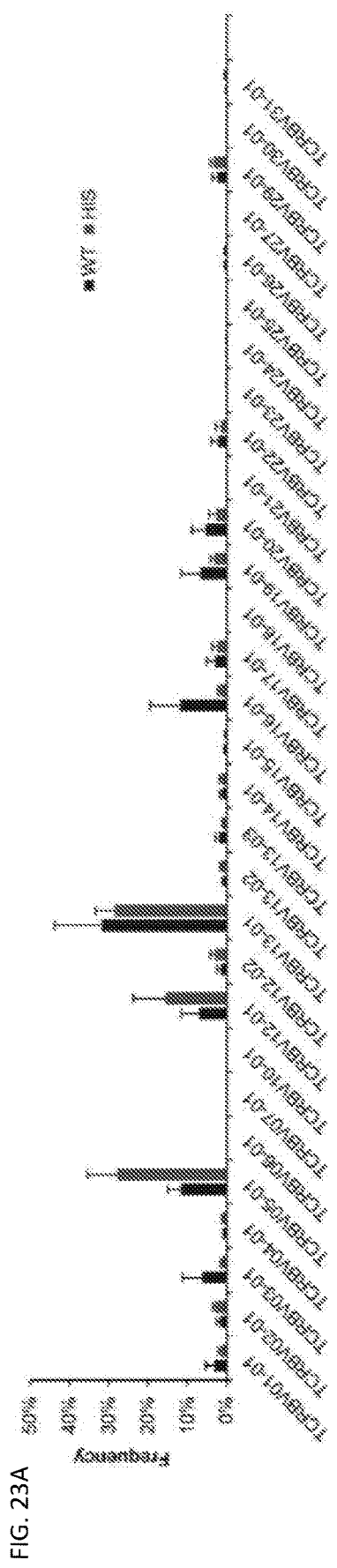
FIG. 23A
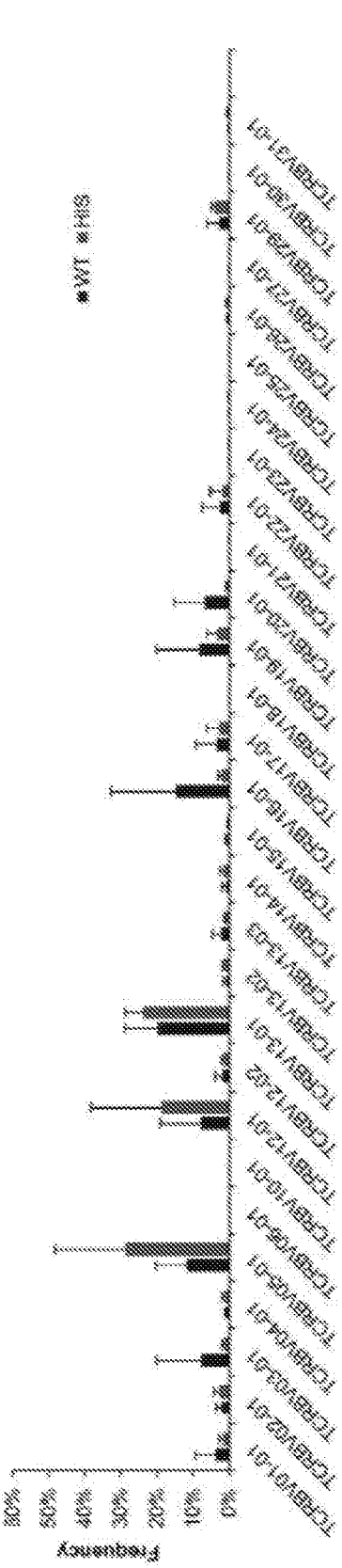
FIG. 23B
FIG. 23C
FIG. 23D

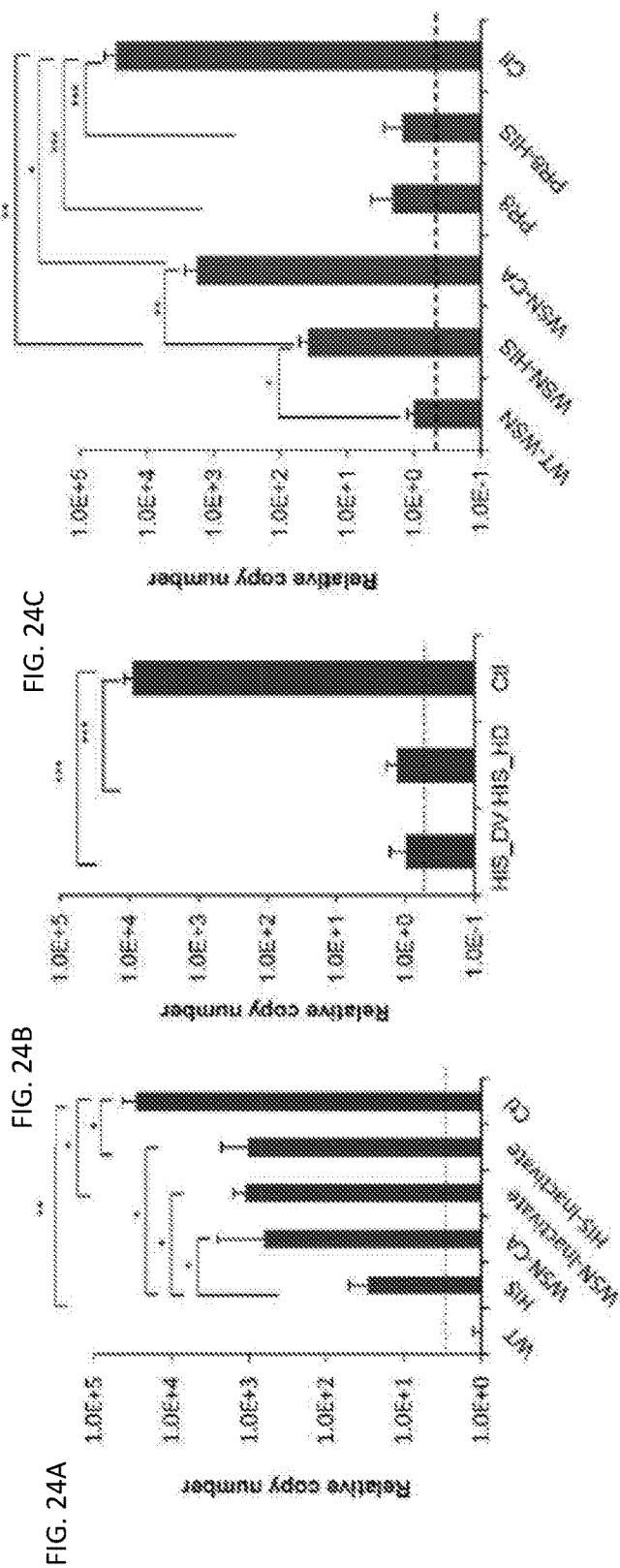
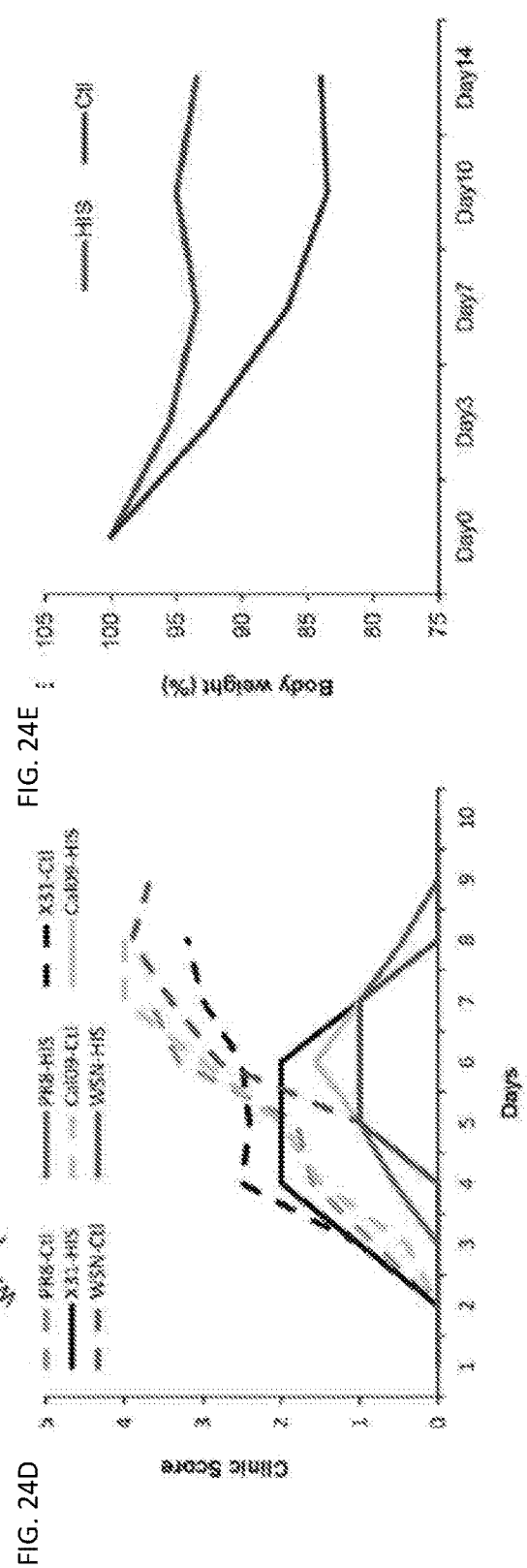
FIG. 24A
FIG. 24B
FIG. 24C
FIG. 24D
FIG. 24E

SEQUENCE LISTING

<160> NUMBER OF SEQ ID NOS: 14

<210> SEQ ID NO 1
<211> LENGTH: 13300
<212> TYPE: DNA
<213> ORGANISM: Influenza A virus WSN

<400> SEQUENCE: 1
tcaattatat tcaatatgga aagaataaaa gaactaagga atctaatgtc gcagtctcgc      60
actcgcgaga tactcacaaa aaccaccgtg gaccatatgg ccataatcaa gaagtacaca     120
tcaggaagac aggagaagaa cccagcactt aggatgaaat ggatgatggc aatgaaatat    180

```
ccaattacag cagacaagag gataacggaa atgattcctg agagaaatga gcagggacaa    240
actttatgga gtaaaatgaa tgacgccgga tcagaccgag tgatggtatc acctctggct    300
gtgacatggt ggaataggaa tggaccagtg acaagtacag ttcattatcc aaaaatctac    360
aaaacttatt ttgaaaaagt cgaaaggtta aacatggaa cctttggccc tgtccatttt     420
agaaaccaag tcaaaatacg tcgaagagtt gacataaatc ctggtcatgc agatctcagt    480
gccaaagagg cacaggatgt aatcatgaa gttgttttcc ctaacgaagt gggagccagg     540
atactaacat cggaatcgca actaacgaca accaaagaga agaaagaaga actccagggt    600
tgcaaaattt ctcctctgat ggtggcatac atgttggaga gagaactggt ccgcaaaacg    660
agattcctcc cagtggctgg tggaacaagc agtgtgtaca ttgaagtgtt gcatttgacc    720
caaggaacat gctgggaaca gatgtacact ccaggagggg aggcgaggaa tgatgatgtt    780
gatcaaagct taattattgc tgctagaaac atagtaagaa gagccacagt atcagcagat    840
ccactagcat ctttattgga gatgtgccac agcacgcaga ttggtggaat aaggatggta    900
aacatcctta ggcagaaccc aacagaagag caagccgtgg atatttgcaa ggctgcaatg    960
ggactgagaa ttagctcatc cttcagtttt ggtggattca catttaagag aacaagcgga   1020
tcatcagtca agagagagga gaggtgctt acgggcaatc ttcagacatt gaagataaga   1080
gtgcatgagg gatatgaaga gttcacaatg gttgggagaa gagcaacagc tatactcaga   1140
aaagcaacca ggagattgat tcagctgata gtgagtggga gagacgaaca gtcgattgcc   1200
gaagcaataa ttgtggccat ggtattttca caagaggatt gtatgataaa gcagttaga    1260 ggtgacctga atttcgtcaa tagggcgaat cagcgattga atcccatgca ccaacttttg   1320
agacattttc agaaggatgc aaaggtgctc tttcaaaatt ggggaattga atccatcgac   1380
aatgtgatgg gaatgatcgg gatattgccc gacatgactc caagcaccga gatgtcaatg   1440
agaggagtga gaatcagcaa aatgggggta gatgagtatt ccagcgcgga gaagatagtg   1500
gtgagcattg accgtttttt gagagttagg gaccaacgtg gaatgtact actgtctccc    1560 gaggagatca gtgaaacaca gggaacagag aaactgacaa taacttactc atcgtcaatg   1620
atgtgggaga ttaatggtcc tgaatcagtg ttggtcaata cctatcagtg gatcatcaga   1680
aactgggaaa ctgttaaaat tcagtggtcc cagaatccta aatgctgta caataaaatg   1740 gaatttgagc catttcagtc tttagttcca aaggccgtta gaggccaata cagtgggttt    1800
gtgagaactc tgttccaaca aatgagggat gtgcttggga catttgatac cgctcagata   1860
ataaaacttc ttccccttcgc agccgctcca ccaaagcaaa gtagaacgca gttctcctca   1920
ttgactataa atgtgagggg atcaggaatg agaatacttg taagggcaa ttctccagta    1980 ttcaactaca acaagaccac taaaagactc acagttctcg gaaaggatgc tgccccttta   2040
actgaagacc cagatgaagg cacagctgga gttgagtccg cagttctgag aggattcctc    2100
attctgggca agaagacag gagatatgga ccagcattaa gcataaatga actgagcaac    2160
cttgcgaaag gagagaaggc taatgtgcta attgggcaag agacgtggt gttggtaatg   2220 aaacggaaac ggaactctag catacttact gacagccaga cagcgaccaa agaattcgg    2280 atggccatca attagtgtcg aatagttta aaaatttgaa tggatgtcaa tccgactta    2340 ctttcttaa aagtgccagc acaaaatgct ataagcacaa cttccctta tactggagac    2400 cctccttaca gccatgggac aggaacagga tacaccatgg atactgtcaa caggacacat   2460
cagtactcag aaaggggaag atggacaaca acaccgaaa ctggagcacc gcaactcaac    2520
ccgattgatg ggccactgcc agaagacaat gaaccaagtg gttatgccca aacagattgt    2580
```

```
gtattggaag caatggcctt ccttgaggaa tcccatcctg gtatctttga gacctcgtgt   2640
cttgaaacga tggaggttgt tcagcaaaca cgagtggaca agctgacaca aggccgacag   2700
acctatgact ggactctaaa taggaaccag cctgctgcaa cagcattggc caacacaata   2760
gaagtgttca gatcaaatgg cctcacggcc aatgaatctg gaaggctcat agacttcctt   2820
aaggatgtaa tggagtcaat gaacaaagaa gaaatggaga tcacaactca ttttcagaga   2880
aaaagacgag tgagagacaa tatgactaag aaaatggtga cacagagaac aataggtaaa   2940
aggaagcaga gattgaacaa aaggagttat ctaattaggg cattaaccct gaacacaatg   3000
accaaagatg ctgagagagg gaagctaaaa cggagagcaa ttgcaacccc agggatgcaa   3060 ataaggggt tgtatactt tgttgagaca ctagcaagga gtatatgtga gaaacttgaa    3120
caatcaggat tgccagttgg aggcaatgag aagaaagcaa agttggcaaa tgttgtaagg   3180
aagatgatga ccaattctca ggacactgaa atttctttca ccatcactgg agataacacc   3240
aaatggaacg aaaatcagaa ccctcggatg tttttggcca tgatcacata taaccaga    3300 aatcagcccg aatggttcag aaatgttcta agtattgctc aataatgtt ctcaaacaaa    3360 atggcgagac tgggaaaggg gtacatgttt gagagcaaga gtatgaaaat tagaactcaa   3420
atacctgcag aaatgctagc aagcatcgat ttgaaatact tcaatgattc aactagaaag   3480
aagattgaaa aaatccggcc gctcttaata gatgggactg catcattgag ccctggaatg   3540
atgatgggca tgttcaatat gttaagtact gtattaggag tctccatcct gaatcttgga   3600
caaaagagac acaccaagac tacttactgg tgggatggtc ttcaatcttc tgatgatttt   3660
gctctgattg tgaatgcacc caatcatgaa gggattcaag ccggagtcaa caggttttat   3720
cgaacctgta gctacttgg aattaatatg agcaagaaaa agtcttacat aaacagaaca   3780
ggtacatttg aattcacaag ttttttctat cgttatgggt tgttgccaa tttcagcatg   3840 gagcttccca gctttgggt gtctgggatc aacgagtctg cggacatgag tattggagtt   3900
actgtcatca aaaacaatat gataaacaat gatcttggtc cagcaaccgc tcaaatggcc   3960
cttcagctgt tcatcaaaga ttacaggtac acgtaccgt gccatagagg tgacacacaa    4020
atacaaaccc gaagatcatt tgaaataaag aaactgtggg agcaaaccca ttccaaagct   4080
ggactgctgg tctccgacgg aggcccaaat ttatacaaca ttagaaatct ccacattcct   4140
gaagtctgct tgaaatggga attaatggat gaggattacc aggggcgttt atgcaaccca   4200
ctgaacccat tgtcaacca taaagacatt gaatcagtga caatgcagt gataatgcca    4260 gcacatggtc cagccaaaaa catggagtat gatgctgttg caacaacaca ctcctggatc   4320
cccaaaagaa atcgatccat cttgaataca agccaaagag gaatacttga agatgaacaa   4380
atgtaccaaa agtgctgcaa cttatttgaa aaattcttcc ccagcagttc atacagaaga   4440
ccagtcggga tatccagtat ggtggaggct atggtttcca gagcccgaat tgatgcacga   4500
attgatttcg aatctggaag gataaagaaa gaggagttca ctgagatcat gaagatctgt   4560
tccaccattg aagagctcag acggcaaaaa tagtgaattt agcttgtcct tcatgactga   4620
ttcaaaatgg aagattttgt gcgacaatgc ttcaatccga tgattgtcga gcttgcggaa   4680
aaggcaatga aagagtatgg agaggacctg aaaatcgaaa caaacaaatt tgcagcaata   4740
tgcactcact tggaagtgtg cttcatgtat tcagattttc acttcatcga tgagcaaggc   4800
gagtcaatag tcgtagaact tggcgatcca aatgcacttt tgaagcacag atttgaaata   4860
atcgagggaa gagatcgcac aatagcctgg acagtaataa acagtatttg caacactaca   4920
```

```
gggggctgaga aaccaaagtt tctaccagat ttgtatgatt acaagaagaa tagattcatc   4980
gaaattggag taacaaggag agaagttcac atatactatc tggaaaaggc caataaaatt   5040
aaatctgaga agacacacat ccacattttc tcattcactg gggaggaaat ggccacaaag   5100
gccgactaca ctctcgatga agaaagcagg gctaggatca aaaccaggct attcaccata   5160
agacaagaaa tggctagcag aggcctctgg gattcctttc gtcagtccga gagaggcgaa   5220
gagacaattg aagaaagatt tgaaatcaca ggaacaatgc gcaagcttgc cgaccaaagt   5280
ctcccgccaa acttctccag ccttgaaaaa tttagagcct atgtggatgg attcgaaccg   5340
aacggctaca ttgagggcaa gctttctcaa atgtccaaag aagtaaatgc tagaattgaa   5400
ccttttttga aatcaacacc acgaccactt agacttccgg atgggcctcc ctgttctcag   5460
cggtccaaat tcctgctgat ggatgcctta aaattaagca ttgaggaccc aagtcatgag   5520
ggagagggga taccgctata tgatgcaatc aaatgcatga gaacattctt tggatggaag   5580
gaacccaatg ttgttaaacc acacgaaaag ggaataaatc caaattatct tctgtcatgg   5640
aagcaagtac tggcagaact gcaggacatt gagaatgagg agaaaattcc aaggactaaa   5700
aatatgaaga aaacgagtca gttaaagtgg gcacttggtg agaacatggc accagaaaag   5760
gtagactttg acgattgtaa agatgtaggc gatttgaagc aatatgatag tgatgaacca   5820
gaattgaggt cgcttgcaag ttggattcag aatgagttca acaaggcatg tgaactgacc   5880
gattcaagct ggatagagct cgatgagatt ggagaagatg cggctccaat tgaacacatt   5940
gcaagcatga aaggaattat tttcacagca gaggtgtctc attgcagagc cacagaatac   6000
ataatgaagg gggtgtacat caatactgcc ttgcttaatg catcctgtgc agcaatggat   6060
gatttccaat taattccaat gataagcaag tgtagaacta aggagggaag gcgaaagacc   6120
aatttgtacg gtttcatcat aaaaggaaga tcccacttaa ggaatgacac cgatgtggta   6180
aactttgtga gcatggagtt ttcccctcact gacccaagac ttgaaccaca caatgggag   6240
aagtactgtg tcttgaggt aggagatatg cttctaagaa gtgccatagg ccatgtgtca   6300
aggcctatgt tcttgtatgt gaggacaaat ggaacctcaa aaattaaaat gaaatggggg   6360
atggaaatga ggcgttgcct ccttcagtca cttcaacaaa tcgagagtat gattgaagct   6420
gagtcctctg tcaaggagaa agacatgacc aaagagttct ttgaaaacaa atcagaaaca   6480
tggccccgttg gagagtcccc caaaggagtg gaggaaggtt ccattgggaa ggtctgcaga   6540
actttattgg caaagtcggt attcaacagc ttgtatgcat ctccacaact agaaggattt   6600
tcagctgaat caagaaaact gcttcttatc gttcaggctc ttagggacaa cctggaacct   6660
gggacctttg atcttggggg gctatatgaa gcaattgagg agtgcctgat taatgatccc   6720
tgggttttgc ttaatgcttc ttggttcaac tccttcctca cacatgcatt gagatagttg   6780
tggcaatgct actatttgct atccatactg tccaaaaacc aaaatgaagg caaaactact   6840
ggtcctgtta tatgcatttg tagctacaga tgcagacaca atatgtatag gctaccatgc   6900
gaacaactca accgacactg ttgacacaat actcgagaag aatgtggcag tgacacattc   6960
tgttaacctg ctcgaagaca gccacaacgg gaaactatgt aaattaaaag gaatagcccc   7020
actacaattg gggaaatgta acatcaccgg atggctcttg gaaatccag aatgcgactc   7080
actgcttcca gcgagatcat ggtcctacat tgtagaaaca ccaaactctg agaatggagc   7140
atgttatcca ggagatctca tcgactatga ggaactgagg gagcaattga gctcagtatc   7200
atcattagaa agattcgaaa tatttcccaa ggaaagttca tggcccaacc acacattcaa   7260
cggagtaaca gtatcatgct cccataggg aaaaagcagt ttttacagaa atttgctatg   7320
```

```
gctgacgaag aagggggatt catacccaaa gctgaccaat tcctatgtga acaataaagg   7380
gaaagaagtc cttgtactat ggggtgttca tcacccgtct agcagtgatg agcaacagag   7440
tctctatagt aatggaaatg cttatgtctc tgtagcgtct tcaaattata acaggagatt   7500
caccccggaa atagctgcaa ggcccaaagt aagagatcaa catgggagga tgaactatta   7560
ctggaccttg ctagaacccg agacacaat aatatttgag gcaactggta atctaatagc    7620
accatggtat gctttcgcac tgagtagagg gtttgagtcc ggcatcatca cctcaaacgc   7680
gtcaatgcat gagtgtaaca cgaagtgtca acaccccag ggagctataa acagcaatct    7740
ccctttccag aatatacacc cagtcacaat aggagagtgc ccaaaatatg tcaggagtac   7800
caaattgagg atggttacag gactaagaaa catcccatcc attcaataca gaggtctatt   7860
tggagccatt gctggtttta ttgagggggg atggactgga atgatagatg gatggtatgg   7920
ttatcatcat cagaatgaac agggatcagg ctatgcagcg gatcaaaaaa gcacacaaaa   7980
tgccattaac gggattacaa acaaggtgaa ctctgttatc gagaaaatga acactcaatt   8040
cacagctgtg ggtaaagaat tcaacaactt agaaaaaagg atggaaaatt taaataaaaa   8100
agttgatgat gggtttctgg acatttggac atataatgca gaattgttag ttctactgga   8160
aaatgaaagg actttggatt tccatgactt aaatgtgaag aatctgtacg agaaagtaaa   8220
aagccaatta aagaataatg ccaaagaaat cggaaatggg tgttttgagt tctaccacaa   8280
gtgtgacaat gaatgcatgg aaagtgtaag aaatgggact tatgattatc caaaatattc   8340
agaagaatca aagttgaaca gggaaaagat agatggagtg aaattggaat caatgggggt   8400
gtatcagatt ctggcgatct actcaactgt cgccagttca ctggtgcttt tggtctccct   8460 ggggcaatc agtttctgga tgtgttctaa tgggtctttg cagtgcagaa tatgcatctg    8520
agattaggat ttcagaaata taatagataa tcactcacag agtgacatcg aaatcatggc   8580
gaccaaaggc accaaacgat cttacgaaca gatggagact gatggagaac gccagaatgc   8640
cactgaaatc agagcatctg tcggaaaaat gattgatgga attggacgat tctacatcca   8700
aatgtgcacc gaacttaaac tcagtgatta tgagggacgg ctgattcaga acagcttaac   8760
aatagagaga atggtgctct ctgcttttga cgagaggagg aataaatatc tagaagaaca   8820
tcccagtgcg gggaaagatc ctaagaaaac tggaggacct atatacagga gagtagatgg   8880
aaagtggagg agagaactca tccttttatga caaagaagaa ataagacgaa tctggcgcca   8940
agctaataat ggtgacgatg caacggctgg tctgactcac atgatgatct ggcactccaa   9000
tttgaatgat gcaacttacc agaggacaag agctcttgtt cgcacaggaa tggatcccag   9060
gatgtgctca ctgatgcagg gttcaaccct ccctaggagg tctggggccg caggtgctgc   9120
agtcaaagga gttggaacaa tggtgatgga attgatcaga atgatcaaac gtgggatcaa   9180
tgatcggaac ttctggaggg gtgagaatgg acggagaaca aggattgctt atgaaagaat   9240
gtgcaacatt ctcaaaggga aatttcaaac agctgcacaa agaacaatgg tggatcaagt   9300
gagagagagc cggaatccag gaaatgctga gttcgaagat ctcatctttt tagcacggtc   9360
tgcactcata ttgagagggt cagttgctca caagtcctgc ctgcctgcct gtgtgtatgg   9420
atctgccgta gccagtggat acgactttga agagaggga tactctctag tcggaataga    9480
ccctttcaga ctgcttcaaa acagccaagt atacagccta atcagaccaa atgagaatcc   9540
agcacacaag agtcaactgg tgtggatggc atgccattct gctgcatttg aagatctaag   9600
agtatcaagc ttcatcagag ggacgaaagt ggtcccaaga gggaagcttt ccactagagg   9660
```

```
agttcaaatt gcttccaatg aaaacatgga gactatggaa tcaagtaccc ttgaactgag    9720
aagcagatac tgggccataa ggaccagaag tggagggaac accaatcaac agagggcttc    9780
ctcgggccaa atcagcatac aacctacgtt ctcagtacag agaaatctcc cttttgacag    9840
accaaccatt atggcagcat tcactgggaa tacagagggg agaacatctg acatgagaac    9900
cgaaatcata aggctgatgg aaagtgcaag accagaagat gtgtctttcc aggggcgggg    9960
agtcttcgag ctctcggacg aaaaggcaac gagcccgatc gtgccctcct ttgacatgag   10020
taatgaagga tcttatttct tcggagacaa tgcagaggag tacgacaatt aaagaaaaat   10080
gagtttaaat gaatccaaac cagaaaataa taaccattgg gtcaatctgt atggtagtcg   10140
gaataattag cctaatattg caaataggaa atataatctc aatatggatt agccattcaa   10200
ttcaaaccgg aaatcaaaac catactggaa tatgcaacca aggcagcatt acctataaag   10260
ttgttgctgg gcaggactca acttcagtga tattaaccgg caattcatct ctttgtccca   10320
tccgtgggtg ggctatacac agcaaagaca atggcataag aattggttcc aaaggagacg   10380 ttttttgtcat aagagagcct tttatttcat gttctcactt ggaatgcagg acctttttc   10440 tgactcaagg cgccttactg aatgacaagc attcaagggg gacctttaag gacagaagcc   10500
cttataggcc cttaatgagc tgccctgtcg gtgaagctcc gtcccgtac aattcaaggt   10560 ttgaatcggt tgcttggtca gcaagtgcat gtcatgatgg aatgggctgg ctaacaatcg   10620
gaatttctgg tccagatgat ggagcagtgg ctgtattaaa atacaaccgc ataataactg   10680
aaaccataaa aagttggagg aagaatatat tgagaacaca agagtctgaa tgtacctgtg   10740
taaatggttc atgttttacc ataatgaccg atggcccaag tgatgggctg gcctcgtaca   10800
aaattttcaa gatcgagaag gggaaggtta ctaaatcgat agagttgaat gcacctaatt   10860
ctcactacga ggaatgttcc tgttaccctg ataccggcaa agtgatgtgt gtgtgcagag   10920
acaattggca cggttcgaac cgaccatggg tgtccttcga ccaaaaccta gattataaaa   10980
taggatacat ctgcagtggg gttttcggtg acaacccgcg tcccaaagat ggaacaggca   11040
gctgtggccc agtgtctgct gatggagcaa acggagtaaa gggattttca tataagtatg   11100
gcaatggtgt ttggatagga aggactaaaa gtgacagttc cagacatggg tttgagatga   11160
tttgggatcc taatggatgg acagagactg atagtaggtt ctctatgaga caagatgttg   11220
tggcaataac taatcggtca gggtacagcg gaagtttcgt tcaacatcct gagctaacag   11280
ggctagactg tatgaggcct tgcttctggg ttgaattaat caggggcta cctgaggagg   11340 acgcaatctg gactagtggg agcatcattt ctttttgtgg tgtgaatagt gatactgtag   11400
attggtcttg gccagacggt gctgagttgc cgttcaccat tgacaagtag gtagatattg   11460
aaagatgagt cttctaaccg aggtcgaaac gtacgttctc tctatcgtcc cgtcaggccc   11520
cctcaaagcc gagatcgcac agagacttga agatgtcttt gcaggaagaa acaccgatct   11580
tgaggttctc atggaatggc taaagacaag accaatcctg tcacctctga ctaagggat   11640 tttaggattt gtgttcacgc tcaccgtgcc cagtgagcgg ggactgcagc gtagacgctt   11700
tgtccaaaat gctcttaatg ggaacggaga tccaaataac atggacaaag cagttaaact   11760
gtataggaag cttaagaggg agataacatt ccatggggcc aaagaaatag cactcagtta   11820
ttctgctggt gcacttgcct gttgtatggg cctcatatac aacaggatgg gggctgtgac   11880
cactgaagtg gcatttggcc tggtatgcgc aacctgtgaa cagattgctg actcccagca   11940
tcggtctcat aggcaaatgg tgacaacaac caatccacta atcagacatg agaacagaat   12000
ggttctagcc agcactacag ctaaggctat ggagcaaatg gctggatcga gtgagcaagc   12060
```

-continued

```
agcagaggcc atggatattg ctagtcaggc caggcaaatg gtgcaggcga tgagaaccgt   12120
tgggactcat cctagctcca gtgctggtct aaaagatgat cttcttgaaa atttacaggc   12180
ctatcagaaa cgaatggggg tgcagatgca acgattcaag tgatcctctc gtcattgcag   12240
caaatatcat tggaatcttg cacttgatat tgtggattct tgatcgtctt tttttcaaat   12300
gcatttatcg tcgctttaaa tacggtttga aagagggcc ttctaccgaa ggagtgccag    12360
agtctatgag gaagaatat cgaaggaac agcagaatgc tgtggatgtt gacgatggtc     12420
attttgtcaa catagagctg gagtaatgac aaagacataa tggatccaaa cactgtgtca   12480
agctttcagg tagattgctt tctttggcat gtccgcaaaa gagttgcaga ccaagaacta   12540
ggtgatgccc cattccttga tcggcttcgc cgagatcaga agtccctaag aggaagaggc   12600
agcactcttg gtctggacat cgaaacagcc cccgtgctg gaaagcaaat agtggagcgg    12660
attctgaagg aagaatctga tgaggcactc aaaatgacca tggcctctgt acctgcatcg   12720
cgctacctaa ctgacatgac tcttgaggaa atgtcaaggc actggttcat gctcatgccc   12780
aagcagaaag tggcaggccc tctttgtatc agaatggacc aggcgatcat ggataagaac   12840
atcatactga aagcgaactt cagtgtgatt tttgaccggc tggagactct aatattacta   12900
agggccttca ccgaagaggg gacaattgtt ggcgaaattt caccactgcc ctctcttcca   12960
ggacatactg atgaggatgt caaaaatgca gttggggtcc tcatcggagg acttgaatgg   13020
aataataaca cagttcgagt ctctgaaact ctacagagat cgcttggag aagcagtaat    13080 gagaatggga gacctccact cactccaaaa cagaaacgga aaatggcggg aacaattagg   13140
tcagaagttt gaagaaataa ggtggttgat tgaagaagtg agacacagac tgaagataac   13200
agagaatagt tttgagcaaa taacatttat gcaagcctta caactattgc ttgaagtgga   13260
gcaagagata agaactttct cgtttcagct tatttaataa                         13300
```

<210> SEQ ID NO 2
<211> LENGTH: 757
<212> TYPE: PRT
<213> ORGANISM: Influenza A virus WSN

<400> SEQUENCE: 2

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Arg Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Thr Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
```

|     |     |     |     |     |     |     |     |     |     |     |     |
|---|---|---|---|---|---|---|---|---|---|---|---|
| 145 |     |     |     | 150 |     |     |     | 155 |     |     | 160 |
| Gly | Arg | Leu | Ile | Asp | Phe | Leu | Lys | Asp | Val | Met | Glu | Ser | Met | Asn | Lys |
|     |     |     | 165 |     |     |     | 170 |     |     |     | 175 |

Glu Met Glu Ile Thr Thr His Phe Gln Arg Lys Arg Arg Val Arg
            180                     185                    190

Asp Asn Met Thr Lys Lys Met Val Thr Gln Arg Thr Ile Gly Lys Arg
            195                     200                    205

Lys Gln Arg Leu Asn Lys Arg Ser Tyr Leu Ile Arg Ala Leu Thr Leu
210                     215                    220

Asn Thr Met Thr Lys Asp Ala Glu Arg Gly Lys Leu Lys Arg Arg Ala
225                     230                    235                    240

Ile Ala Thr Pro Gly Met Gln Ile Arg Gly Phe Val Tyr Phe Val Glu
                245                     250                    255

Thr Leu Ala Arg Ser Ile Cys Glu Lys Leu Glu Gln Ser Gly Leu Pro
                260                     265                    270

Val Gly Gly Asn Glu Lys Lys Ala Lys Leu Ala Asn Val Val Arg Lys
                275                     280                    285

Met Met Thr Asn Ser Gln Asp Thr Glu Ile Ser Phe Thr Ile Thr Gly
        290                     295                    300

Asp Asn Thr Lys Trp Asn Glu Asn Gln Asn Pro Arg Met Phe Leu Ala
305                     310                    315                    320

Met Ile Thr Tyr Ile Thr Arg Asn Gln Pro Glu Trp Phe Arg Asn Val
                325                     330                    335

Leu Ser Ile Ala Pro Ile Met Phe Ser Asn Lys Met Ala Arg Leu Gly
                340                     345                    350

Lys Gly Tyr Met Phe Glu Ser Lys Ser Met Lys Leu Arg Thr Gln Ile
        355                     360                    365

Pro Ala Glu Met Leu Ala Ser Ile Asp Leu Lys Tyr Phe Asn Asp Ser
    370                     375                    380

Thr Arg Lys Lys Ile Glu Lys Ile Arg Pro Leu Leu Ile Asp Gly Thr
385                     390                    395                    400

Ala Ser Leu Ser Pro Gly Met Met Gly Met Phe Asn Met Leu Ser
                405                     410                    415

Thr Val Leu Gly Val Ser Ile Leu Asn Leu Gly Gln Lys Arg His Thr
                420                     425                    430

Lys Thr Thr Tyr Trp Trp Asp Gly Leu Gln Ser Ser Asp Asp Phe Ala
        435                     440                    445

Leu Ile Val Asn Ala Pro Asn His Glu Gly Ile Gln Ala Gly Val Asn
    450                     455                    460

Arg Phe Tyr Arg Thr Cys Lys Leu Leu Gly Ile Asn Met Ser Lys Lys
465                     470                    475                    480

Lys Ser Tyr Ile Asn Arg Thr Gly Thr Phe Glu Phe Thr Ser Phe Phe
                485                     490                    495

Tyr Arg Tyr Gly Phe Val Ala Asn Phe Ser Met Glu Leu Pro Ser Phe
                500                     505                    510

Gly Val Ser Gly Ile Asn Glu Ser Ala Asp Met Ser Ile Gly Val Thr
        515                     520                    525

Val Ile Lys Asn Asn Met Ile Asn Asn Asp Leu Gly Pro Ala Thr Ala
    530                     535                    540

Gln Met Ala Leu Gln Leu Phe Ile Lys Asp Tyr Arg Tyr Thr Tyr Arg
545                     550                    555                    560

Cys His Arg Gly Asp Thr Gln Ile Gln Thr Arg Arg Ser Phe Glu Ile
                565                     570                    575

```
Lys Lys Leu Trp Glu Gln Thr His Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
610                 615                 620

Cys Asn Pro Leu Asn Pro Phe Val Asn His Lys Asp Ile Glu Ser Val
625                 630                 635                 640

Asn Asn Ala Val Ile Met Pro Ala His Gly Pro Ala Lys Asn Met Glu
                    645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                    725                 730                 735

Lys Glu Glu Phe Thr Glu Ile Met Lys Ile Cys Ser Thr Ile Glu Glu
                740                 745                 750

Leu Arg Arg Gln Lys
            755

<210> SEQ ID NO 3
<211> LENGTH: 759
<212> TYPE: PRT
<213> ORGANISM: Influenza A virus WSN

<400> SEQUENCE: 3

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Thr
        50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Val Thr Ser Thr Val His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Thr Thr Lys Glu Lys Lys Glu Glu
```

```
            180                 185                 190
Leu Gln Gly Cys Lys Ile Ser Pro Leu Met Val Ala Tyr Met Leu Glu
            195                 200                 205

Arg Glu Leu Val Arg Lys Thr Arg Phe Leu Pro Val Ala Gly Gly Thr
        210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Ala Arg Asn Asp Val Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Val Arg Met Val Asn Ile Leu Arg Gln Asn Pro Thr Glu
            290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Val Leu Thr Gly Asn Leu Gln Thr Leu
            340                 345                 350

Lys Ile Arg Val His Glu Gly Tyr Glu Glu Phe Thr Met Val Gly Arg
            355                 360                 365

Arg Ala Thr Ala Ile Leu Arg Lys Ala Thr Arg Leu Ile Gln Leu
        370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
        435                 440                 445

Trp Gly Ile Glu Ser Ile Asp Asn Val Met Gly Met Ile Gly Ile Leu
    450                 455                 460

Pro Asp Met Thr Pro Ser Thr Glu Met Ser Met Arg Gly Val Arg Ile
465                 470                 475                 480

Ser Lys Met Gly Val Asp Glu Tyr Ser Ser Ala Glu Lys Ile Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Val Arg Gly Gln Tyr
                580                 585                 590

Ser Gly Phe Val Arg Thr Leu Phe Gln Gln Met Arg Asp Val Leu Gly
        595                 600                 605
```

-continued

```
Thr Phe Asp Thr Ala Gln Ile Ile Lys Leu Leu Pro Phe Ala Ala Ala
            610                 615                 620

Pro Pro Lys Gln Ser Gly Met Gln Phe Ser Ser Leu Thr Ile Asn Val
625                 630                 635                 640

Arg Gly Ser Gly Met Arg Ile Leu Val Arg Gly Asn Ser Pro Val Phe
            645                 650                 655

Asn Tyr Asn Lys Thr Thr Lys Arg Leu Thr Val Leu Gly Lys Asp Ala
                660                 665                 670

Gly Pro Leu Thr Glu Asp Pro Asp Glu Gly Thr Ala Gly Val Glu Ser
            675                 680                 685

Ala Val Leu Arg Gly Phe Leu Ile Leu Gly Lys Glu Asp Arg Arg Tyr
690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asn Ser Ser Ile Leu Thr Asp Ser Gln Thr Ala Thr Lys
            740                 745                 750

Arg Ile Arg Met Ala Ile Asn
            755

<210> SEQ ID NO 4
<211> LENGTH: 105
<212> TYPE: PRT
<213> ORGANISM: Influenza A virus WSN

<400> SEQUENCE: 4

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Gln Leu Glu Gly Phe Ser
        35                  40                  45

Ala Glu Ser Arg Lys Leu Leu Leu Ile Val Gln Ala Leu Arg Asp Asn
    50                  55                  60

Leu Glu Pro Gly Thr Phe Asp Leu Gly Gly Leu Tyr Glu Ala Ile Glu
65                  70                  75                  80

Glu Cys Leu Ile Asn Asp Pro Trp Val Leu Leu Asn Ala Ser Trp Phe
                85                  90                  95

Asn Ser Phe Leu Thr His Ala Leu Arg
            100                 105

<210> SEQ ID NO 5
<211> LENGTH: 252
<212> TYPE: PRT
<213> ORGANISM: Influenza A virus WSN

<400> SEQUENCE: 5

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60
```

```
Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Asp Ile Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 6
<211> LENGTH: 97
<212> TYPE: PRT
<213> ORGANISM: Influenza A virus WSN
<400> SEQUENCE: 6

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Ile Ala Ala Asn Ile
            20                  25                  30

Ile Glu Ile Leu His Leu Ile Leu Trp Ile Leu Asp Arg Leu Phe Phe
        35                  40                  45

Lys Cys Ile Tyr Arg Arg Phe Lys Tyr Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Val Asp Asp Gly His Phe Val Asn Ile Glu Leu
                85                  90                  95

Glu

<210> SEQ ID NO 7
<211> LENGTH: 230
<212> TYPE: PRT
<213> ORGANISM: Influenza A virus WSN
<400> SEQUENCE: 7

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30
```

-continued

```
Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg His Trp Phe Met Leu Met Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Thr Ile Val Gly Glu Ile
145                 150                 155                 160

Ser Pro Leu Pro Ser Leu Pro Gly His Thr Asp Glu Asp Val Lys Asn
                165                 170                 175

Ala Val Gly Val Leu Ile Gly Gly Leu Glu Trp Asn Asn Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Lys Met Ala Gly
    210                 215                 220

Thr Ile Arg Ser Glu Val
225                 230
```

<210> SEQ ID NO 8
<211> LENGTH: 2303
<212> TYPE: DNA
<213> ORGANISM: Influenza A virus WSN

<400> SEQUENCE: 8

```
atttgaatgg atgtcaatcc gactttactt ttcttaaaag tgccagcaca aaatgctata      60
agcacaactt tcccttatac tggagaccct ccttacagcc atgggacagg aacaggatac     120
accatggata ctgtcaacag gacacatcag tactcagaaa ggggaagatg gacaacaaac     180
accgaaactg gagcaccgca actcaacccg attgatgggc cactgccaga agacaatgaa     240
ccaagtggtt atgcccaaac agattgtgta ttggaagcaa tggccttcct tgaggaatcc     300
catcctggta tctttgagac ctcgtgtctt gaaacgatgg aggttgttca gcaaacacga     360
gtggacaagc tgacacaagg ccgacagacc tatgactgga ctctaaatag gaaccagcct     420
gctgcaacag cattggccaa cacaatagaa gtgttcagat caaatggcct cacggccaat     480
gaatctggaa ggctcataga cttccttaag gatgtaatgg agtcaatgaa caaagaagaa     540
atggagatca caactcattt tcagagaaaa agacgagtga gagacaatat gactaagaaa     600
atggtgacac agagaacaat aggtaaaagg aagcagagat tgaacaaaag gagttatcta     660
attagggcat taaccctgaa cacaatgacc aaagatgctg agagagggaa gctaaaacgg     720
agagcaattg caaccccagg gatgcaaata agggggtttg tatactttgt tgagacacta     780
gcaaggagta tatgtgagaa acttgaacaa tcaggattgc cagttggagg caatgagaag     840
aaagcaaagt tggcaaatgt tgtaaggaag atgatgacca attctcagga cactgaaatt     900
tctttcacca tcactggaga taacaccaaa tggaacgaaa atcagaaccc tcggatgttt     960
```

-continued

```
ttggccatga tcacatatat aaccagaaat cagcccgaat ggttcagaaa tgttctaagt   1020
attgctccaa taatgttctc aaacaaaatg gcgagactgg gaaagggta catgtttgag    1080
agcaagagta tgaaaattag aactcaaata cctgcagaaa tgctagcaag catcgatttg   1140
aaatacttca atgattcaac tagaaagaag attgaaaaaa tccggccgct cttaatagat   1200
gggactgcat cattgagccc tggaatgatg atgggcatgt tcaatatgtt aagtactgta   1260
ttaggagtct ccatcctgaa tcttggacaa aagagacaca ccaagactac ttactggtgg   1320
gatggtcttc aatcttctga tgattttgct ctgattgtga atgcacccaa tcatgaaggg   1380
attcaagccg gagtcaacag gttttatcga acctgtaagc tacttggaat taatatgagc   1440
aagaaaaagt cttacataaa cagaacaggt acatttgaat tcacaagttt tttctatcgt   1500
tatgggtttg ttgccaattt cagcatgag ctcccagct ttggggtgtc tgggatcaac     1560
gagtctgcgg acatgagtat ggagttact gtcatcaaaa acaatatgat aaacaatgat    1620
cttggtccag caaccgctca atggccctt cagctgttca tcaaagatta caggtacacg    1680
taccggtgcc atagaggtga cacacaaata caaacccgaa gatcatttga aataaagaaa   1740
ctgtgggagc aaacccattc caaagctgga ctgctggtct ccgacggagg cccaaattta   1800
tacaacatta gaaatctcca cattcctgaa gtctgcttga atgggaatt aatggatgag    1860
gattaccagg ggcgtttatg caacccactg aacccatttg tcaaccataa agacattgaa   1920
tcagtgaaca atgcagtgat aatgccagca catggtccag ccaaaaacat ggagtatgat   1980
gctgttgcaa caacacactc ctggatcccc aaaagaaatc gatccatctt gaatacaagc   2040
caaagaggaa tacttgaaga tgaacaaatg taccaaagt gctgcaactt atttgaaaaa    2100
ttcttcccca gcagttcata cagaagacca gtcgggatat ccagtatggt ggaggctatg   2160
gtttccagag cccgaattga tgcacgaatt gatttcgaat ctggaaggat aaagaaagag   2220
gagttcactg agatcatgaa gatctgttcc accattgaag agctcagacg gcaaaaatag   2280
tgaatttagc ttgtccttca tga                                           2303
```

<210> SEQ ID NO 9
<211> LENGTH: 2202
<212> TYPE: DNA
<213> ORGANISM: Influenza A virus WSN

<400> SEQUENCE: 9

```
ctgattcaaa atggaagatt ttgtgcgaca atgcttcaat ccgatgattg tcgagcttgc     60
ggaaaaggca atgaaagagt atggagagga cctgaaaatc gaaacaaaca aatttgcagc    120
aatatgcact cacttggaag tgtgcttcat gtattcagat tttcacttca tcgatgagca    180
aggcgagtca atagtcgtag aacttggcga tccaaatgca cttttgaagc acagatttga    240
aataatcgag ggaagagatc gcacaatagc ctggacagta ataaacagta tttgcaacac    300
tacaggggct gagaaaccaa agtttctacc agatttgtat gattacaaga agaatagatt    360
catcgaaatt ggagtaacaa ggagagaagt tcacatatac tatctggaaa aggccaataa    420
aattaaatct gagaagacac acatccacat tttctcattc actggggagg aaatggccac    480
aaaggccgac tacactctcg atgaagaaag cagggctagg atcaaaacca ggctattcac    540
cataagacaa gaaatggcta gcagaggcct ctgggattcc tttcgtcagt ccgagagagg    600
cgaagagaca attgaagaaa gatttgaaat cacaggaaca atgcgcaagc ttgccgacca    660
aagtctcccg ccaaacttct ccagccttga aaaatttaga gcctatgtgg atggattcga    720
accgaacggc tacattgagg gcaagctttc tcaaatgtcc aaagaagtaa atgctagaat    780
```

-continued

```
tgaacctttt ttgaaatcaa caccacgacc acttagactt ccggatgggc ctccctgttc    840
tcagcggtcc aaattcctgc tgatggatgc cttaaaatta agcattgagg acccaagtca    900
tgagggagag gggataccgc tatatgatgc aatcaaatgc atgagaacat tctttggatg    960
gaaggaaccc aatgttgtta aaccacacga aagggaata aatccaaatt atcttctgtc    1020
atggaagcaa gtactggcag aactgcagga cattgagaat gaggagaaaa ttccaaggac    1080
taaaaatatg aagaaaacga gtcagttaaa gtgggcactt ggtgagaaca tggcaccaga    1140
aaaggtagac tttgacgatt gtaaagatgt aggcgatttg aagcaatatg atagtgatga    1200
accagaattg aggtcgcttg caagttggat tcagaatgag ttcaacaagg catgtgaact    1260
gaccgattca agctggatag agctcgatga gattggagaa gatgcggctc caattgaaca    1320
cattgcaagc atgagaagga attatttcac agcagaggtg tctcattgca gagccacaga    1380
atacataatg aaggggtgt acatcaatac tgccttgctt aatgcatcct gtgcagcaat    1440
ggatgatttc caattaattc caatgataag caagtgtaga actaaggagg aaggcgaaa    1500 gaccaatttg tacggtttca tcataaaagg aagatcccac ttaaggaatg acaccgatgt    1560
ggtaaacttt gtgagcatgg agttttccct cactgaccca agacttgaac cacacaaatg    1620
ggagaagtac tgtgttcttg aggtaggaga tatgcttcta agaagtgcca taggccatgt    1680
gtcaaggcct atgttcttgt atgtgaggac aaatggaacc tcaaaaatta aaatgaaatg    1740
ggggatggaa atgaggcgtt gcctccttca gtcacttcaa caaatcgaga gtatgattga    1800
agctgagtcc tctgtcaagg agaaagacat gaccaaagag ttctttgaaa acaaatcaga    1860
aacatggccc gttggagagt ccccaaagg agtggaggaa ggttccattg ggaaggtctg    1920 cagaactta ttggcaaagt cggtattcaa cagcttgtat gcatctccac aactagaagg    1980
attttcagct gaatcaagaa aactgcttct tatcgttcag gctcttaggg acaacctgga    2040
acctgggacc tttgatcttg gggggctata tgaagcaatt gaggagtgcc tgattaatga    2100
tccctgggtt ttgcttaatg cttcttggtt caactccttc ctcacacatg cattgagata    2160
gttgtggcaa tgctactatt tgctatccat actgtccaaa aa    2202
```

<210> SEQ ID NO 10
<211> LENGTH: 1725
<212> TYPE: DNA
<213> ORGANISM: Influenza A virus WSN

<400> SEQUENCE: 10

```
ccaaaatgaa ggcaaaacta ctggtcctgt tatatgcatt tgtagctaca gatgcagaca    60
caatatgtat aggctaccat gcgaacaact caaccgacac tgttgacaca atactcgaga    120
agaatgtggc agtgacacat tctgttaacc tgctcgaaga cagccacaac gggaaactat    180
gtaaattaaa aggaatagcc ccactacaat gggggaaatg taacatcacc ggatggctct    240
tgggaaatcc agaatgcgac tcactgcttc cagcgagatc atggtcctac attgtagaaa    300
caccaaactc tgagaatgga gcatgttatc caggagatct catcgactat gaggaactga    360
gggagcaatt gagctcagta tcatcattag aaagattcga atatttccc aaggaaagtt    420 catggcccaa ccacacattc aacgagtaa cagtatcatg ctcccatagg ggaaaaagca    480 gttttttacag aaatttgcta tggctgacga agaaggggga ttcatacca agctgacca    540 attcctatgt gaacaataaa gggaagaag tccttgtact atgggggtgtt catcacccgt    600 ctagcagtga tgagcaacag agtctctata gtaatggaaa tgcttatgtc tctgtagcgt    660
```

```
cttcaaatta taacaggaga ttcaccccgg aaatagctgc aaggcccaaa gtaagagatc     720
aacatgggag gatgaactat tactggacct tgctagaacc cggagacaca ataatatttg     780
aggcaactgg taatctaata gcaccatggt atgctttcgc actgagtaga gggtttgagt     840
ccggcatcat cacctcaaac gcgtcaatgc atgagtgtaa cacgaagtgt caaacacccc     900
agggagctat aaacagcaat ctccctttcc agaatataca cccagtcaca ataggagagt     960
gcccaaaata tgtcaggagt accaaattga ggatggttac aggactaaga acatcccat    1020 ccattcaata cagaggtcta tttggagcca ttgctggttt tattgagggg ggatggactg    1080
gaatgataga tggatggtat ggttatcatc atcagaatga acagggatca ggctatgcag    1140
cggatcaaaa aagcacacaa atgccatta cgggattac aaacaaggtg aactctgtta    1200
tcgagaaaat gaacactcaa ttcacagctg tgggtaaaga attcaacaac ttagaaaaaa    1260
ggatggaaaa tttaaataaa aaagttgatg atgggtttct ggacatttgg acatataatg    1320
cagaattgtt agttctactg gaaaatgaaa ggactttgga tttccatgac ttaaatgtga    1380
agaatctgta cgagaaagta aaaagccaat taaagaataa tgccaaagaa atcggaaatg    1440
ggtgttttga gttctaccac aagtgtgaca tgaatgcat ggaaagtgta agaaatggga    1500
cttatgatta tccaaaatat tcagaagaat caaagttgaa cagggaaaag atagatggag    1560
tgaaattgga atcaatgggg gtgtatcaga ttctggcgat ctactcaact gtcgccagtt    1620
cactggtgct tttggtctcc ctgggggcaa tcagtttctg gatgtgttct aatgggtctt    1680
tgcagtgcag aatatgcatc tgagattagg atttcagaaa tataa                   1725
```

<210> SEQ ID NO 11
<211> LENGTH: 1537
<212> TYPE: DNA
<213> ORGANISM: Influenza A virus WSN

<400> SEQUENCE: 11

```
tagataatca ctcacagagt gacatcgaaa tcatggcgac caaaggcacc aaacgatctt      60
acgaacagat ggagactgat ggagaacgcc agaatgccac tgaaatcaga gcatctgtcg     120
gaaaaatgat tgatggaatt ggacgattct acatccaaat gtgcaccgaa cttaaactca     180
gtgattatga gggacggctg attcagaaca gcttaacaat agagagaatg gtgctctctg     240
cttttgacga gaggaggaat aaatatctag aagaacatcc cagtgcgggg aaagatccta     300
agaaaactgg aggacctata tacaggagag tagatggaaa gtggaggaga gaactcatcc     360
tttatgacaa agaagaaata agacgaatct ggcgccaagc taataatggt gacgatgcaa     420
cggctggtct gactcacatg atgatctggc actccaattt gaatgatgca acttaccaga     480
ggacaagagc tcttgttcgc acaggaatgg atcccaggat gtgctcactg atgcagggtt     540
caaccctccc taggaggtct ggggccgcag gtgctgcagt caaggagtt ggaacaatgg     600 tgatggaatt gatcagaatg atcaaacgtg ggatcaatga tcggaacttc tggagggtg     660 agaatggacg gagaacaagg attgcttatg aaagaatgtg caacattctc aaagggaaat     720
ttcaaacagc tgcacaaaga caatggtgg atcaagtgag agagagccgg aatccaggaa     780
atgctgagtt cgaagatctc atcttttag cacggtctgc actcatattg agagggtcag     840
ttgctcacaa gtcctgcctg cctgcctgtg tgtatggatc tgccgtagcc agtggatacg     900
actttgaaag agagggatac tctctagtcg gaatagaccc tttcagactg cttcaaaaca     960
gccaagtata cagcctaatc agaccaaatg agaatccagc acacaagagt caactggtgt    1020
ggatggcatg ccattctgct gcatttgaag atctaagagt atcaagcttc atcagaggga    1080
```

| | | |
|---|---|---|
| cgaaagtggt cccaagaggg aagctttcca ctagaggagt tcaaattgct tccaatgaaa | 1140 | |
| acatggagac tatggaatca agtaccgttg aactgagaag cagatactgg gccataagga | 1200 | |
| ccagaagtgg agggaacacc aatcaacaga gggcttcctc gggccaaatc agcatacaac | 1260 | |
| ctacgttctc agtacagaga aatctcccct ttgacagacc aaccattatg gcagcattca | 1320 | |
| ctgggaatac agagggggaga acatctgaca tgagaaccga atcataagg ctgatggaaa | 1380 | |
| gtgcaagacc agaagatgtg tctttccagg ggcgggagt cttcgagctc tcggacgaaa | 1440 | |
| aggcaacgag cccgatcgtg ccctccttg acatgagtaa tgaaggatct tatttcttcg | 1500 | |
| gagacaatgc agaggagtac gacaattaaa gaaaaat | 1537 | |

<210> SEQ ID NO 12
<211> LENGTH: 1370
<212> TYPE: DNA
<213> ORGANISM: Influenza A virus WSN

<400> SEQUENCE: 12

| | | |
|---|---|---|
| gagtttaaat gaatccaaac cagaaaataa taaccattgg gtcaatctgt atggtagtcg | 60 | |
| gaataattag cctaatattg caaataggaa atataatctc aatatggatt agccattcaa | 120 | |
| ttcaaaccgg aaatcaaaac catactggaa tatgcaacca aggcagcatt acctataaag | 180 | |
| ttgttgctgg gcaggactca acttcagtga ttattaaccgg caattcatct ctttgtccca | 240 | |
| tccgtgggtg ggctatacac agcaaagaca atggcataag aattggttcc aaaggagacg | 300 | |
| tttttgtcat aagagagcct tttatttcat gttctcactt ggaatgcagg accttttttc | 360 | |
| tgactcaagg cgccttactg aatgacaagc attcaagggg gacctttaag gacagaagcc | 420 | |
| cttatagggc cttaatgagc tgccctgtcg gtgaagctcc gtccccgtac aattcaaggt | 480 | |
| ttgaatcggt tgcttggtca gcaagtgcat gtcatgatga atgggctgg ctaacaatcg | 540 | |
| gaatttctgg tccagatgat ggagcagtgg ctgtattaaa atacaaccgc ataataactg | 600 | |
| aaaccataaa aagttggagg aagaatatat tgagaacaca agagtctgaa tgtacctgtg | 660 | |
| taaatggttc atgttttacc ataatgaccg atggcccaag tgatgggctg gcctcgtaca | 720 | |
| aaattttcaa gatcgagaag gggaaggtta ctaaatcgat agagttgaat gcacctaatt | 780 | |
| ctcactacga ggaatgttcc tgttacccctg ataccggcaa agtgatgtgt gtgtgcagag | 840 | |
| acaattggca cggttcgaac cgaccatggg tgtccttcga ccaaaaccta gattataaaa | 900 | |
| taggatacat ctgcagtggg gttttcggtg acaacccgcg tcccaaagat ggaacaggca | 960 | |
| gctgtggccc agtgtctgct gatggagcaa acggagtaaa gggattttca tataagtatg | 1020 | |
| gcaatggtgt ttggataggga aggactaaaa gtgacagttc cagacatggg tttgagatga | 1080 | |
| tttgggatcc taatgatgg acagagactg atagtaggtt ctctatgaga caagatgttg | 1140 | |
| tggcaataac taatcggtca gggtacagcg gaagtttcgt tcaacatcct gagctaacag | 1200 | |
| ggctagacta tgaggcct tgcttctggg ttgaattaat caggggggcta cctgaggagg | 1260 | |
| acgcaatctg gactagtggg agcatcattt ctttttgtgg tgtgaatagt gatactgtag | 1320 | |
| attggtcttg gccagacggt gctgagttgc cgttcaccat tgacaagtag | 1370 | |

<210> SEQ ID NO 13
<211> LENGTH: 996
<212> TYPE: DNA
<213> ORGANISM: Influenza A virus WSN

<400> SEQUENCE: 13

-continued

```
gtagatattg aaagatgagt cttctaaccg aggtcgaaac gtacgttctc tctatcgtcc     60
cgtcaggccc cctcaaagcc gagatcgcac agagacttga agatgtcttt gcagggaaga    120
acaccgatct tgaggttctc atggaatggc taaagacaag accaatcctg tcacctctga    180
ctaaggggat tttaggattt gtgttcacgc tcaccgtgcc cagtgagcgg ggactgcagc    240
gtagacgctt tgtccaaaat gctcttaatg ggaacggaga tccaaataac atggacaaag    300
cagttaaact gtataggaag cttaagaggg agataacatt ccatggggcc aaagaaatag    360
cactcagtta ttctgctggt gcacttgcct gttgtatggg cctcatatac aacaggatgg    420
gggctgtgac cactgaagtg gcatttggcc tggtatgcgc aacctgtgaa cagattgctg    480
actcccagca tcggtctcat aggcaaatgg tgacaacaac caatccacta atcagacatg    540
agaacagaat ggttctagcc agcactacag ctaaggctat ggagcaaatg gctggatcga    600
gtgagcaagc agcagaggcc atggatattg ctagtcaggc caggcaaatg gtgcaggcga    660
tgagaaccgt tgggactcat cctagctcca gtgctggtct aaaagatgat cttcttgaaa    720
atttacaggc ctatcagaaa cgaatggggg tgcagatgca acgattcaag tgatcctctc    780
gtcattgcag caaatatcat tggaatcttg cacttgatat tgtggattct tgatcgtctt    840
tttttcaaat gcatttatcg tcgctttaaa tacggtttga aaagagggcc ttctaccgaa    900
ggagtgccag agtctatgag ggaagaatat cgaaaggaac agcagaatgc tgtggatgtt    960
gacgatggtc attttgtcaa catagagctg gagtaa                              996
```

<210> SEQ ID NO 14
<211> LENGTH: 854
<212> TYPE: DNA
<213> ORGANISM: Influenza A virus WSN

<400> SEQUENCE: 14

```
tgacaaagac ataatggatc caaacactgt gtcaagcttt caggtagatt gctttctttg     60
gcatgtccgc aaaagagttg cagaccaaga actaggtgat gccccattcc ttgatcggct    120
tcgccgagat cagaagtccc taagaggaag aggcagcact cttggtctgg acatcgaaac    180
agccacccgt gctggaaagc aaatagtgga gcggattctg aaggaagaat ctgatgaggc    240
actcaaaatg accatggcct ctgtacctgc atcgcgctac ctaactgaca tgactcttga    300
ggaaatgtca aggcactggt tcatgctcat gcccaagcag aaagtggcag gccctctttg    360
tatcagaatg gaccaggcga tcatggataa gaacatcata ctgaaagcga acttcagtgt    420
gatttttgac cggctggaga ctctaatatt actaagggcc ttcaccgaag aggggacaat    480
tgttggcgaa atttcaccac tgccctctct tccaggacat actgatgagg atgtcaaaaa    540
tgcagttggg gtcctcatcg gaggacttga atggaataat aacacagttc gagtctctga    600
aactctacag agattcgctt ggagaagcag taatgagaat gggagacctc cactcactcc    660
aaaacagaaa cggaaaatgg cgggaacaat taggtcagaa gtttgaagaa ataaggtggt    720
tgattgaaga agtgagacac agactgaaga taacagagaa tagttttgag caaataacat    780
ttatgcaagc cttacaacta ttgcttgaag tggagcaaga gataagaact ttctcgtttc    840
agcttattta ataa                                                      854
```

GENOME-WIDE IDENTIFICATION OF IMMUNE EVASION FUNCTIONS IN A VIRUS

CROSS REFERENCE TO RELATED APPLICATIONS

This application claims the benefit under 35 U.S.C. Section 119(e) of co-pending and commonly-assigned U.S. Provisional Patent Application Ser. No. 62/471,269, filed on Mar. 14, 2017, by Yushen Du, Nicholas C. Wu, and Ren Sun, entitled "GENOME-WIDE IDENTIFICATION OF IMMUNE EVASION FUNCTIONS IN A VIRUS AT AMINO ACID RESOLUTION AND RATIONAL DEVELOPMENT OF IMMUNE THERAPIES-REDUCTION TO PRACTICE WITH ANTI-INTERFERON FUNCTIONS ON INFLUENZA VIRUS", (2017-515-1); which application is incorporated by reference herein.

SEQUENCE LISTING

The instant application contains a Sequence Listing which has been submitted electronically in ASCII format and is hereby incorporated by reference in its entirety. Said ASCII copy, created on Mar. 1, 2023, is named 30435_0330USWO_SL.txt and is 51,949 bytes in size.

TECHNICAL FIELD

This invention relates to systems and methods for enhancing immune response and/or making pharmaceutical compositions.

BACKGROUND OF THE INVENTION

Most viruses adapt rapidly to diverse selection pressures, posing a challenge for deploying safe and effective vaccines. Influenza viruses, for example, are characterized by large genetic diversity across subtypes and rapid antigenic drift and shift, which present problems for traditional vaccine strategies. Attenuation or inactivation of viruses tends to reduce the strength and breadth of immune responses, resulting in ineffective protection against antigenic alterations (1-3). Previous pandemics and recent influenza outbreaks highlight the need to develop safe vaccines that elicit effective immune responses and confer broad protection. Influenza A wild type WSN/1933(H1N1) strain is well known in the art and the complete sequence can be found in reference (51).

The type I interferon (IFN) system is the major component of innate immune responses (4-6). The IFN response provides the first line of defense against viral infections by inducing the expression of hundreds of IFN-stimulated genes (ISGs), many of which have antiviral activities (7). The IFN response is also critical for dendritic cell maturation, development of B and T cells, and memory formation, bridging innate and adaptive immunity (8-12). Most viruses have evolved to efficiently suppress the production and function of IFN to allow replication in vivo. Removing the most well-characterized IFN modulator in influenza virus— namely, the NS1 protein—has shown promise in a vaccine candidate (delNS1) in phase ½ clinical trials (14, 15). Although studies have suggested that influenza proteins other than NS1 have IFN-modulating functions (16, 17), genome-wide identification and elimination of IFN-modulating functions without affecting viral replication fitness in vitro have remained challenging tasks.

SUMMARY OF THE INVENTION

Conventional vaccine and/or viral vectors used in immune therapy are typically built from the natural isolates or regenerated using existing knowledge. As discussed in detail below, we have discovered and developed a different approach for vaccine development, one that involves systematically identifying immune evasion functions of a pathogen genome used in the vaccine (e.g., a virus such as influenza), and then eliminating the immune evasion functions while maintaining or tuning the replication fitness of the virus genome. While influenza A is used as an illustrative working embodiment of the invention, this method is broadly applicable to vaccine development in a wide variety of pathogens.

Embodiments of our method are implemented using a systematic high-throughput mutagenesis system to reveal the potential IFN sensitive mutations across a viral genome (influenza A). This mutagenesis system can generate comprehensive information with amino acid or nucleotide resolution that enables construction of novel vectors with desired properties. Moreover, multiple screens can be performed to identify other mutations/features that enhance the properties of the products. In this context, by controlling a combination of mutations in the virus genome, a replication/immune response trade-off can be fine-tuned to achieve desirable efficiency and safety when the virus genome is administered as a vaccine or as a therapeutic agent. In an illustrative embodiment of the invention using the influenza virus, a carefully selected combination of nucleotide mutations generates an invention that is surprisingly capable of stimulating an elevated antibody response, while simultaneously being highly attenuated in vivo due to suppressed viral replication brought about by these mutations.

In the illustrative embodiments of the invention that are directed to the influenza A viral genome, combinations of nucleotide mutations are engineered using a genetic system. In this illustrative working embodiment, the invention provides a single-nucleotide resolution high-throughput genetics approach that simultaneously measures/profiles fitness effects of mutations at >50% of the nucleotide positions in the influenza A virus genome under different conditions. Applying this approach, we have systematically identified anti-interferon functional residues across the whole influenza A/WSN/33 genome, by measuring viral fitness in the presence or absence of interferon. Specifically, we identified and validated interferon sensitive mutations across the influenza A/WSN/33 genome and validated clusters of mutations at PB2 and M1 interacting with the interferon system. Interferon sensitive mutations were found on most segments, in addition to NS1. Clusters of mutations at PB2 and M1 can induce higher interferon production. By combining multiple mutations together (e.g., by combining multiple mutations on PB2, M1 and NS1), we generated a highly interferon sensitive strain as a live attenuated vaccine candidate, which we called a hyper-interferon-sensitive (HIS) virus strain (in one or more examples, also the DAI-1 (Deficient of Anti-Interferon) strain referred to in the priority U.S. Provisional Patent Application Ser. No. 62/471,269, filed on Mar. 14, 2017). The HIS strain can replicate efficiently in interferon-deficient cell lines (e.g., Vero cells) and mice (e.g., interferon-deficient mice such as IFNRA−/− mice). Despite the HIS being attenuated in normal cells and highly attenuated in wild type mice (BALBc), the HIS none-the-less generates surprisingly and unexpectedly robust antibody and T cell responses in mice that inhibit the challenge infection of wild type influenza virus.

Moreover, as the combination of multiple mutations can be located in different gene segments and are mostly neutral for viral replication without interferon selection, the risk of a revertant due to do novo mutation or gene assortment is greatly reduced.

The methods described herein are broadly applicable to the fabrication of genetically engineered pathogens useful as vaccines and/or therapeutic agents and/or pharmaceutical compositions. A therapeutic agent comprising a pathogen genetically engineered according to the method(s) described herein would be particularly useful for patients infected with a drug resistant virus.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 5 HIS virus protects mice and ferrets from broad viral challenges. (A and B) Viral load in mouse lung tissues at day 2 post-challenge (n=4). DV, double vaccinations with HIS virus at $1 \times 10^4$ TCID50, 28 days apart; HD, high-dose vaccination with HIS virus at $1 \times 10^6$ TCID50. Dashed lines represent detection limits. (C) Viral replication kinetics in ferret nasal wash after WSN virus challenge at day 35 post-vaccination (n=3). (D and E) Survival rate and body weight loss of HIS-vaccinated mice after challenge with homologous and heterologous strains (n=10). (F) Viral replication kinetics in ferret nasal wash after A/California/07/09 virus challenge at 35 days post-vaccination (n=3). Error bars, SD. *P<0.05, ***P<0.001 [ANOVA with Bonferroni multiple comparisons test for (A) and (B), two-tailed t test for (C) and (F), and log-rank test for (D)].

Figure 6:
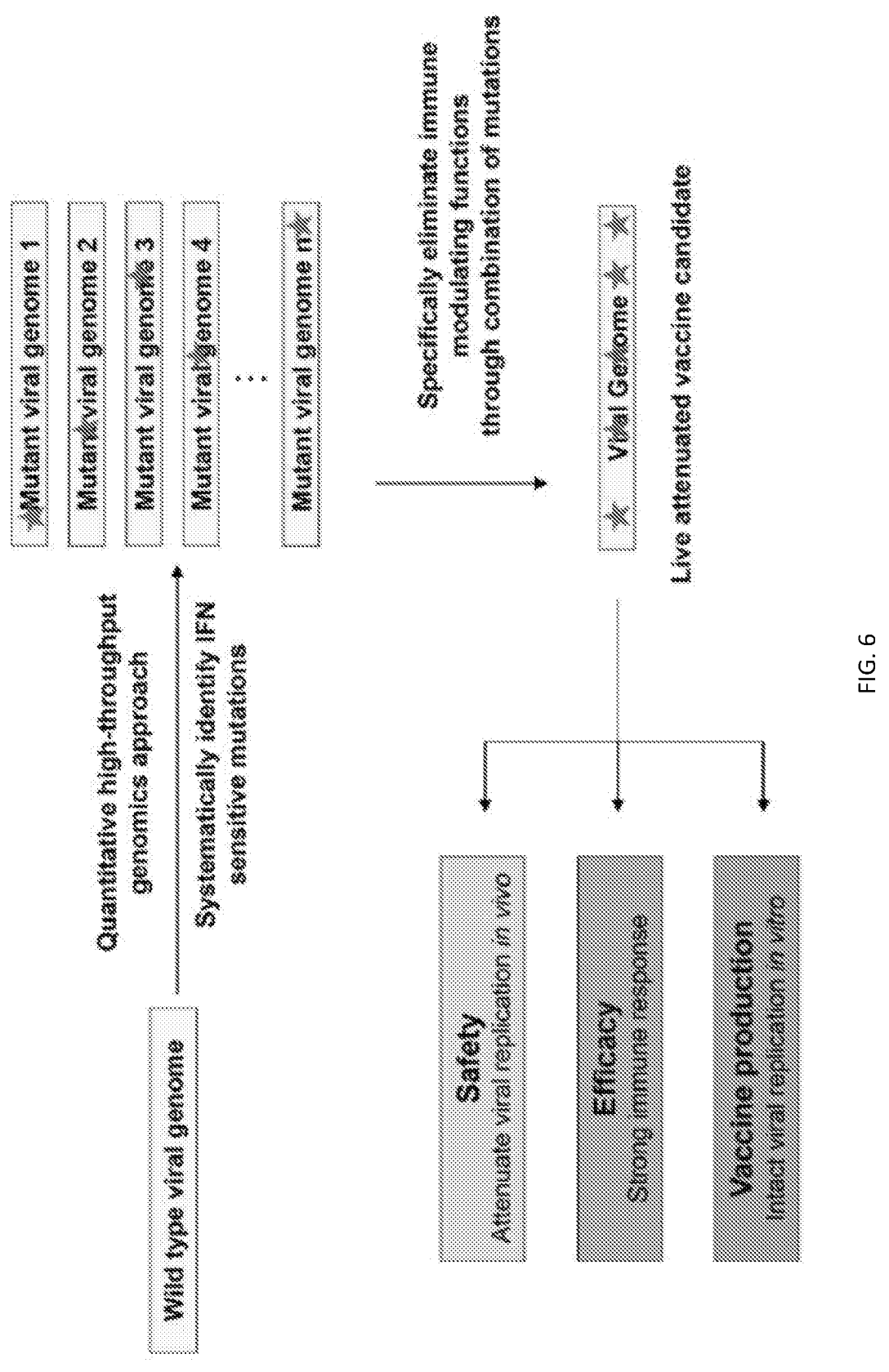

FIG. 6: Experimental design and rationale of a vaccine development approach

Flow chart shows the experimental design and rationale of our vaccine development approach. Through the development of a quantitative high-throughput genomics system (18, 19, 59-61), we were able to measure the phenotypic effect of single nucleotide mutations in the viral genome under different selection conditions. We dissected the anti-IFN functions encoded by viral proteins from those that are essential for viral replication, and systematically identified IFN sensitive mutations on the viral genome. By combining multiple mutations, we generated a live attenuated vaccine candidate: Hyper-Interferon Sensitive (HIS) virus. This approach simultaneously satisfies the requirement for safety, efficacy and production of vaccine (14, 62).

Figure 7A:
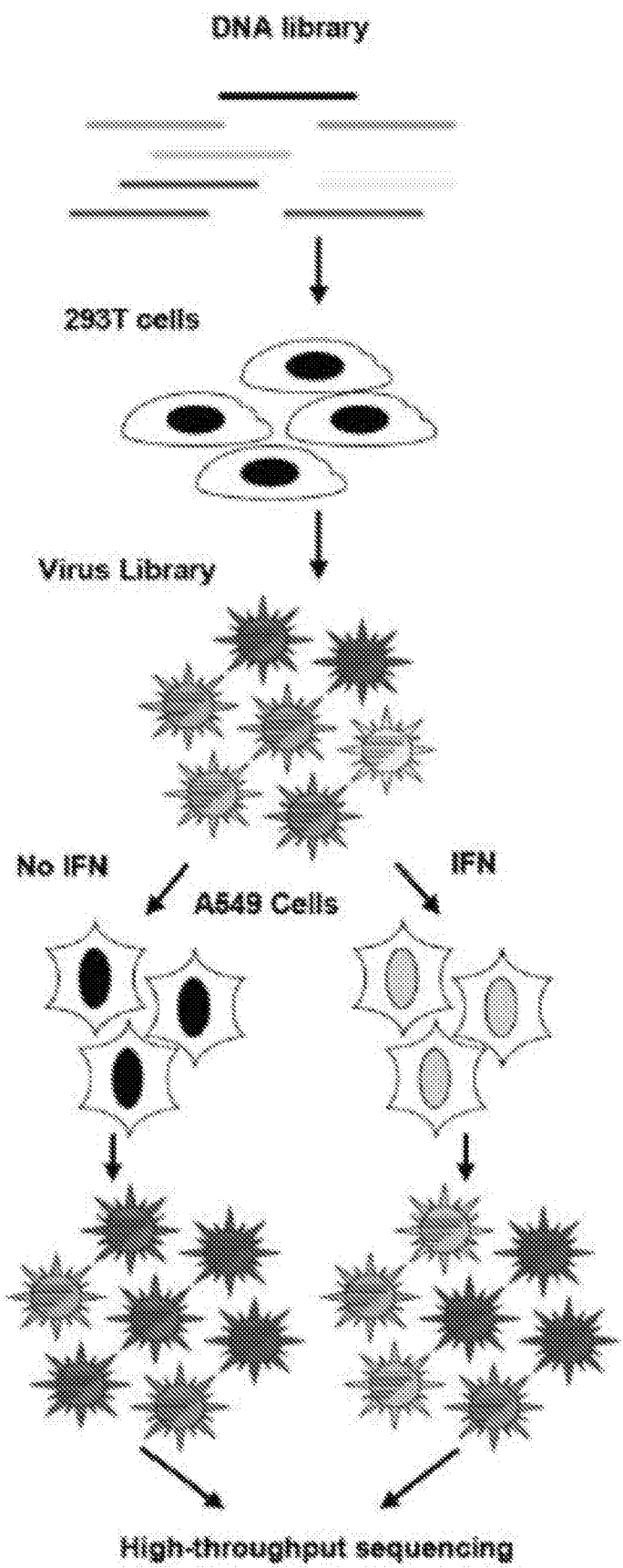
Figure 7B:
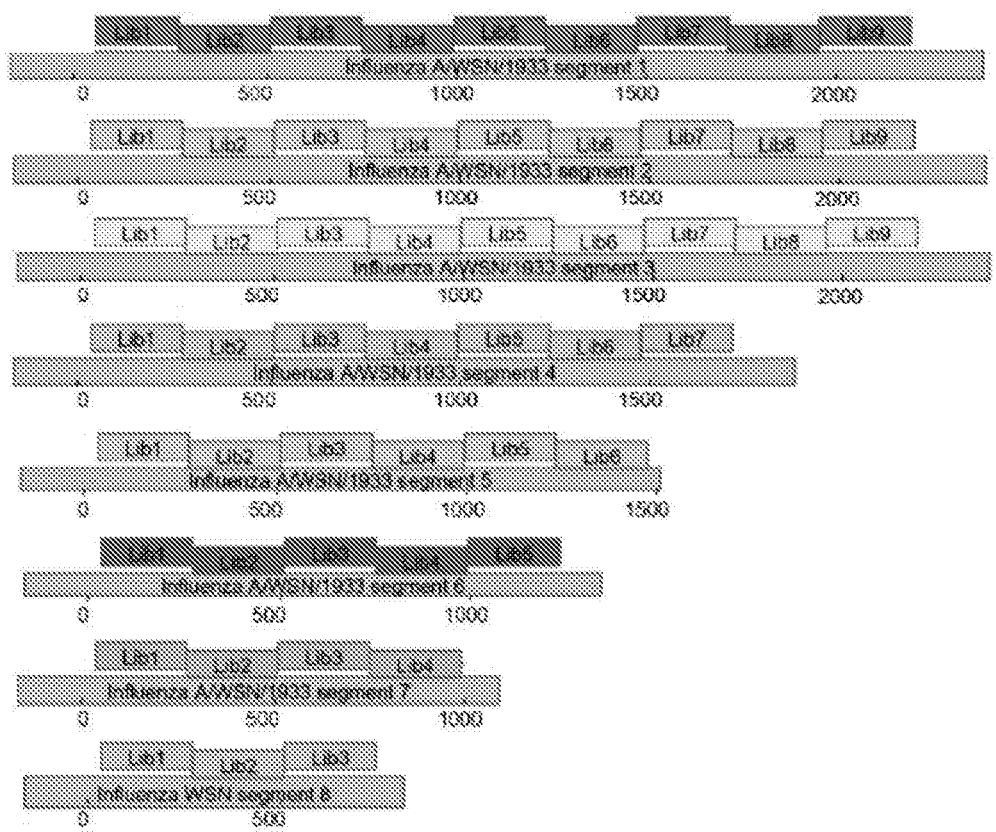
Figure 7C:
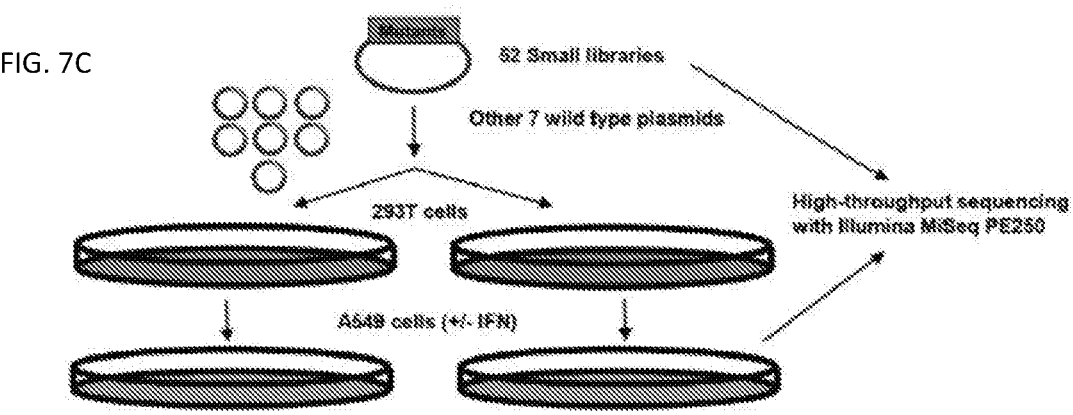

FIG. 7: Construction of single nucleotide mutant libraries across the entire influenza genome (A) A schematic illustration of the quantitative high-throughput genomics system and its utilization to systematically identify IFN-sensitive mutations. (B) The arrangement of 52 plasmid libraries covering the entire influenza A/WSN/33 genome. Each plasmid library was built on a fragment of 240 bp in length and contained ~1000 different point mutations. (C) Schematic illustration for the mutant library reconstitution and selection procedures (19, 36, 37). 30 million 293T cells were transfected with each small plasmid library together with seven other wild type plasmids to reconstitute the mutant virus library. 15 million A549 cells were then infected at an MOI of 0.05 for 24 h to passage the mutant virus library. Biological duplicates were examined for both transfection and infection steps. The mutant plasmid library, mutant viral library after transfection and infection were high-throughput sequenced by Illumina MiSeq with 250 bp paired-end reads.

Figure 8:
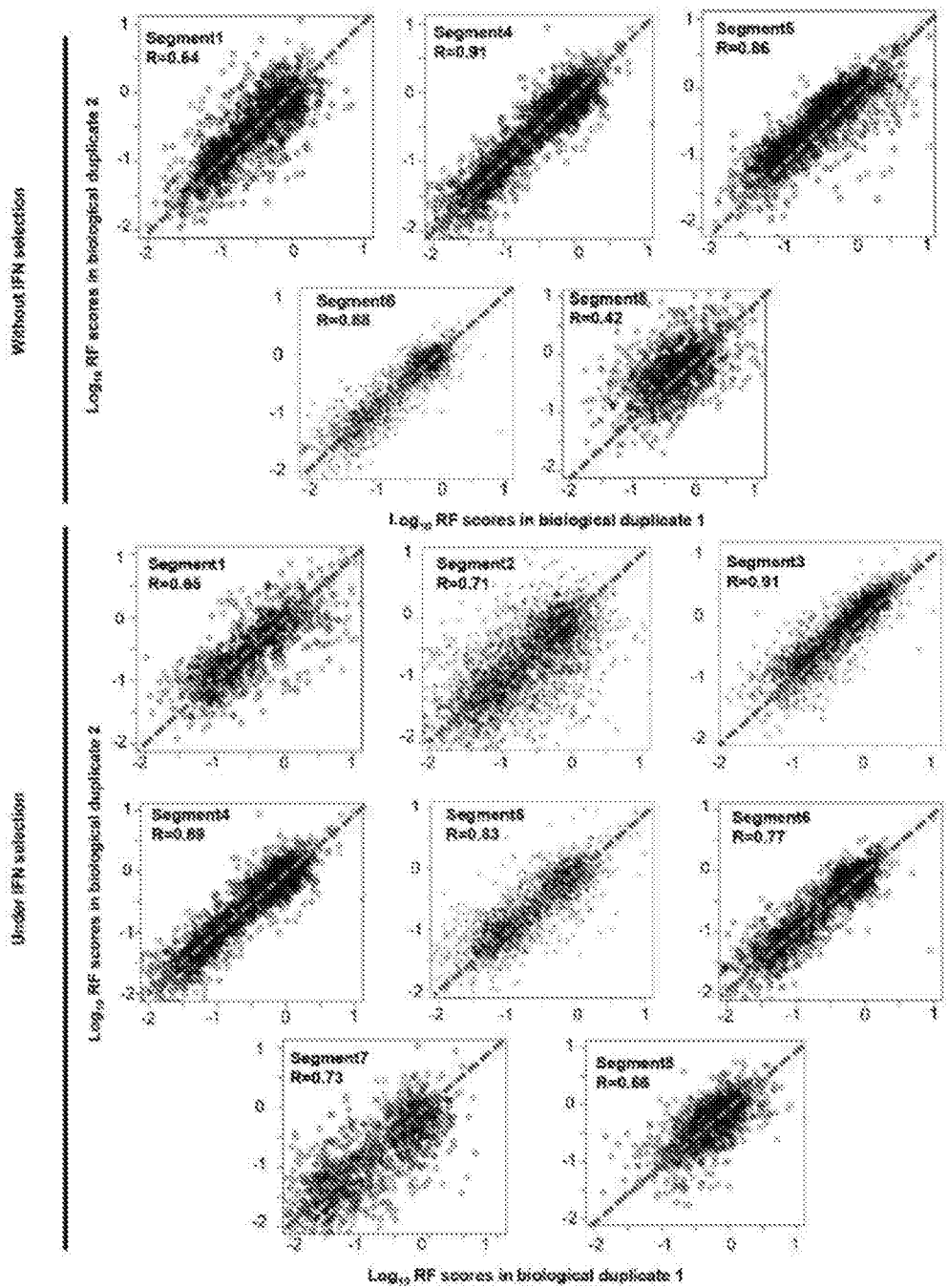

FIG. 8: Correlation of relative fitness scores (RF scores) from independent biological replicates. The correlation between RF scores in biological replicates is shown with scatter plots. Reconstitution and selection of mutant libraries was performed for each viral segment separately. Strong correlation was obtained for the RF scores between biological replicates. Mutant RF scores without IFN selection were reported previously for segment 2, 3 and 7, and were used by this study (21-23). The final RF score for each mutant was calculated as the average between replicates.

FIG. 9: Validations of high-throughput fitness profiling (A) Histograms of the RF scores of synonymous and nonsense mutations. RF scores of synonymous mutations were centered at around 1 (log 10 RF scores centered around 0, mean=−0.08, V=0.27), suggesting that the majority of synonymous mutations were neutral for viral replication. A clear separation of distributions was observed between synonymous and nonsense mutations, suggesting effective selection during passaging of viral mutant libraries. (B) 26 single nucleotide mutations were randomly selected across the genome with a wide range of RF scores. Mutants were reconstructed individually in the context of the whole virus. Relative growth capacities of each mutant were examined by TCID50 assay and compared with RF scores in the fitness profiling. As the TCID50 of 7 mutants was below the detection limit (plotted as 0 in linear scale), scatter plots are shown in both linear (left) and log (right) scales. The relative growth of individually reconstructed mutant viruses correlated well with the fitness profiling data.

Figure 10:
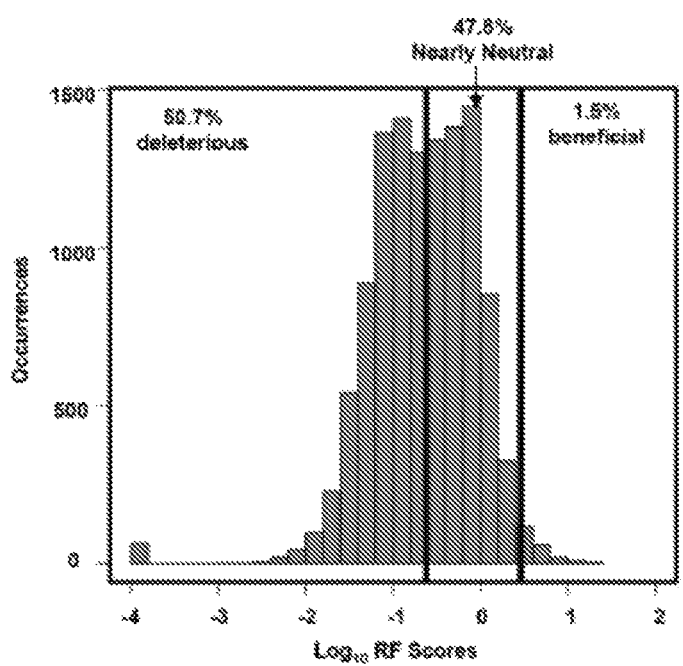

FIG. 10: Fitness distribution of missense mutations. Distribution of fitness effect (DFE) for all single nucleotide missense mutations is shown. Using synonymous mutations as bench mark, we designated a mutation to be deleterious if the RF score <mean-2V, beneficial if the RF score >mean+2V, and nearly neutral if within. Across the entire viral genome, around 50.7% missense mutations are deleterious and only 1.5% are beneficial.

Figure 1A:
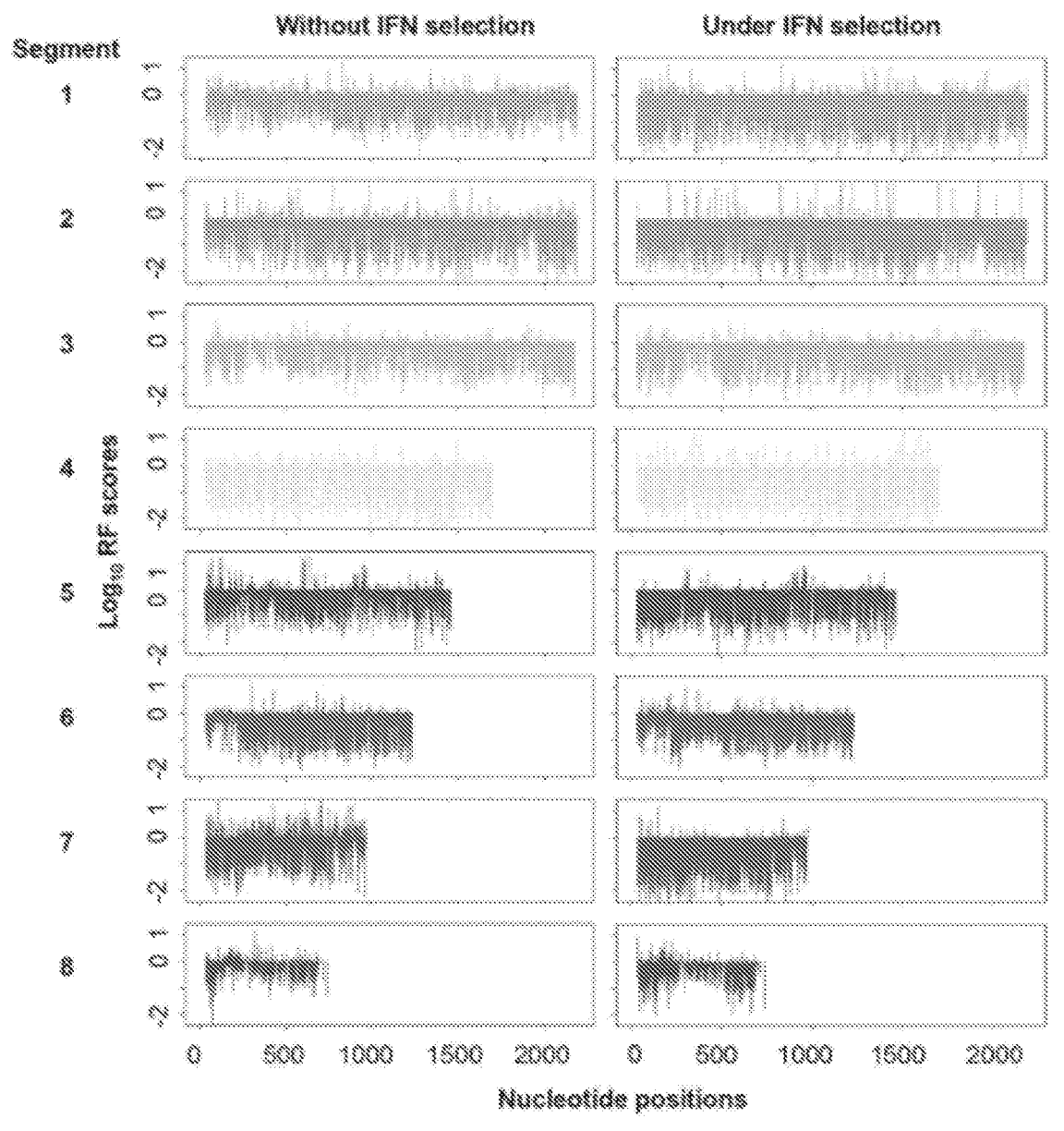
Figure 11:
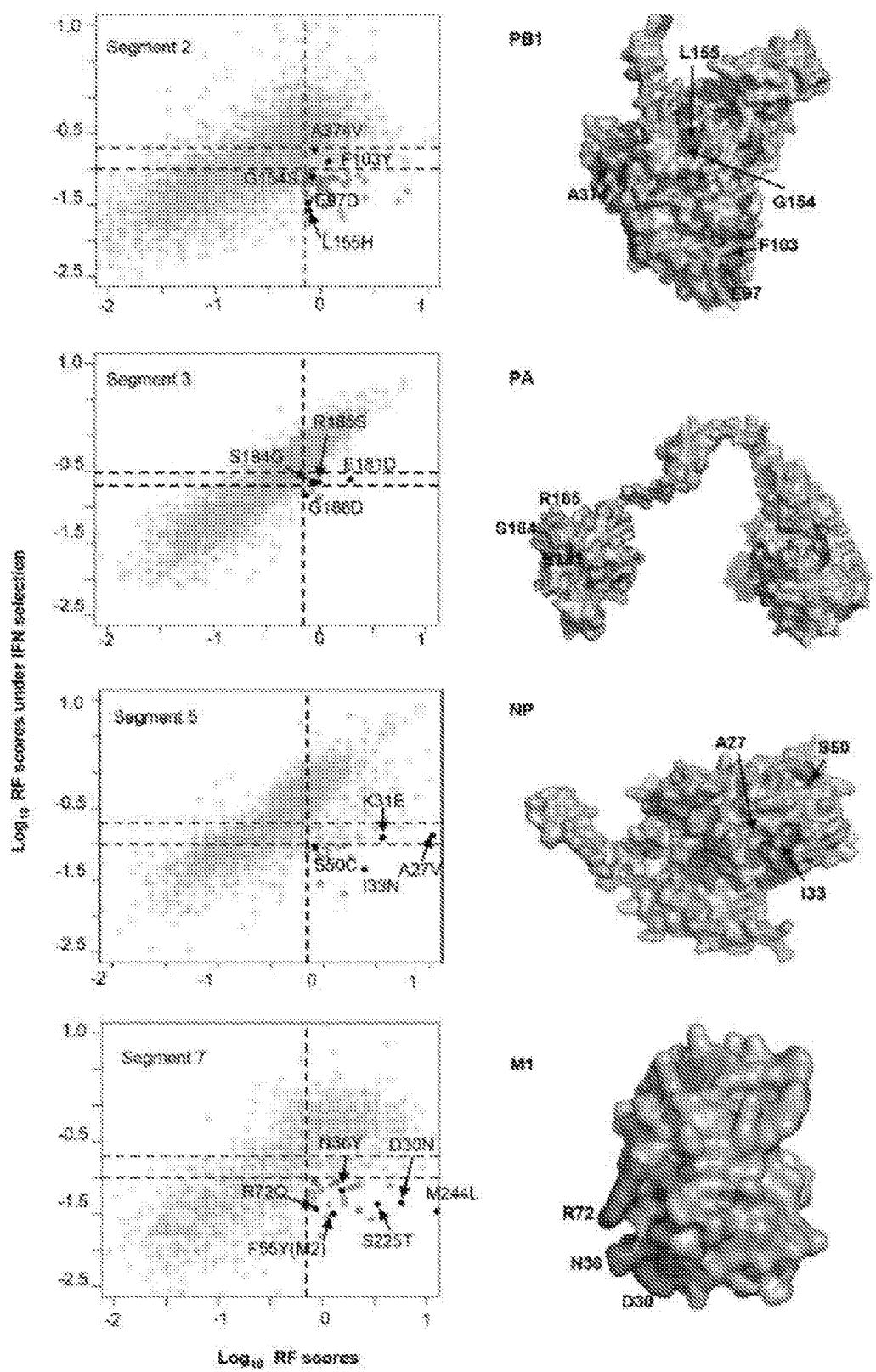
Figure 12B:
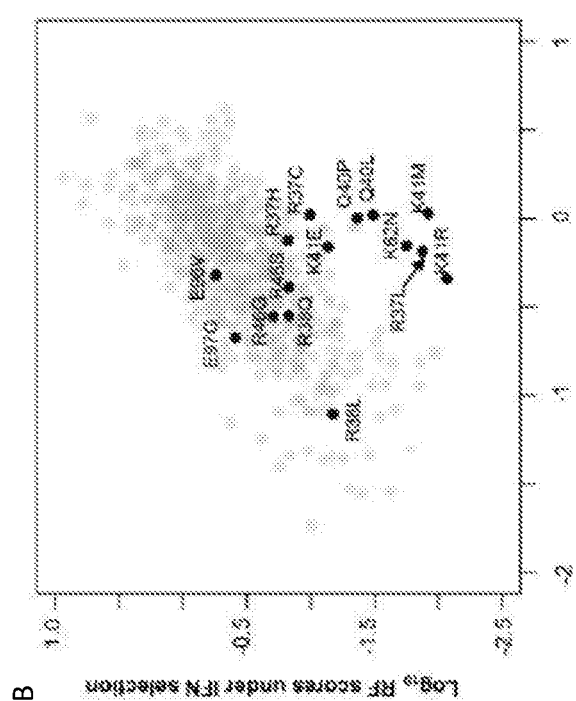
Figure 12D:
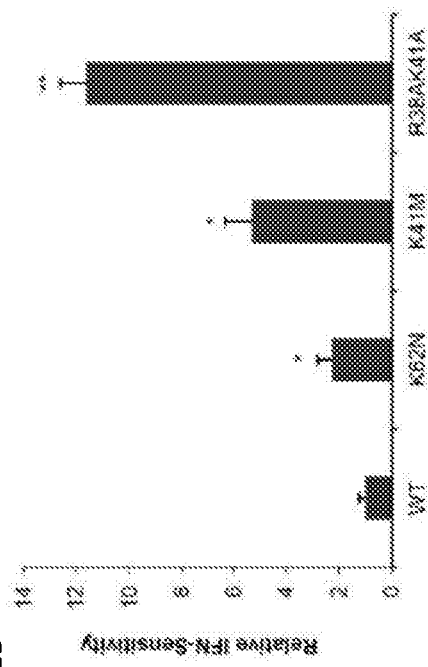
Figure 12A:
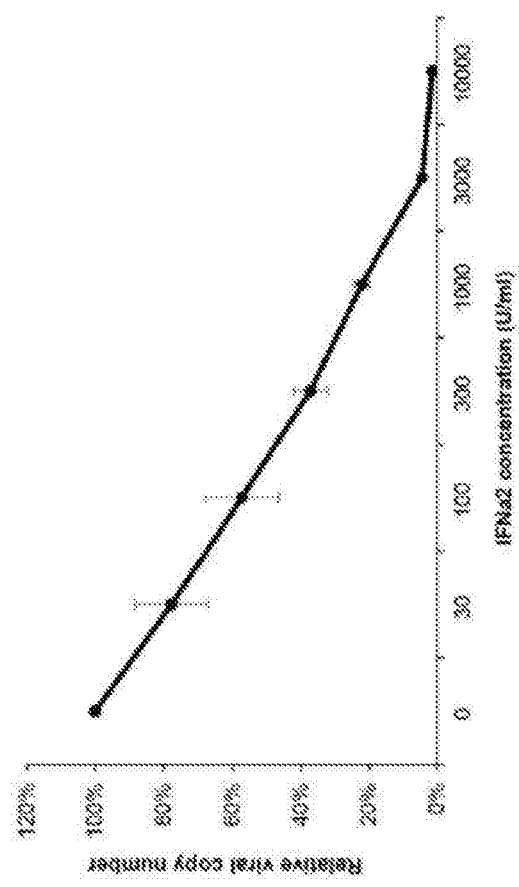
Figure 12C:
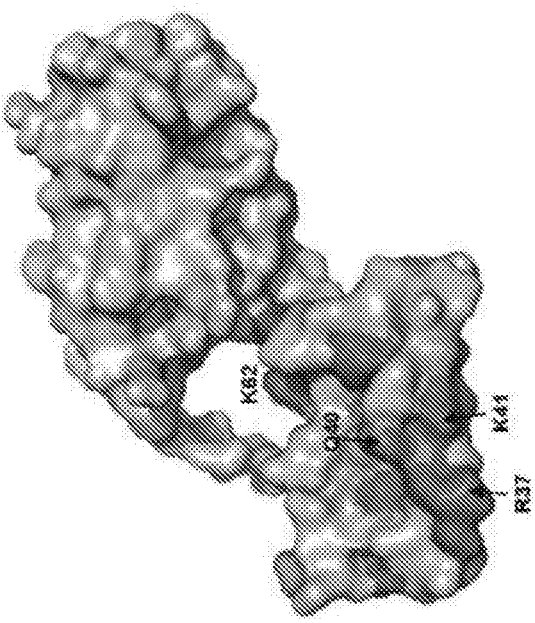

FIG. 11: Identification of potential IFN sensitive mutations. Selection of possible IFN sensitive mutations for validation is shown on PB1, PA, NP and M1. Mutations on PB2 and NS1 are shown in FIG. 1C and S7. The focus is on non-surface virion proteins (PB2, PB1, PA, NP, M1 and M2), because HA and NA are highly variable and NS1 has been extensively studied (16, 63-66). Putative IFN sensitive mutations are highlighted with orange and red colors. Orange for segment 2, 5 and 7: mutations with RF scores >0.7 without IFN and <0.2 with IFN selection; Red for segment 2, 5 and 7: mutations with RF scores >0.7 without IFN and <0.1 with IFN selection. Orange for segment 3: mutations with RF scores >0.7 without IFN and <0.3 with IFN selection; Red for segment 3: mutations with RF scores >0.7 without IFN and <0.2 with IFN selection. The corresponding residues were mapped onto protein structures (PDB: 4WSB, 2IQH &1EA3) with the same colors (38-40, 48-50). We preferentially chose the IFN-sensitive mutations that are clustered on the protein surface for validation. Up to 7 mutations per segment were selected for experimental validations.

FIG. 12: Establishing conditions for interferon selection of mutant viral libraries (A) Dose response curve of type I IFN (IFN-D2) on WT WSN viral replication was measured. A549 cells were pre-treated with different doses of IFN-D2 for 20 h, and infected with WT virus at an MOI of 0.1. Cells were washed twice with PBS at 2 h post-infection and equal concentrations of IFN-D2 was supplied to the cells. Supernatants were collected at 24 h post-infection and viral copy numbers were measured by real-time PCR. 1000 U/ml IFN-D2 was selected as the concentration for screening, which is at IC80. (B) Known residues of NS1 protein that have a functional role in interfering with IFN pathway and their corresponding mutations were labeled (26, 27, 67). We identified R37, Q40, K41, R46 and K62 in the RNA binding domain to be key residues interfering with IFN function. However, some mutations at residues that have known anti-IFN function (such as R38, E96 and E97), were not identified as top IFN-sensitive mutations, indicating the existence of false negatives in our screening results. (C) Putative IFN sensitive mutations identified on NS1 were highlighted with orange and red colors (PDB: 4OPH) (68). Orange: mutations with RF scores >0.7 without IFN and <0.3 with IFN selection; Red: mutations with RF scores >0.7 without IFN and <0.2 with IFN selection. (D) Profiling results were validated with individual constructed mutant viruses on NS1. A previously reported double mutation (R38A/K41A) was used as the positive control. Error bars denote SD. *P<0.05, P<0.01, *P<0.001 (two-tailed t-test compared with WT).

FIG. 13: Validation of IFN-sensitivity with individual mutant viruses (A) Viral replication capacity of selected IFN sensitive mutants. Viruses were reconstituted by co-transfecting plasmid containing the single mutation together with 7 plasmids encoding other wild type proteins. A549 cells were infected with the indicated mutant at an MOI of 0.1. Supernatants were collected at 24 h post-infection and the viral titer was measured by TCID50 assay. All the mutants were neutral or nearly neutral for viral replication (N=2). (B) Relative polymerase activity for single mutations in the polymerase complex proteins (N=3). Most mutants showed nearly intact polymerase activity. Error bars denote SD.

FIG. 14: Induction of IFN production by IFN sensitive mutants in vitro (A) The induction of IFN-E expression is more significant for cells pre-treated with IFN. A549 cells were pretreated with 1000 U/ml IFN-D2 for 20 h or un-treated before infection. Cells were then infected with WT or indicated mutants at an MOI of 1. RNAs were extracted at 6 h post-infection. IFN-E gene expression was quantified by real-time PCR and calculated as fold of induction compared with WT infected cells (N=3). Error bars denote SD. *P<0.05, P<0.01, *P<0.001 (two-tailed t-test). (B&C). Induction of ISG54 expression is shown for WT and indicated mutants (N=3). A549 cells were infected at an MOI of 1. RNAs were extracted at 6 h post-infection. ISG54 gene expression was quantified by real-time PCR and shown as fold of induction normalized to mock infected cells (Ctl, B) or actual CT number (C) (69). Error bars denote SD. *P<0.05, P<0.01, *P<0.001 (two-tailed t-test compared with Ctl).

FIG. 15: Nuclear translocation of IRF3 upon infection with WT or indicated mutants was examined by immunofluorescence analysis. A549 cells were infected at an MOI of 1. Cells were fixed and subjected to immunofluorescence analysis (IFA) at 8 h post-infection with antibodies against IRF3 protein. The three mutations on PB2 (N9D, Q75H, T76A) and three mutations on M1 (N36Y, R72Q, S225T), but not WT, showed clear nuclear localization of IRF3, indicating their functional interactions with IFN pathway upstream of IRF3.

FIG. 16: MAVS is required for the high induction of IFN-E by PB2 and M1 mutants. Induction of ISG54 expression was examined in STING or MAVS knockout THP1 cells. THP1 cells stably overexpressing Cas9 protein were used as a control. Cells were infected with WT or the indicated mutants at an MOI of 1 and RNAs were extracted at 6 h post-infection. ISG54 gene expression was quantified by real-time PCR and calculated as fold of induction normalized to WT infected cells (N=3). Error bars denote SD. *P<0.05, P<0.01, *P<0.001 (two-tailed t-test compared with WT infection of corresponding cell types).

FIG. 17: Induction of IFN production by HIS virus (A) Induction of IFN-β expression by indicated virus in A549 cells at 6 h post-infection, with mock infection as Ctl (N=3). Actual CT number were shown for real-time PCR analysis. (B) Induction of IFN-E expression was examined at 1 h, 2 h and 4 h post-infection with WT, NS1 mutant or HIS viruses (N=3). (C) Induction of indicated ISG expression. THP1 cells were infected with WT or HIS virus at an MOI of 0.1. RNAs were extracted at 24 h post-infection. Gene expression was quantified by real-time PCR and calculated as fold of induction compared with mock infected cells (N=3). (D) Average reads per million (RPM) for indicated viral segments in A549 cells (N=2) as quantified by RNA sequencing. (E) Cell viability upon infection with the indicated virus. A549 cells were infected with indicated virus at an MOI of 0.1 for 72 h in 96-well plates. Cell viability was examined by CCK8 assay (N=3). (F&G) Relative IFN-sensitivity (F) and IFN-E induction (G) were examined for HIS virus in PR8 background (N=3). The same eight mutations (PB2: N9D, Q75H, T76A, M1: N36Y, R72Q, S225T, NS1: R38A, K41A) were introduced into PR8 through reverse genetic system. HIS virus in PR8 background showed higher IFN-sensitivity and IFN-E induction compared with WT PR8 or NS1 mutant (R38A/K41A). Error bars denote SD for all panels. *P<0.05, P<0.01, *P<0.001 (one-way analysis of variance (ANOVA) with Bonferroni multiple-comparisons test).

FIG. 18: Characterization of cold-adapted (CA) virus in WSN strain, WSN-CA (A) Viral titers assessed under different temperatures are shown for WT and WSN-CA virus. A549 cells were infected with the indicated virus at an MOI of 0.1, and supernatant was collected at 72 h post-infection. Viral titer was determined by TCID50 assay (N=3). (B) Induction of IFN-β expression in A549 cells infected with WT or indicated mutants was examined by real-time PCR with mock infection as control (Ctl) (N=3). Error bars denote SD for all panels. *P<0.05, P<0.01, *P<0.001 (two-tailed t-test for panel A and one-way analysis of variance (ANOVA) with Bonferroni multiple-comparisons test for panel B).

FIG. 19: Replication of HIS virus and induction of cytokines in IFN competent mice (A&B) Viral titers in lung tissues are shown for the indicated viruses as relative copy number. Female BALB/c mice at the age of 6-8 weeks were intranasally infected with 1×104 TCID50 of the indicated virus. Lung tissues were harvested at day 2 post-infection (N=3). Viral copy numbers were examined by real-time PCR and normalized to WT infected mice. Dashed line represents the detection limit. (C) HE staining of lung tissues at day 2 post-infection. (D) Epithelial integrity was examined by albumin concentration in mouse BAL samples collected at day 2 post-infection (N=4). WT infected mice showed a significantly higher albumin concentration than HIS or mock infected mice, with no-significant loss of lung integrity caused by HIS. (E&F) BAL cytospins are shown for WT or HIS infected mice at day 2 post-infection as percentage (E) and number (F) of indicated cell types (N=4). (G&H) Pathology scores were quantified for lungs on HE staining slides, at day 2 post-infection (G) and day 9 (H) post-infection. 4-5 areas were averaged for each mouse (N=4). (I) BAL cytospins are shown for WT or HIS infected mice at day 9 post-infection as number of indicated cell types (N=3). (J) Induction of indicated cytokines was examined with Luminex multiplex assay with BAL samples collected at day 2 post-infection (N=4). The concentration of each cytokine in WT, HIS or mick infected mice BAL samples is shown. (K) IFN-D concentration in BAL samples were determined using VeriKine Mouse Interferon Alpha ELISA kit at day 2 post-infection (N=4). Error bars denote SD for all panels. *P<0.05, P<0.01, *P<0.001 (one-way analysis of variance (ANOVA) with Bonferroni multiple-comparisons test for panel A, two-tailed t-test for panel B, D-F, I&J, Mann-Whitney U test for panel G&H).

FIG. 20: Antibody response induced by HIS vaccination. (A) Neutralizing antibodies in sera of vaccinated mice. Female BALB/c mice at the age of 6-8 weeks were intranasally infected with 1×104 TCID50 of the indicated virus (N=4). Sera were obtained at day 28 post-infection and heat inactivated for neutralization antibody assay. (B&C) HA-specific IgG and HA neutralizing antibodies were examined for sera of vaccinated mice at indicated time points by ELISA (B) and hemagglutination inhibition (HAI) assay (C) (N=3). HA proteins from four different viral strains were purified and used as targets for IgG binding: WSN/H1, PR8/H1, HK68/H3 and Viet04/H5 (60). WT and HIS infected mice elicited antibody response against other strains within the same HA group (PR8/H1, Viet04/H5) but not across different HA group (HK68/H3). Similar to the WT vaccinated group, the HA antibody titer in HIS immunized mice increased steadily from days 14, 21 to 28 post-vaccination. (D) HA neutralizing antibodies in sera of vaccinated mice were examined at 21 days post-infection by HAI assay (N=3). HIS induced higher levels of HA neutralizing antibodies than inactivated WT or inactivated HIS viruses. (E) M1 specific IgG antibody was examined in mouse sera at day 28 post-infection by ELISA (N=4). (F) NP specific IgA antibody was examined in BAL samples at day 28 post-infection by ELISA (N=4). (G) HA neutralizing antibodies in sera of vaccinated ferrets were examined at 15, 22 and 50 days post-infection by HAI assay (N=3). The antibody response induced by HIS is stable and long-lasting. Error bars denote SD for all panels. *P<0.05, P<0.01, *P<0.001 (one-way analysis of variance (ANOVA) with Bonferroni multiple-comparisons test for panel D&E, two-tailed t-test for panel C).

Figures 21A, 21B, 21C:
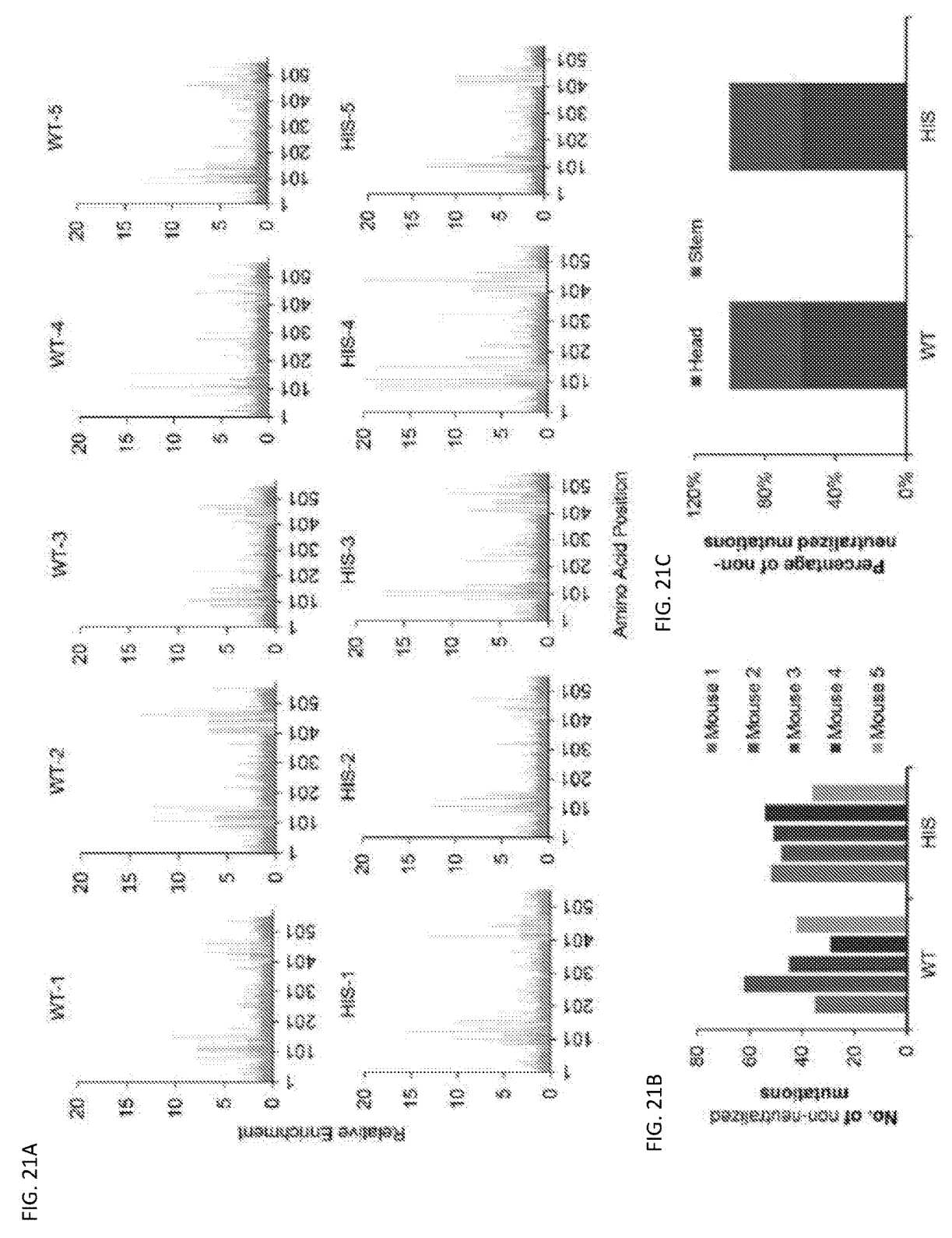

FIG. 21: Mutant viruses non-neutralized by sera of vaccinated mice were profiled with HA mutant library (A) Relative enrichment scores (RE scores) of HA point mutations under selection with indicated mouse serum are shown across the amino acid positions of the HA protein. HA single nucleotide mutant libraries were selected under sera of WT or HIS vaccinated mice (N=5) at the concentration of IC80. Sera from mock infected mice were used as control. RE score of each mutant was calculated as the relative fitness under serum selection compared with the control. (B) Numbers of non-neutralized mutations are shown for each mouse, suggesting similar diversity of antibody responses in different mice. Non-neutralized mutations were defined as the ones with RE score >5 for each condition and with RF scores >0.05. (C) Percentage of non-neutralized mutations located in the head and stem region of HA proteins is shown. 51 and 61 non-neutralized mutations were identified with more than one serum selection, in WT and HIS vaccinated groups respectively (N=5). ~60% of these mutations are located in the head domain of the HA protein, while ~40% of them are in the stem region. The percentage is similar between the two groups.

FIG. 22: Robust T cell response induced by HIS virus (A) CD8 T cell responses were examined by tetramer staining and flow cytometry. Representative flow cytometry dot plots are shown for lung and spleen samples. Upper-right quadrants indicate portion of NP epitope specific CD8 T cells, which are positive for CD3, CD8 and NP366-374 tetramer. (B) NP specific CD8 T cells in mouse lung tissues were examined by tetramer staining and flow cytometry. (C&D) Number of viral antigen-specific CD8 T cells in mouse spleen (C) and lung (D) tissues induced by indicated virus were examined by flow cytometry using tetramers against NP or PB1 (N=10). (E) Functionality of CD8 T cell responses was examined by peptide stimulation and intracellular IFN-J staining of splenocytes at day 28 post-vaccination. Percentages of IFN-J positive CD8 T cells was quantified for indicated viral peptide from PA, PB2 and NP (N=3). (F) Percentage of antigen specific short lived effector cells (SLEC) in mouse lung and spleen tissues were examined by flow cytometry using Tetramer+ $CD127^{low}KLRG1^{high}$ as the markers (N=3). (G) Percentage of antigen specific central memory like CD8 T cells in mouse lung and spleen tissues were examined by flow cytometry using Tetramer+CD44+CD62L+CCR7+ as the markers (N=3). (H) Percentage of antigen specific effector memory like CD8 T cells in mouse lung and spleen tissues were examined by flow cytometry using Tetramer+CD44+CD62L–CCR7– as the markers (N=3). (I) Number of NP antigen specific CD8 T cells during secondary responses were examined in lung tissues from mice vaccinated with the indicated viruses (N=4). Error bars denote SD for all panels. *P<0.05, P<0.01, *P<0.001 (one-way analysis of variance (ANOVA) with Bonferroni multiple-comparisons test for panel B, C, D&I, two-tailed t-test for panel E-H).

FIG. 23: Diversity of T cell responses induced by HIS virus (A&B) TCR VE gene usage was analyzed for NP specific CD8 T cells during the primary (A) and the secondary (B) response in HIS or WT infected mice. Deep sequencing was performed for TCRE loci of influenza NP366-374 specific CD8 T cells. For the primary response, mouse lung and spleen tissues were harvested at day 10 post-infection. For the secondary response, vaccinated mice were challenged with WT virus at day 28 post-infection, and tissues were harvested at day 10 post-challenge. NP specific T cells were sorted out by FACS and genomic DNA was extracted for deep sequencing. Error bars denote SE. (C&D) Overlapping rates of T cell lineages identified through CDR3 rearrangements are shown between different mice for the primary (C) and the secondary (D) response. For the primary responses, the CDR3 rearrangement is diverse among different mice, as shown with low overlap between or within WT and HIS vaccinated groups. However, the rearrangement converged within groups for the secondary responses, as shown with a significantly more overlap within the same vaccination group comparing between groups (two tailed t-test, p=0.00008).

FIG. 24: Protection of HIS vaccinated mice from viral challenges (A) Protection of vaccinated mice from WT infection was quantified by relative viral copy number in lung tissues. Female BALB/c mice at the age of 6-8 weeks were intranasally vaccinated with $1×10^4$ TCID50 of indicated virus (N=4). Mice were challenged with $1×10^4$ TCID50 of WT virus at day 28 post vaccination. Lung tissues were extracted at day 2 post challenge. Viral copy number was quantified by real-time PCR and normalized to WT vaccinated mice. Dashed line represents the detection limit. (B) Protection efficiency of HIS vaccinated mice from WT infection was examined with a high dose vaccination or double vaccinations. DV: double vaccination with 1×104 TCID50HIS virus at 28 days apart; HD: high dose vaccination with HIS virus at 1×106 TCID50. Mice were challenged with 1×104 TCID50 of WT virus and viral growth was quantified by real-time PCR in lung tissues at day 2 post-challenge. Dashed line represents the detection limit (N=4). (C) Protection of vaccinated mice from WT PR8 infection was quantified by relative viral copy number in lung tissues. Dashed line represents the detection limit (N=4). (D) Clinical scores of mice challenged with homologous and heterologous viral strains. HIS vaccinated or mock (PBS) vaccinated C57/B6 mice were challenged with A/WSN/33 (H1N1), A/PR8/34 (H1N1) and A/Cal/04/09 (H1N1) at a dose of LD90 and A/X-31 (H3N2) at LD50 (N=10). Clinical scores were obtained twice daily for 10 days. (E) Protection of HIS vaccinated ferrets from A/California/07/09 virus challenge is shown with percentage of body weight loss (N=2). Female ferrets at the age between four to six months were vaccinated with HIS or PBS (Ctl). At day 35 post-vaccination, ferrets were challenged with 1×106 TCID50 of A/California/07/09 virus. Clinical scores were obtained twice daily for 10 days. *P<0.05, P<0.01, *P<0.001 (one-way analysis of variance (ANOVA) with Bonferroni multiple-comparisons test). Error bars denote SD for all panels.

Figure 25:
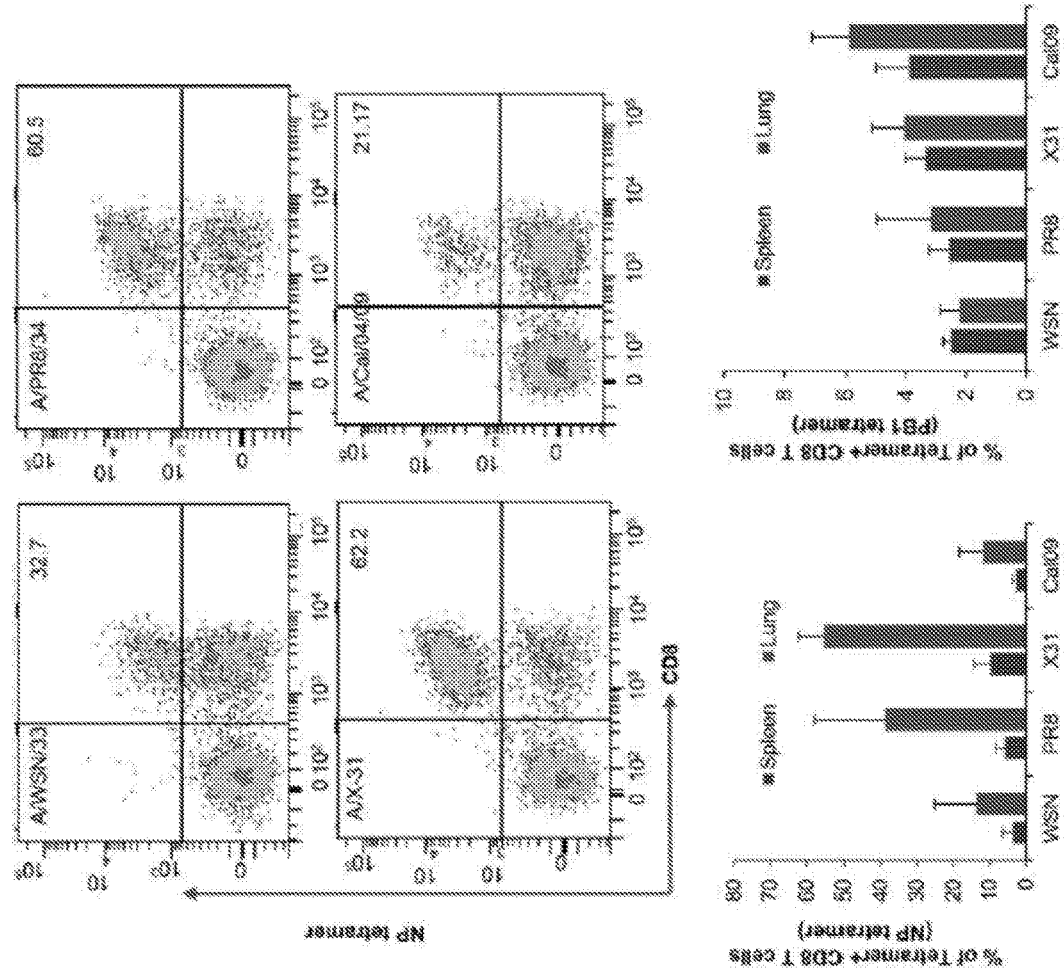

FIG. 25: Secondary T cell responses post viral challenges. The secondary T cell responses were examined by tetramer staining and flow cytometry. HIS vaccinated mice were challenged with A/WSN/33, A/PR8/34, A/Cal/04/09 or A/X-31 at day 28 post-vaccination. 14 days after challenge, lung and spleen samples were collected from vaccinated mice from each challenge group (N=5). Antigen specific CD8 T cells against H-2Db influenza A virus NP366-374 (NPP, ASNENME™) and H-2Kb influenza A virus PB1703-711 (SSYRRPVGI) were examined. Robust CD8 T cell rebound response against NP epitope was observed in all challenge groups.

Figure 26:
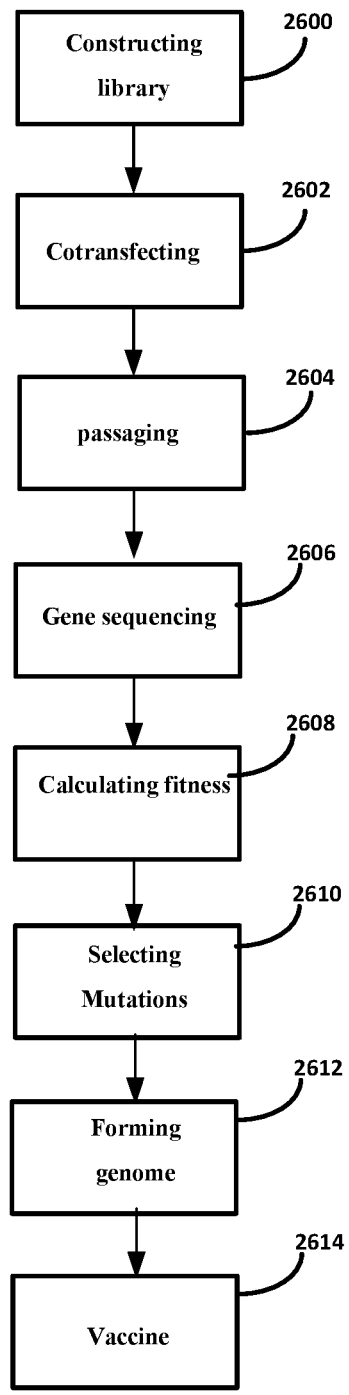

FIG. 26 is a flowchart illustrating a method of making a genome using a genetic platform.

Figure 27:
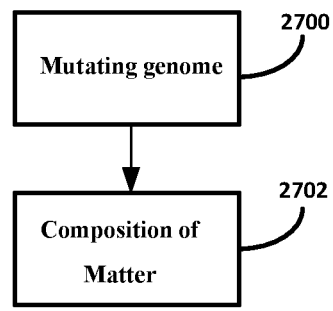

FIG. 27 is a flowchart illustrating a method of making a composition of matter.

DETAILED DESCRIPTION OF THE INVENTION

In the detailed description of the invention, reference may be made to the accompanying drawings which form a part hereof, and in which is shown by way of illustration specific embodiments in which the invention may be practiced. It is to be understood that other embodiments may be utilized and structural changes may be made without departing from the scope of the present invention. A number of different publications are also referenced herein as indicated throughout the specification. A list of these different publications can be found below in the section entitled "REFERENCES". All publications, patents, and patent applications cited herein (e.g. Simultaneous and complete genome sequencing of influenza A and B with high coverage by Illumina MiSeq Platform" Journal of Virological Methods, Volume 193, Issue 2, November 2013, Pages 394-404) are hereby incorporated by reference in their entirety for all purposes.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

Embodiments of the present invention describe a surprisingly different and radical way for developing live attenuated vaccines: controlling a combination of interferon sensitive mutations in the vaccine so as to fine-tune a replication/immune response tradeoff that achieves the best or desirable efficiency with sufficient safety. On one hand the interferon sensitivity attenuates the virus in vivo. On the other hand, the ability to induce higher interferon response induces a higher and more effective adaptive immune response.

Further aspects and embodiments of the invention are disclosed in the following examples.

Example: Influenza A Virus

The present disclosure describes the establishment of a high throughput genetic platform to examine the fitness effect of single mutations across the entire influenza genome.

To tackle the challenges described herein, we developed a quantitative high-throughput genomics system, which combines saturation mutagenesis and next-generation sequencing, to comprehensively identify IFN-modulating functions in the entire viral genome (18). This system has enabled us to quantitatively measure the replication capacity of a large number of mutants in parallel under specific conditions (18, 19). We performed comparative profiling of the entire influenza genome with and without IFN selection, which led to the identification of IFN-modulating functions on multiple viral segments. By combining eight IFN-sensitive mutations across the viral genome, we generated a hyper-interferon-sensitive (HIS) virus that is replication-competent in vitro but highly attenuated in IFN-competent hosts in vivo. The HIS virus showed desired properties as a safe and effective live attenuated influenza vaccine with robust humoral and cellular responses, and it provided broad protection against homologous and heterologous viral challenges in mice and ferrets.

Compared with previous methods, we significantly improved the quality and reproducibility, getting rid of the noise from multiple mutations. Moreover, to our knowledge, the genetic profiling system described herein is the first whole genome fitness profile for the influenza virus.

a. Fitness Profile of the Influenza a Viral Genome at Single-Nucleotide Resolution An eight-plasmid reverse genetic system carrying the influenza A/WSN/33 (H1N1) virus genome was used for the construction of mutant plasmid libraries (20). The mutants were divided into 52 sublibraries, each of which contained single-nucleotide mutations in a small genome region of 240 base pairs that were generated by error-prone polymerase chain reaction (FIG. 7A) (21-23). Viral mutant libraries were reconstituted in human embryonic kidney 293T cells by cotransfecting the plasmid encoding the sublibrary of mutants with the other seven plasmids encoding wild-type (WT) viral proteins. To systematically identify IFN-modulating functions, all viral libraries were selected in A549 cells with or without exogenous IFN treatment (IFN-α2 at inhibitory concentration 80) (19). Illumina sequencing was used to identify each mutant and to calculate the corresponding frequency within each sublibrary. The relative fitness (RF) score of a mutant virus was calculated as the ratio of the relative frequency in the selected virus library to that in the plasmid library (FIG. 1A). There were strong correlations between biological duplicates of transfection and of selection (FIG. 8). We observed a clear separation of the distribution of fitness effects between synonymous mutations and nonsense mutations (FIG. 9A), indicating effective selection on virus mutants. To further validate the accuracy of the fitness profiling, we randomly selected 26 missense mutations and characterized the corresponding mutant viruses individually. The replication capacity of each mutant was highly correlated with the RF scores from the fitness profiling (FIG. 9B). Using synonymous mutations as a benchmark, 50.7% of missense mutations across the whole genome were deleterious, in accordance with previous findings that single mutations are poorly tolerated in the genomes of RNA viruses (FIG. 10A) (24, 25).

b. Systematic Identification of IFN-Sensitive Mutations

Figure 1B:
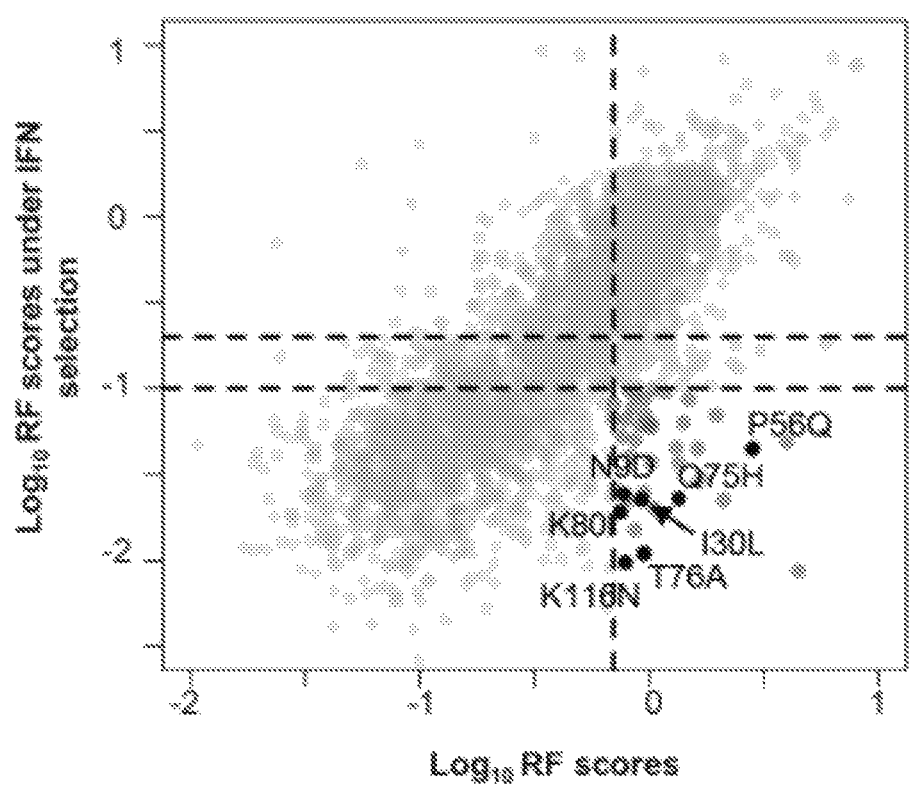
FIG. 1 Identification of IFN-sensitive mutations using quantitative high-throughput genomics. (A) Relative fitness (RF) scores for individual mutations in A549 cells with (right) and without (left) IFN selection across the influenza A/WSN/33 genome. (B and C) Identification of IFN-sensitive mutations with PB2 protein as an example [Protein Data Bank (PDB) ID, 4WSB] (38, 39). Red and orange represent strong and intermediate IFN sensitivity, respectively. (D) Validation of IFN sensitivity with individually reconstituted mutants (n=4). The top eight mutations on nonsurface virion proteins are shown in black. (E) Induction of IFN-β expression in A549 cells infected with WT virus or indicated mutants at 6 hours post-infection, with mock infection as control (Ctl) (n=3). Error bars, SD. *$P<0.05$, **$P<0.01$ [two-tailed t test compared with WT (D) or with Ctl (E)]. Single-letter abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.
Figure 1C:
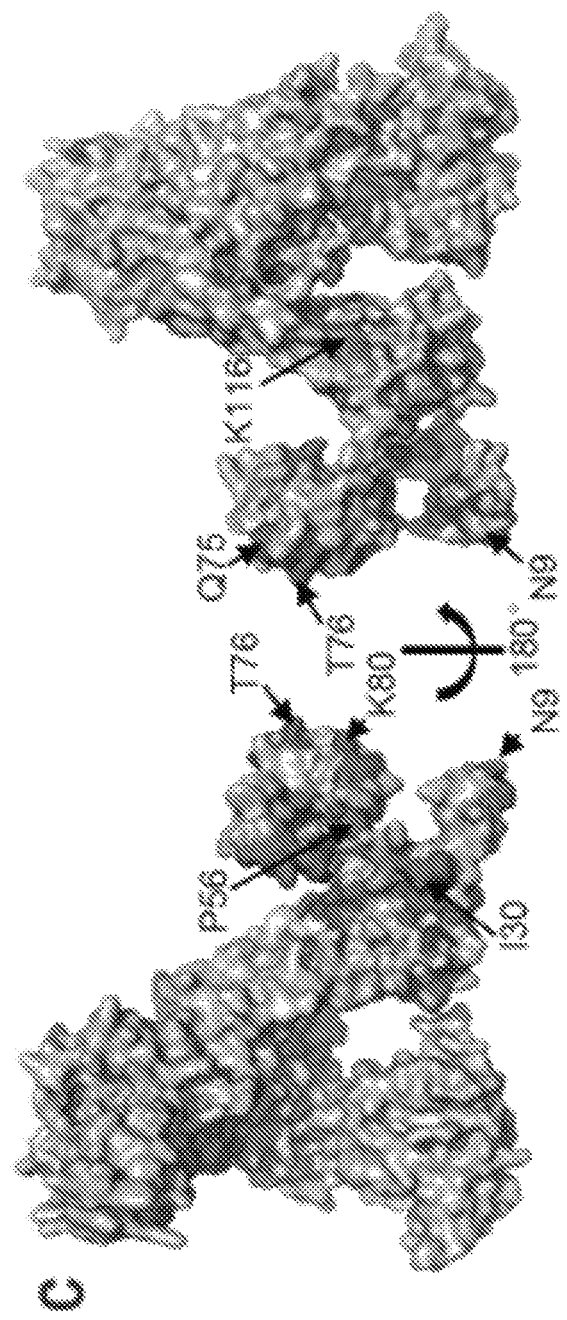
Figure 1D:
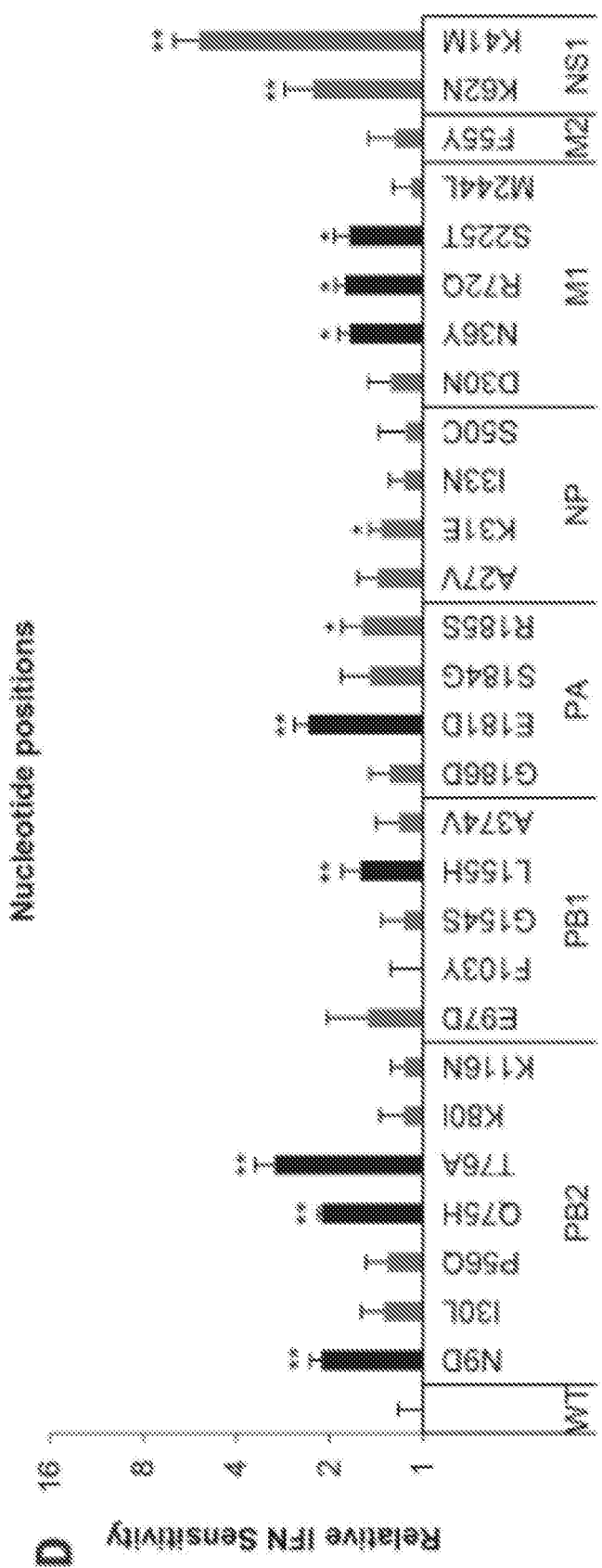
Figure 1E:
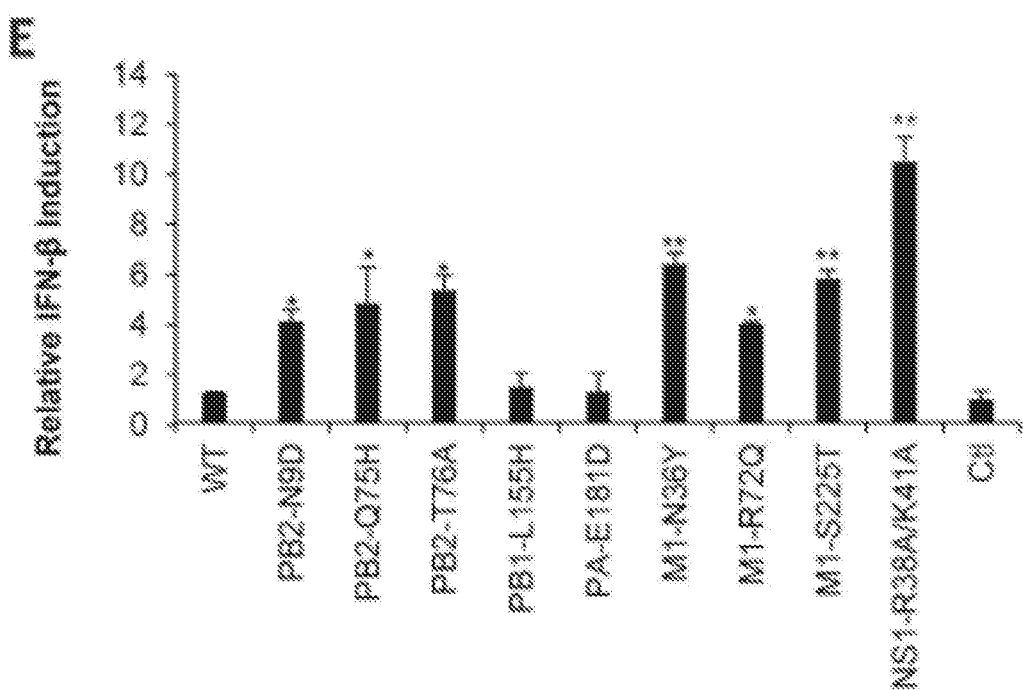
Figure 13A:
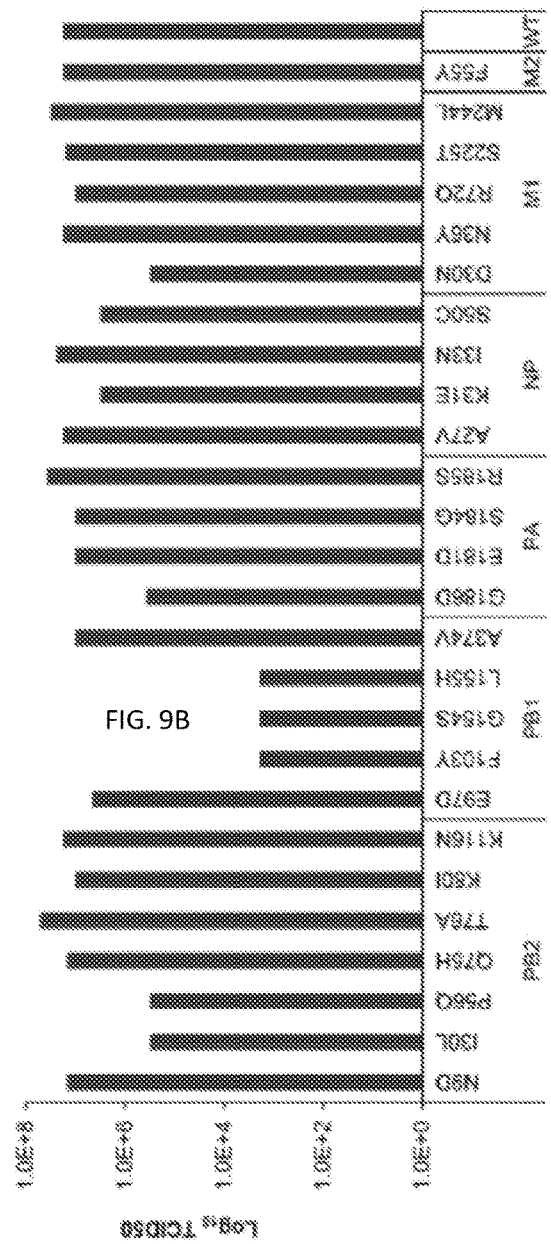
Figure 13B:
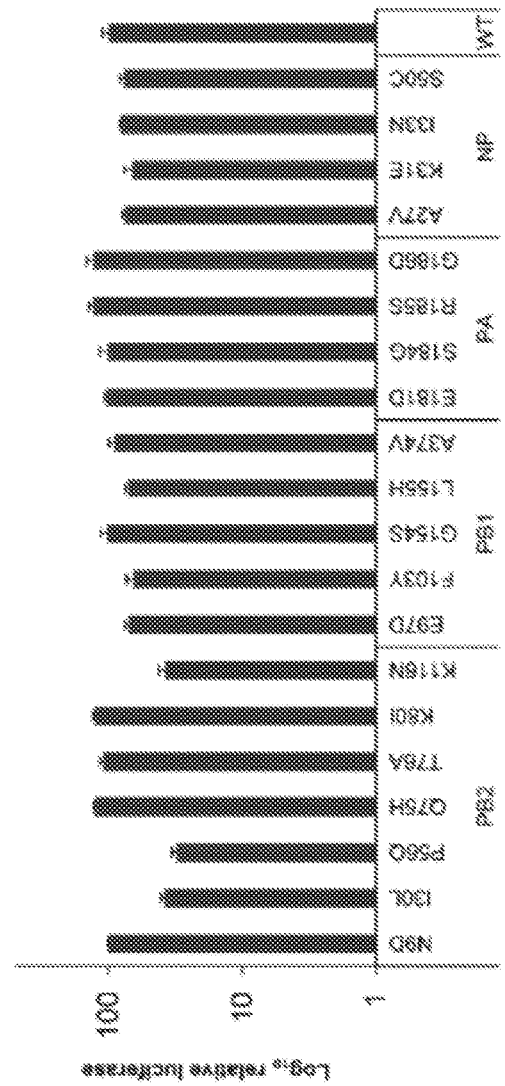
Figure 14A:
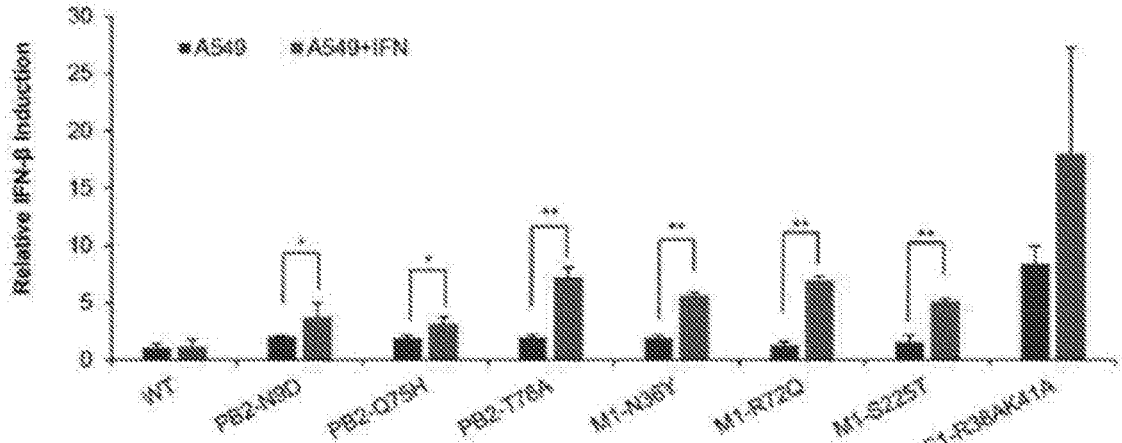
Figure 14B:
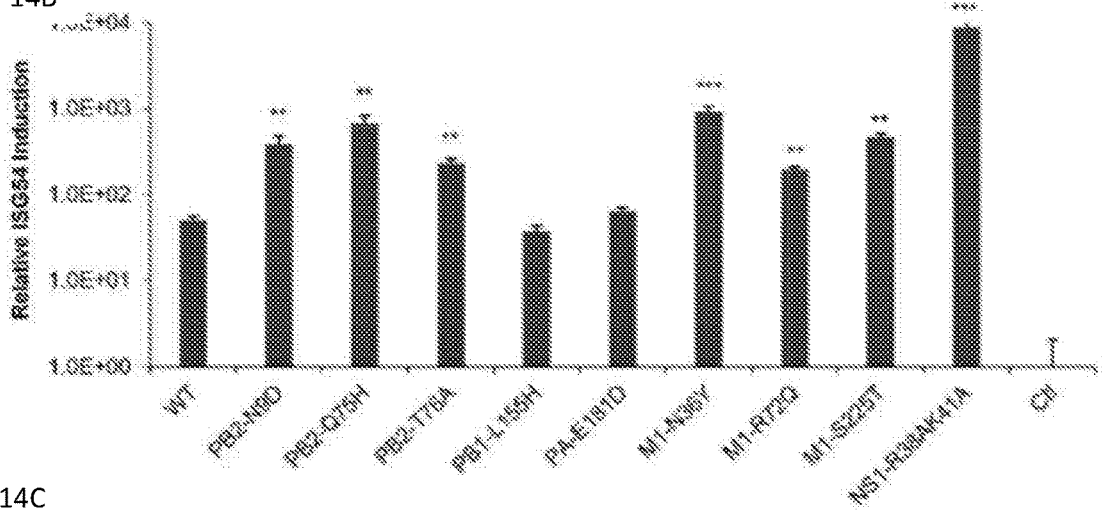
Figure 14C:
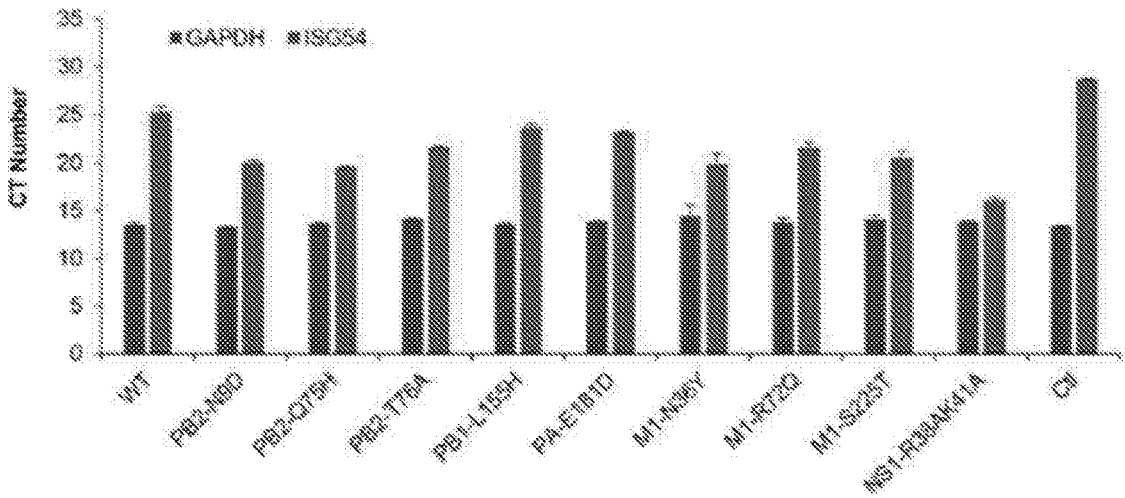
Figure 15:
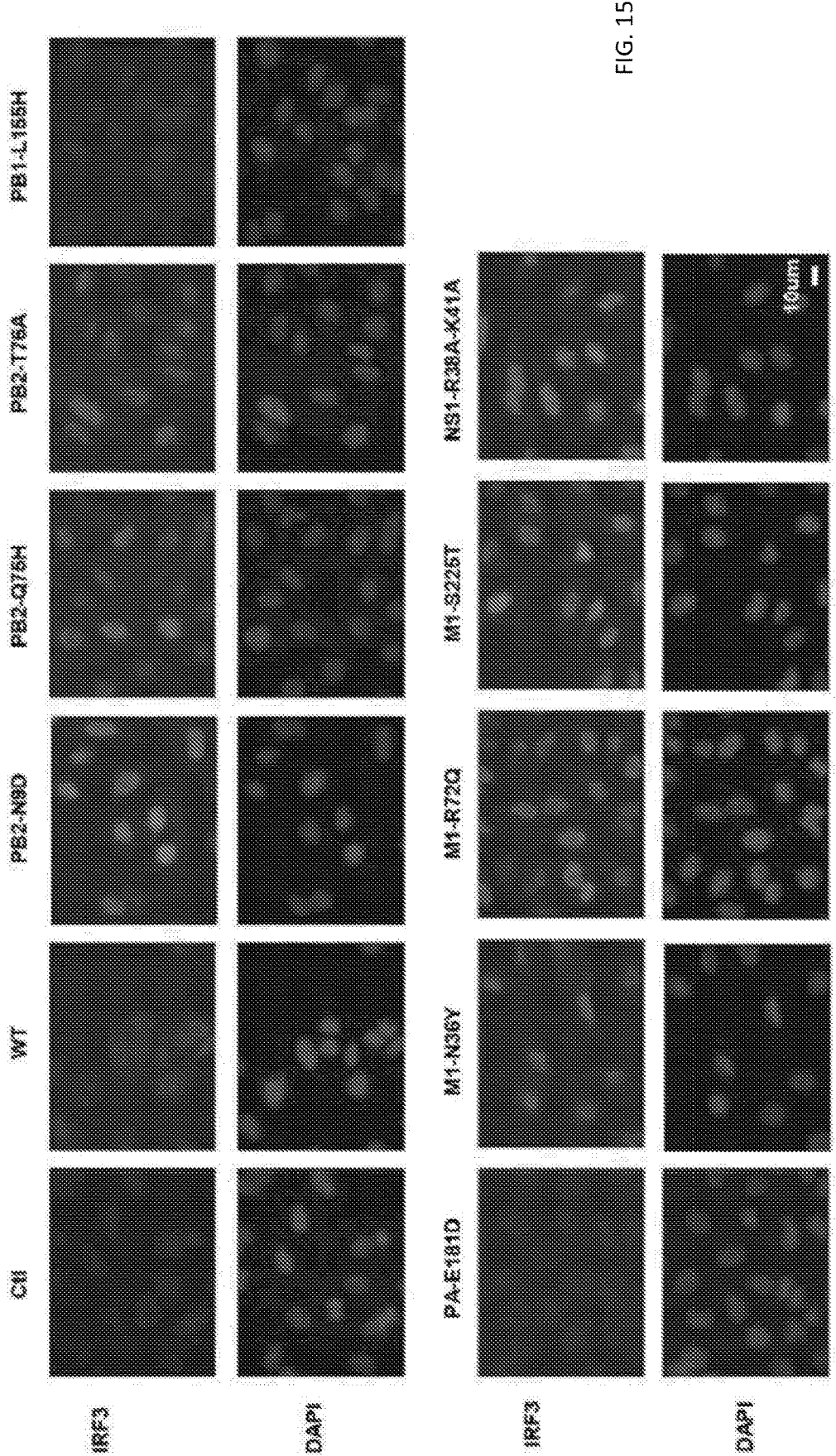
Figure 16:
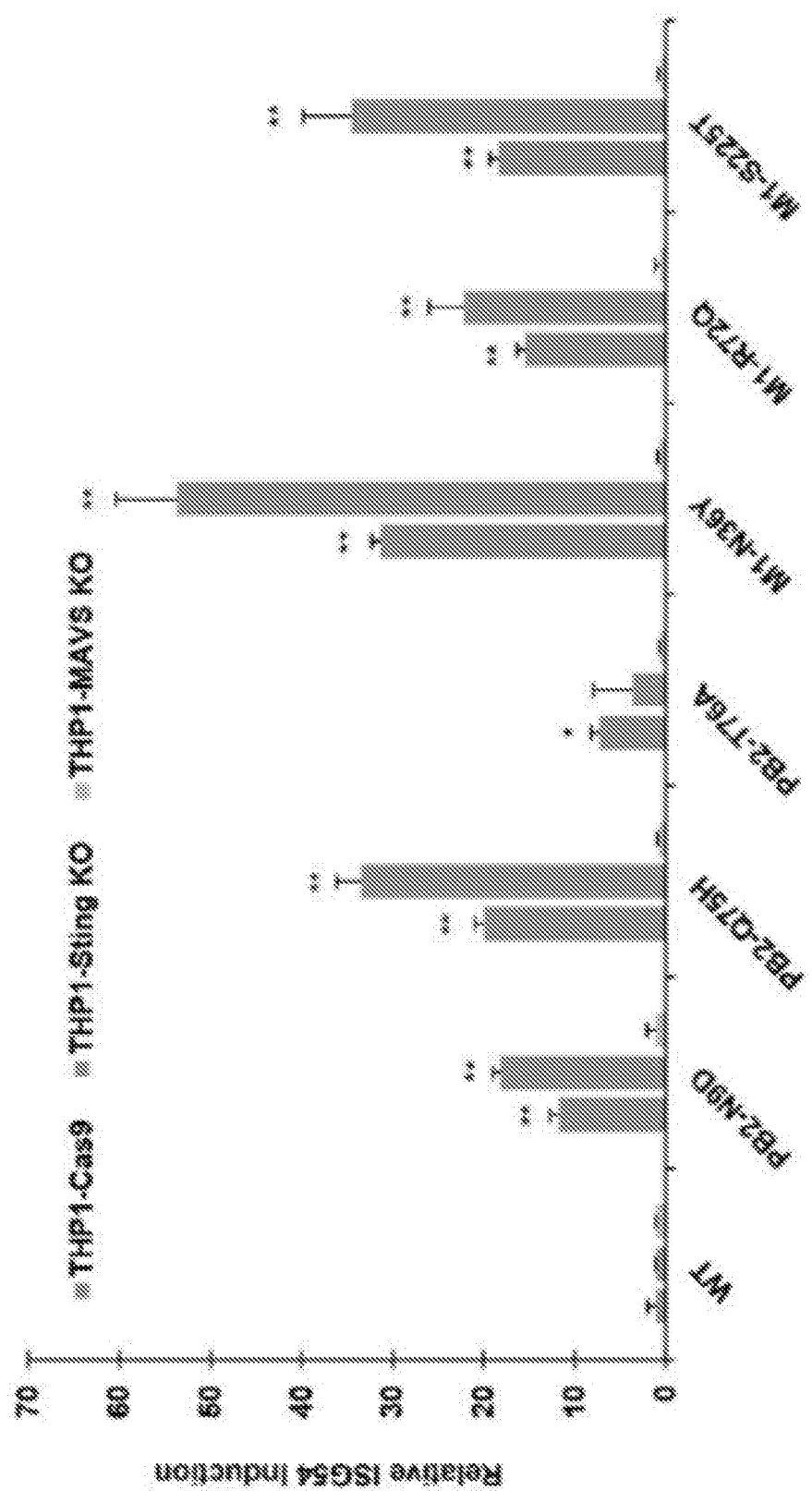

The RF scores of most mutants are correlated in the presence and absence of exogenous IFN treatment; however, we observed a set of mutations that were nearly neutral in the absence of IFN but highly deleterious under IFN selection (FIG. 1B and FIG. 11). These putative IFN-sensitive mutations were widespread on multiple viral segments. Among all influenza A viral proteins, NS1 has been extensively studied for its interaction with the IFN pathway (19, 26, 27), which is validated both in our fitness profiling and individually constructed NS1 mutant viruses (FIG. 12). To further explore IFN-modulating functions across the genome, we focused on IFN-sensitive mutations outside NS1, especially the solvent-exposed and structurally clustered residues in the polymerase complex (PB2, PB1, PA, and NP), as well as the M1 and M2 proteins (FIG. 1C and FIG. 11). Twenty-six mutations were constructed individually, most of which were nearly neutral for viral replication with nearly intact polymerase activity (FIG. 13). These included the previously characterized mutations PB2-N9D, which is known to counteract the inhibition of MAVS (mitochondrial antiviral signaling protein)-induced IFN-β production by PB2 (16), and M1-D30N, which has been shown to induce IFN-β production (17). Several mutations significantly increased IFN sensitivity compared with WT, and the top eight were chosen for further characterization (FIG. 1D). Six of them (PB2-N9D, PB2-Q75H, PB2-T76A, M1-N36Y, M1-R72Q, and M1-S225T) elevated the expression of IFN-β and ISG54 (FIG. 1E and FIG. 14) and stimulated nuclear translocation of IRF3 (FIG. 15). We also observed that the IFN induction was MAVS-dependent and STING (stimulator of interferon genes)-independent (FIG. 16). Moreover, these six mutants were not sensitive to IFN treatment in Vero cells, which are deficient in IFN production. However, the other two mutations (PB1-L155H and PA-E181D) did not induce higher IFN production (FIG. 1E) and were still IFN-sensitive in Vero cells, suggesting that these mutants likely affect processes downstream of IFN production.

c. Combining Mutations Increases IFN Sensitivity and IFN Induction In Vitro

Figure 2A:
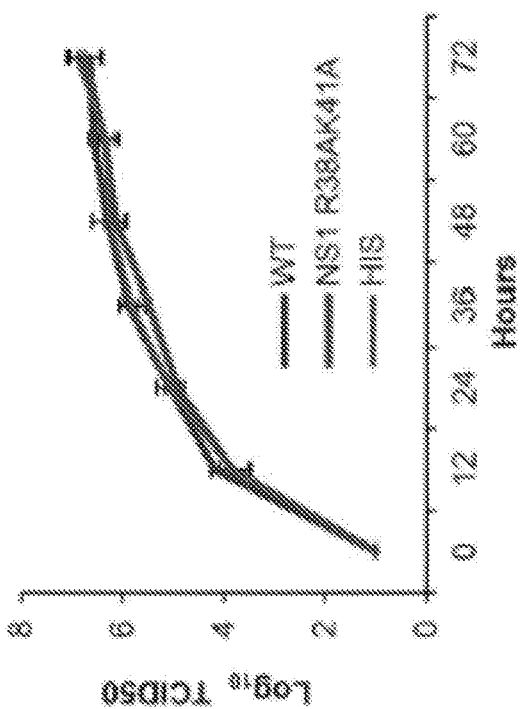
FIG. 2 The combination of mutations in HIS virus increases IFN sensitivity and IFN production. (A and B) Replication kinetics of WT, NS1 mutant, and HIS viruses in A549 (A) and Vero (B) cells. (C) IFN sensitivity of WT, NS1 mutant, and HIS viruses (n=4). (D) Induction of IFN-β expression by indicated virus in A549 cells at 6 hours post-infection, with mock infection as Ctl (n=3). (E) Global gene expression in A549 cells infected with indicated viruses was examined by RNA sequencing (n=2). The heatmap shows the genes that were significantly differentially expressed in HIS-infected cells compared with mock-infected cells. IFN response genes are marked on the left with black bars. (F) GO enrichment analysis of genes up-regulated in HIS-infected cells in comparison with mock- (top) or WT-infected (bottom) cells. (G) Induction of IFN-β expression by indicated viruses in primary human alveolar macrophages (AMs), human alveolar epithelial cells (AECs), human small airway epithelial cells (HSAECs), and human bronchial epithelial cells (HBECs) at 6 hours post-infection, with mock infection as Ctl (n=3). (H) Induction of indicated ISGs and inflammatory cytokines in primary human AMs at 6 hours post-infection (n=3). (I) Induction of indicated ISGs. Error bars, SD. *$P<0.05$, $P<0.01$, *$P<0.001$ [one-way analysis of variance (ANOVA) with Bonferroni multiple comparisons test]; n.s, not significant.
Figure 2B:
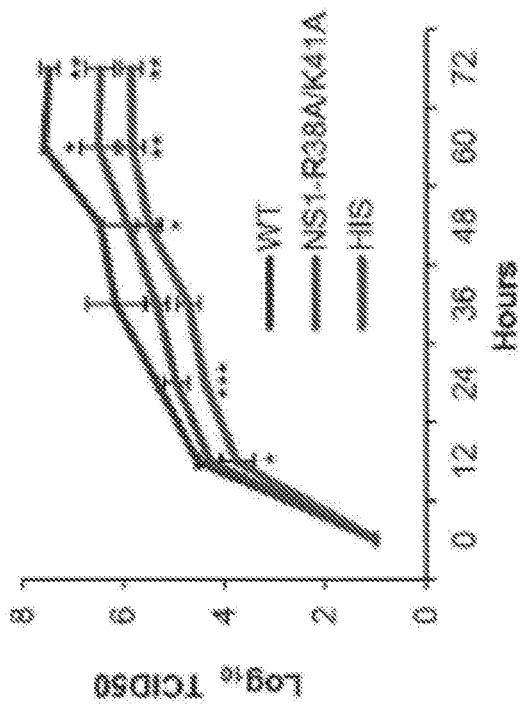
Figure 2C:
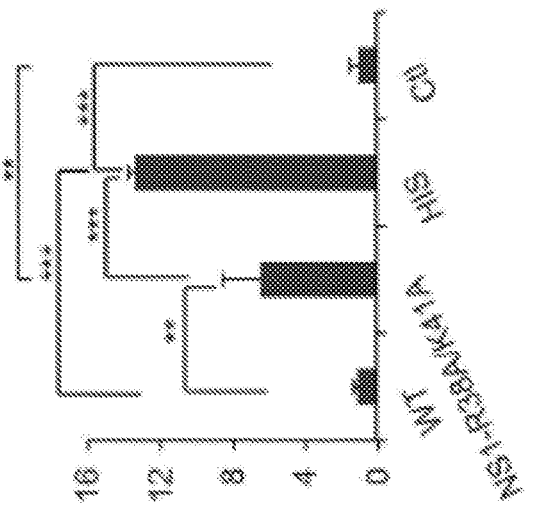
Figure 2D:
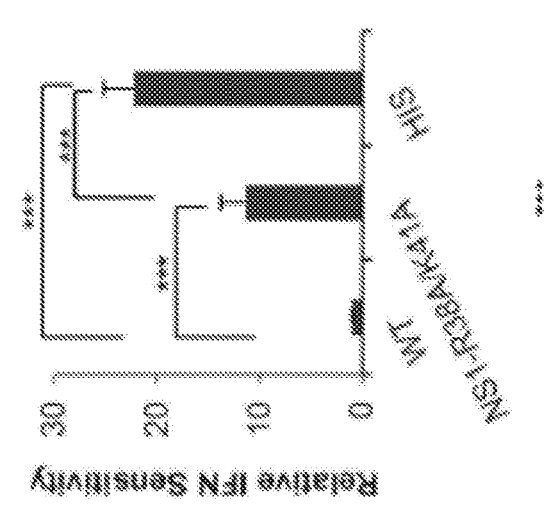
Figure 2E:
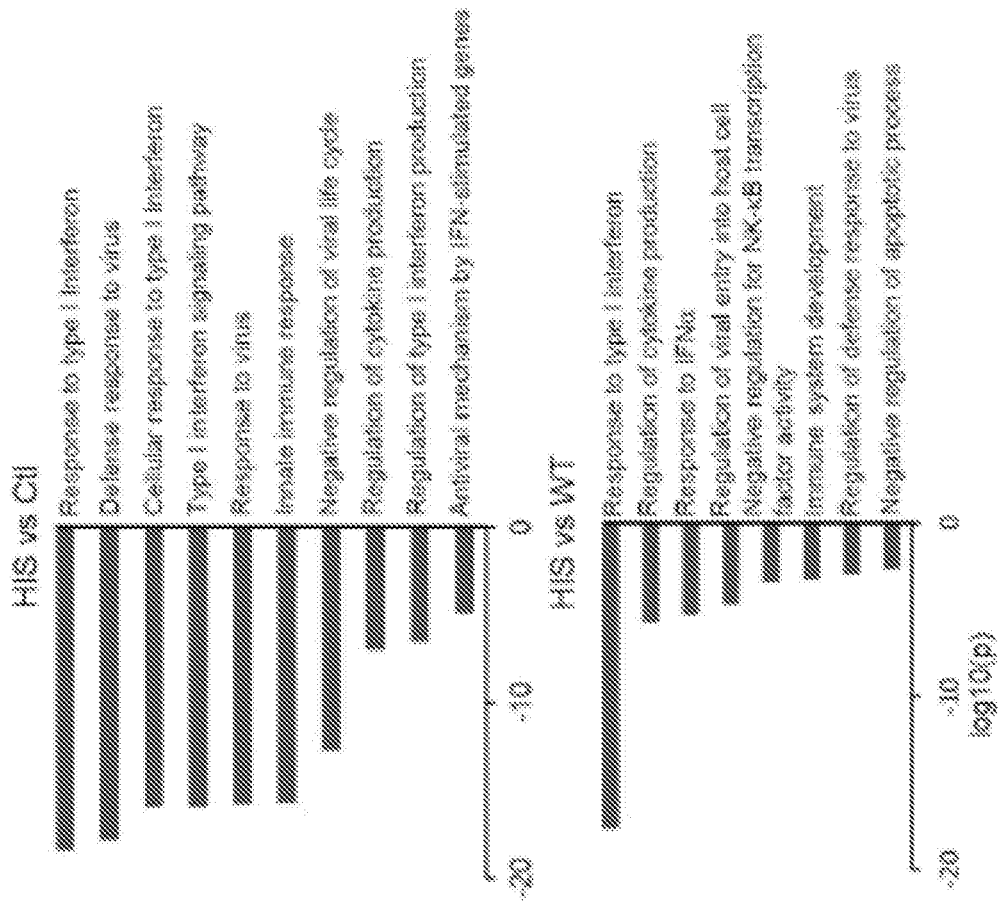
Figure 2F:
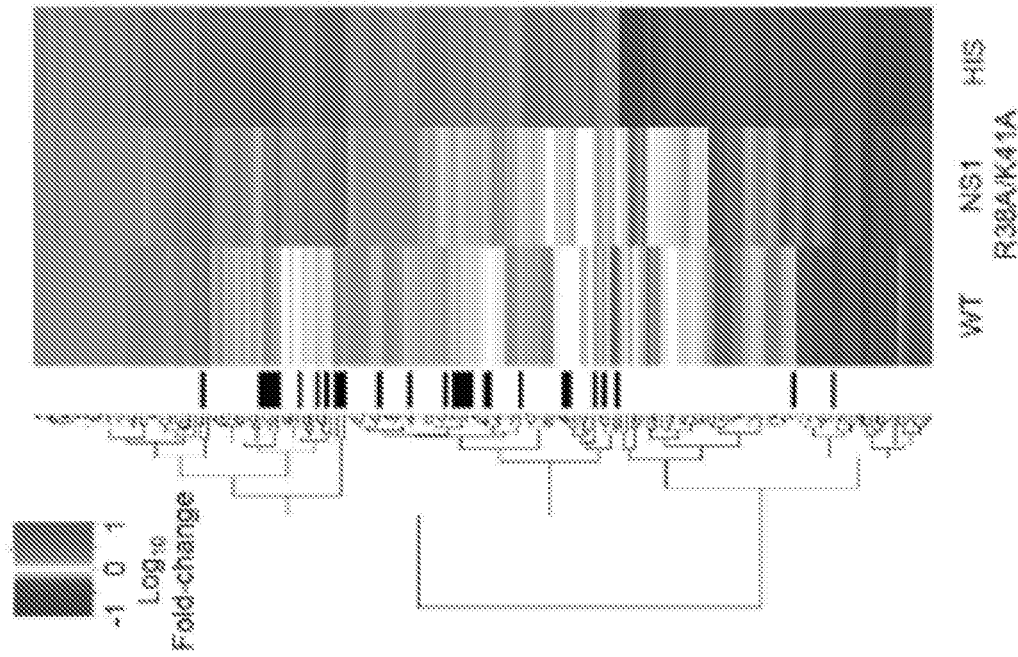

To maximize IFN sensitivity and IFN induction, we combined three IFN-inducing mutations on PB2 (N9D, Q75H, and T76A), three on M1 (N36Y, R72Q, and S225T), and two previously reported ones on NS1 (R38A and K41A) to create the HIS virus. The growth of HIS virus in IFN-competent A549 cells showed significant attenuation compared with that of WT virus (1.4-log decrease at 36 hours and 1.8-log decrease at 60 hours) but was fully restored in IFN-deficient Vero cells (FIGS. 2, A and B). The IFN sensitivity of HIS virus was significantly higher than that of the NS1-R38A/K41A mutant, indicating an independent effect of mutations on PB2 and M1 (FIG. 2C). Gene expression data from lung epithelial and macrophage cell lines (A549 and THP1) showed that HIS virus induced higher IFN production and responses (FIG. 2D and FIG. 17, A to C). Using RNA sequencing, we evaluated the global gene expression changes in A549 cells infected with WT, NS1-R38A/K41A, or HIS virus. At 6 hours post-infection, the expression of 120 genes was significantly up-regulated (fold change >2 and P<0.001) in HIS-infected cells, of which 24% were IFN response genes (FIG. 2E, FIG. 17D). Gene Ontology (GO) enrichment analysis revealed that the pathways related to IFN production and response were the dominant ones activated by HIS virus, to a greater extent than by WT or mock infection (FIG. 2F). Furthermore, HIS virus induced negative regulators of apoptosis process, such as TNFAIP3, an important inhibitor of TNF-mediated apoptosis. Slower cell death was observed with HIS infection than with WT infection (FIG. 17E).

Figure 2G:
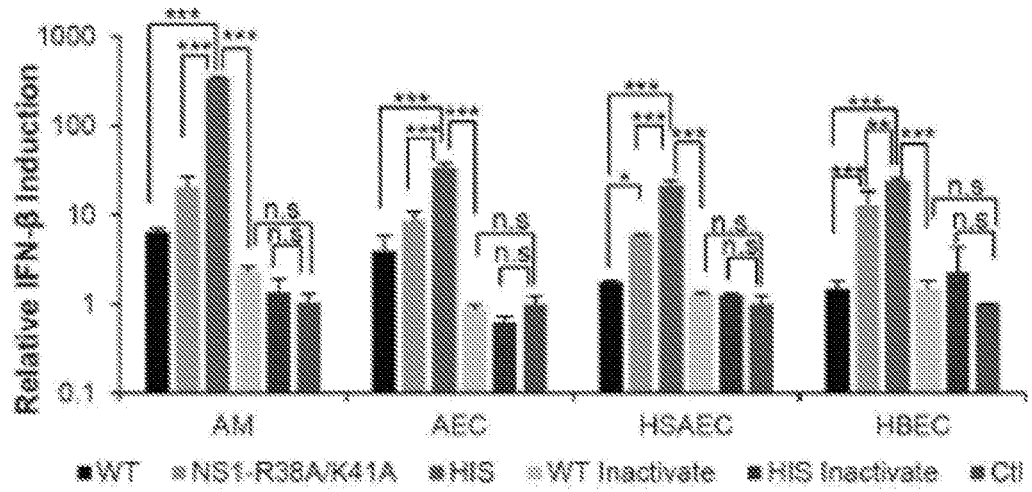
Figure 2H:
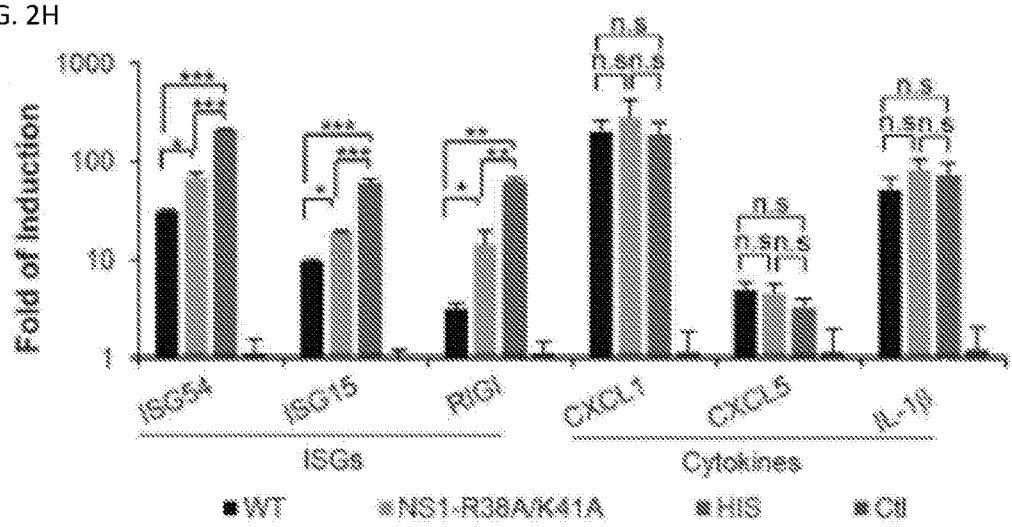
Figure 2I:
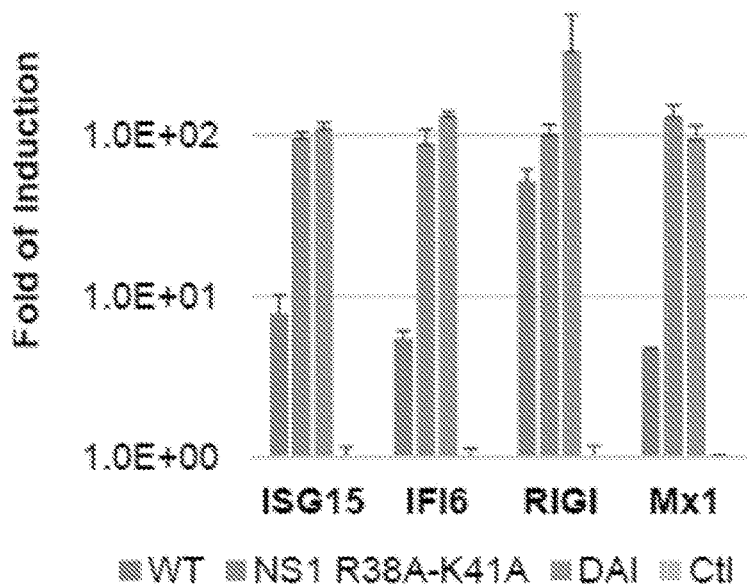

We further defined the phenotypes of HIS virus with a panel of human lung cells, including immortalized small airway epithelial cells, bronchial epithelial cells, primary alveolar epithelial cells, and primary alveolar macrophages (FIG. 2G). HIS virus induced the strongest up-regulation of IFN-β expression (~50-fold relative to WT) in the primary alveolar macrophages, an important target for influenza infection (FIG. 2G), and greater up-regulation of ISGs than WT virus (FIG. 2F). HIS virus did not enhance the expression of other inflammatory cytokines [CXCL1, CXCL5, or interleukin-1β (IL-1β)] in the infected macrophages, highlighting its specific effects on the IFN pathway (FIG. 2H). The phenotype of HIS virus is not limited to the WSN background: Introducing these eight mutations into another H1N1 strain of influenza, A/PR8/34 (PR8-HIS), led to a similar phenotype (FIGS. 17, F and G). The up-regulation of the IFN pathway requires active viral infection, given that formalin-inactivated HIS virus lost the ability to induce higher IFN-β expression (FIG. 2G).

d. HIS Virus is Highly Attenuated in IFN-Competent Mice and Ferrets

Figure 3L:
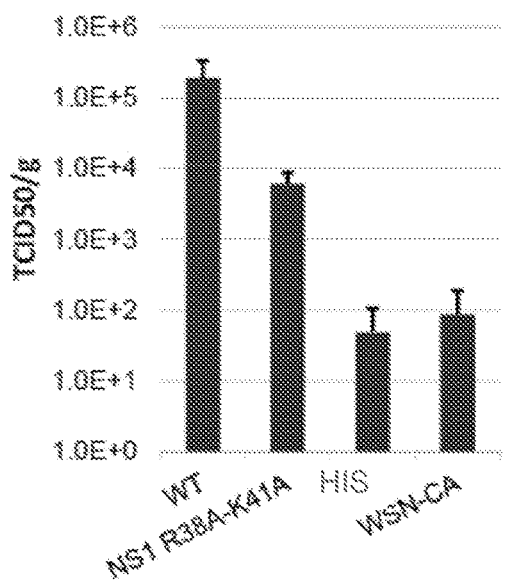
FIG. 3 HIS virus is replication-deficient in vivo and induces a transient IFN response. (A and B) Survival rate and percentage of body weight loss after intranasal infection (n=5). (C and D) Viral titers at day 2 post-infection (n=4) (C) and replication kinetics (n=3) (D) of WT and HIS viruses in mouse lung tissues. (E) Induction of indicated ISGs in mouse lung tissues at 6, 24, 48, and 120 hours (h) post-infection (n=3), shown as fold of induction over mock infection. RNase H, ribonuclease H. (F) Gene expression of indicated inflammatory cytokines in mouse lung tissues was examined by RNA sequencing (n=2). (G) HE (hematoxylin and eosin) staining of lung tissues at day 9 post-infection. Thick arrows, bronchioles; thin arrows, vessels; red triangles, inflammatory cell infiltration. (H) Percentage of neutrophils, monocytes, and lymphocytes in BAL cytospins at day 9 post-infection (n=3). (I) Cytokines in BAL samples measured by Luminex multiplex assay (n=4). (J) Replication of indicated viruses in lung tissues of IFNAR$^{-/-}$ mice (n=4). (K) Viral titer of WT and HIS viruses in ferret nasal wash, trachea, and lung tissues (n=3). Dashed lines represent detection limits. (L) Viral titer in lung tissue are shown for indicated virus. Female Balb/c mice age 6-8 weeks were intranasally infected with $10^5$ TCID 50 of indicated virus, mice lung tissue were extracted at 2 days post infection (N=3). (M) Replication of indicated virus in IFNAR−/− mice. IFNAR−/− mice were infected intranasally with $10^5$ TCID 50 of indicated virus, mice lung tissue were extracted at 2 days post infection (N=3=number of mice per group). (G) Induction of indicated ISGs were examined for mice lung samples infected with WT or HIS virus at 6 h or 24 h. (N) Induction of indicated cytokines were examined with luminex multiplex assay with BAL samples collected at day 2 post infection (N=3). Error bars, SD. *$P<0.05$, $P<0.01$, *$P<0.001$ [log-rank test for (A); ANOVA with Bonferroni multiple comparisons test for (C), (H), and (J); and two-tailed t test for (D), (E), (I), and (K)].
Figure 3M:
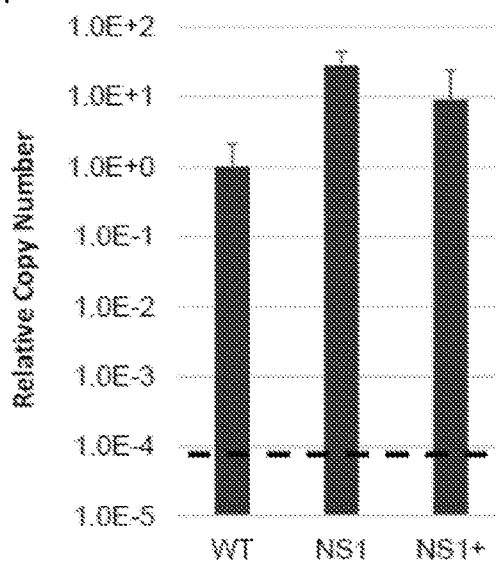
Figure 3N:
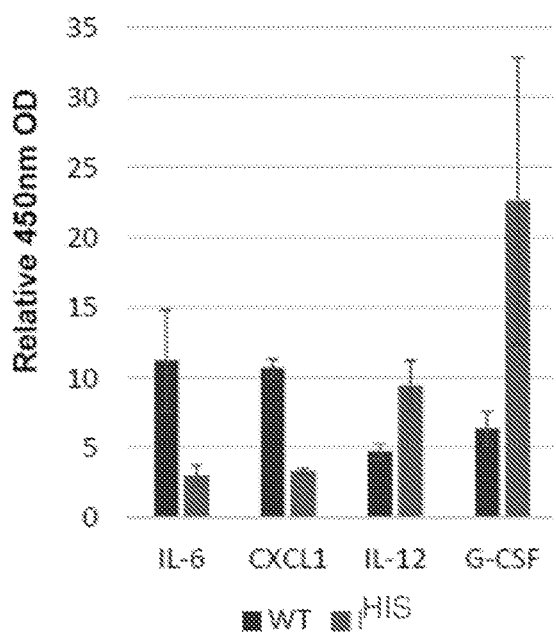
Figure 18B:
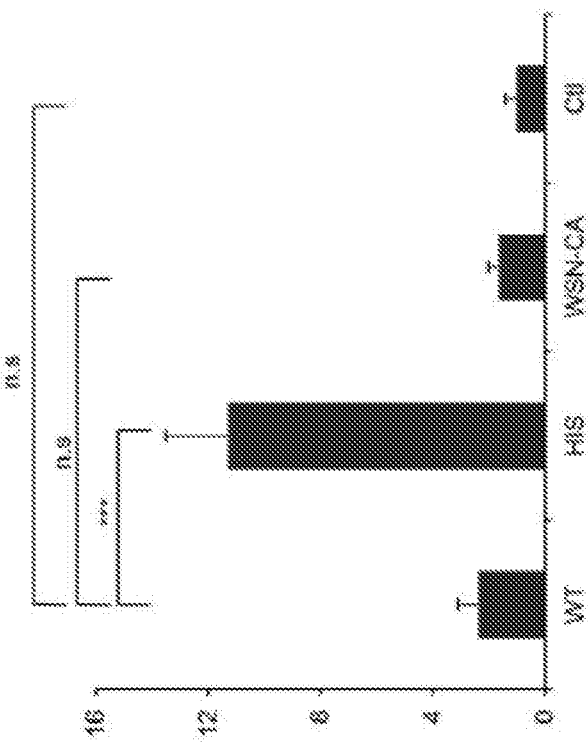
Figure 18A:
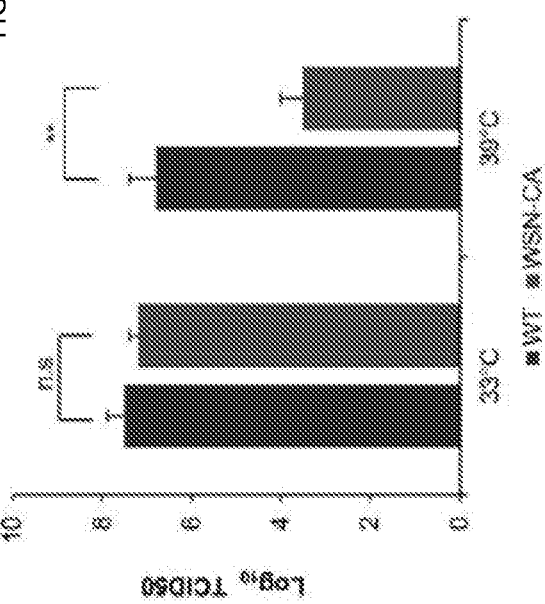

We next measured the replication and pathogenesis of HIS virus in mice and ferrets, the most commonly used animal models for influenza virus. BALB/c mice were intranasally inoculated with WT or HIS virus at different doses. Whereas the median lethal dose of WT virus was $5\times10^5$ TCID50 (50% tissue culture infective dose), and $1\times10^3$ TCID50 caused obvious body weight loss in all animals, neither weight loss nor indicative clinical symptoms were observed in HIS-infected mice given $1\times10^7$ TCID50, the highest dose that we have tested (FIGS. 3, A and B). To compare the HIS virus approach with the live attenuated vaccine strategy used in FluMist, we incorporated the five cold-adapted (CA) mutations from FluMist into the WSN background and generated a WSN-CA virus (28, 29). WSN-CA virus replicated well at 33° C. but was highly attenuated at 39° C. and induced IFN-β expression to a similar level as WT virus, which was significantly lower than that induced by HIS virus (FIG. 18). By day 2 post-inoculation, replication of HIS virus in mouse lung tissues was significantly lower than that of WT virus (~3.6-log decrease) or the NS1-R38A/K41A mutant (~2-log decrease) and comparable to that of WSN-CA virus (FIG. 3C and FIG. 19A). In contrast with the robust viral replication observed for WT infection, which peaked at 48 hours, no increase in viral copy number was detected in HIS-infected mice at any tested time point (FIG. 3D). PR8-HIS virus was also significantly attenuated compared with WT PR8 virus in mouse lung tissues (FIG. 19B). Although highly attenuated in replication, HIS virus showed transient yet significant up-regulation of IFN and ISGs at 6 and 24 hours post-infection, after which the response was diminished (FIG. 3E). In contrast, WT virus induced a robust pro-inflammatory response throughout the course of infection, exemplified by the high induction of CXCL10 at 48 and 120 hours post-infection (FIG. 3F). These results correlate well with histological analysis of infected lungs and cytospins of bronchoalveolar lavage (BAL) fluid (FIGS. 3, G and H, and FIG. 19, C to G). HIS-infected lungs showed infiltration of neutrophils and lymphocytes at day 2 post-infection; however, the infiltration was transient and cleared by day 9. Sustained inflammation and tissue damage was observed for WT-infected lungs, which became more severe by day 9 post-infection (FIG. 3H and FIGS. 19, H and I). We also examined the cytokine response in the BAL samples at 48 hours post-infection by means of Luminex multiplex assay (FIG. 3I and FIGS. 19, J and K). WT infection showed significantly higher levels of IL-6 and CXCL1, consistent with the observed severe inflammation. In contrast, HIS virus induced higher amounts of IL-12 and G-CSF, which is important for granulocyte stimulation and T cell development. Furthermore, replication of HIS virus was fully restored to WT levels in IFNAR$^{-/-}$ mice, indicating that the inability to counteract IFN response was the underlying mechanism for the highly attenuated replication of HIS virus in wild-type mice (FIG. 3J). In the ferret model, we also observed significant attenuation of HIS virus (FIG. 3K). By day 3 post-infection, HIS virus showed a ~2-log decrease in trachea and a ~1.5-log decrease in lung tissues compared with WT virus. Moreover, no infectious viral particles were detected in nasal washes of HIS-infected ferrets, in contrast to the robust viral shedding observed during WT infection.

e. HIS Virus Induces Strong and Broad Adaptive Immune Responses

Figure 4O:
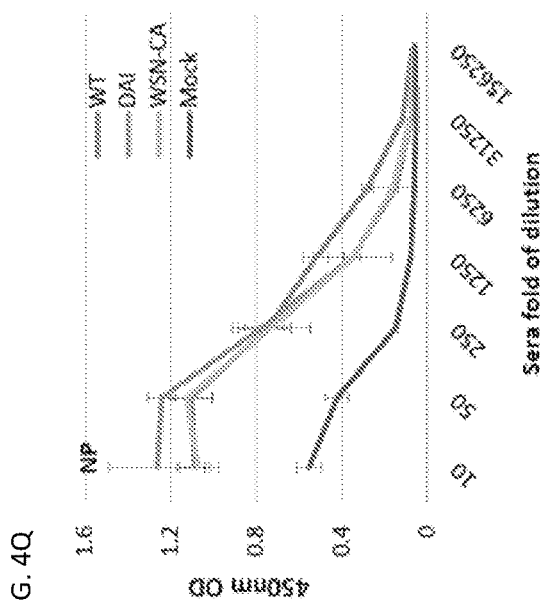
FIG. 4 HIS virus induces strong adaptive immune responses in mice and ferrets. (A to D) HA-binding IgG (n=7), HA neutralizing antibody (n=7), and NP- and NA-binding IgG (n=4) in mouse sera at day 28 post-vaccination. HAI, hemagglutinin inhibition. (E) HA-binding IgA in BAL samples at day 28 post-vaccination (n=4). The optical density (OD) in ELISA was 450 nm. (F) HA neutralizing antibody levels in ferret sera at day 22 post-vaccination (n=3). The dashed line represents the detection limit. (G) Mutations not neutralized by mouse sera (red) were mapped onto the HA structure (PDB ID, 1RUZ; n=5) (40). The other five colors represent five well-characterized neutralization epitopes. (H) Tetramer staining of antigen-specific CD8 T cells in mouse lung (left) and spleen (right) at day 10 post-vaccination (n=10). (I) Percentage of antigen-specific memory precursor effector cells in mouse lung and spleen (n=3). (J) NP antigen-specific CD8 T cells during the secondary responses in lung tissues from mice vaccinated with indicated viruses (n=4). (K) Intracellular IFN-γ staining of CD4 T cells induced by the indicated viruses (n=3). (L and M) Clonality of TCRβ sequences of NP antigen-specific CD8 T cells during the primary (n=5) (L) or secondary (n=4) (M) responses. (N) Box plots show the fitness distribution of mutations on T cell epitopes or antibody epitopes. (O&P) Specific HA binding IgG (O) and neutralizing antibody (B) from infected mice sera were examined by ELISA and hemagglutinin inhibition (HAI) assay. Female Balb/c mice age 6-8 weeks were intranasally infected with $10^5$ TCID 50 of indicated virus (N=7), serum were obtained at day 28 post infection. Sera were heat inactivated for HAI assay. (Q) Specific NP binding IgG from infected mice sera were examined by ELISA (N=4). (R) Primary T cell response was examined by flow cytometry with tetramer staining. Female C57/B6 mice were intranasally infected with $10^5$ TCID 50 of indicated virus (N=5). Single cell suspension was made from lung and spleen tissues extracted 8 days post infection. Red blood cells were lysed with ACK lysis buffer. 1 million cells were subjected to flow cytometry analysis with CD3, CD8 and tetramer complexes with H-2D$^b$+influenza A virus NP$_{366-374}$ (NPP, ASNENME™) and H-2K$^b$ influenza A virus PBI$_{703-711}$ (SSYRRPVGI). (S) TCID50 are shown for challenge infection post vaccination. Female Balb/c mice age 6-8 weeks were intranasally vaccinated with $10^5$ TCID 50 of indicated virus (N=4). Mice were challenged with $10^5$ TCID 50 of WT virus at 28 days post vaccination. Lung tissues were extracted at 2 days post challenge. Viral titers were measured by TCID50 assay using A549 cells. Dashed line represents the detection limit of TCID50 assay. Error bars, SD. *P<0.05, P<0.01, *P<0.001 [ANOVA with Bonferroni multiple comparisons test for (A) to (D), (F), (H), (J), and (K); two-tailed t test for (I), (L), and (M); and Wilcoxon rank sum test for (N)].
Figure 4P:
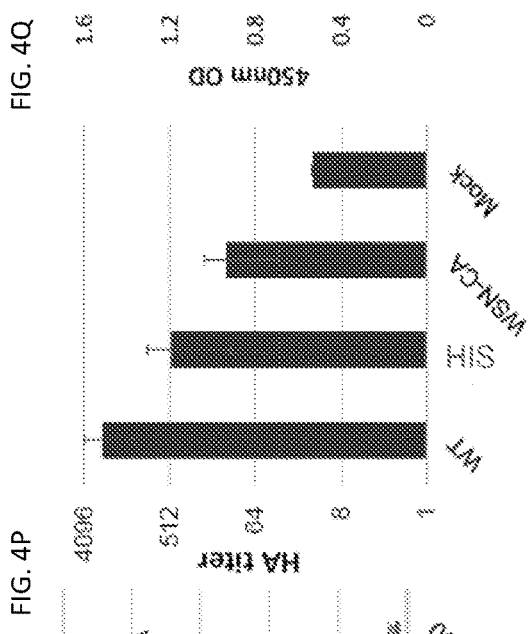

We then examined the ability of the HIS virus to induce humoral and cellular responses. Mouse sera and BAL samples were collected at day 28 after single-dose ($1\times10^4$ TCID50) vaccination with WT, HIS, or WSN-CA virus. HIS virus induced robust antibody responses, as measured by ELISA (enzyme-linked immunosorbent assay) and hemagglutinin (HA) inhibition and neutralization antibody assays (FIG. 4, A to E, and FIG. 20). The level of HA antibody responses elicited by HIS virus was lower than for WT virus, yet significantly higher than for the WSN-CA, inactivated WT, and inactivated HIS viruses (FIGS. 4, A and B, and FIGS. 20, C and D). Immunoglobulin G (IgG) antibodies against NP, NA, and M1 proteins, which have been shown to play an important role in limiting viral replication (30, 31), were also detected in the sera of HIS-vaccinated mice at a level comparable to that in WT-infected mice (FIGS. 4, C and D, and FIG. 20E). Furthermore, mucosal immune responses, indicated by secretory IgA antibodies against HA and NP proteins, were elicited by HIS vaccination (FIG. 4E and FIG. 20F). Robust HA antibody responses were also observed in ferrets vaccinated with HIS virus (FIG. 4F and FIG. 20G), which were sustained for at least 50 days post-vaccination. To examine the epitope coverage of the neutralizing antibodies generated by HIS virus, we profiled the HA mutants in the presence or absence of mouse serum antibodies by using the high-throughput genomic approach (32). Mutations not neutralized by sera were observed in both head (Ca2 and Sa sites) and stem regions, with no significant difference in the number or the distribution of mutations between the WT and HIS viruses (FIG. 4G, FIG. 21). This suggests that the breadth and diversity of neutralizing antibodies induced by the HIS virus are comparable to those induced by the WT virus.

In addition to humoral responses, HIS virus elicited NP and PB1 antigen-specific CD8 T cell responses, similarly to WT virus and much more strongly than the WSN-CA, inactivated WT, and inactivated HIS viruses (FIG. 4H and FIG. 22, A to D). The CD8 T cells induced by the WT and HIS viruses had a similar capacity for IFN-γ production upon stimulation by viral epitope peptides (FIG. 22E). We further examined the phenotypes of virus-specific T cells by quantifying the expression of KLRG1, CD127, CD44, CD62L, and CCR7. By day 21 post-infection, the NP and PB1 antigen-specific CD8 T cells induced by the WT and HIS viruses displayed similar levels of memory precursor effector cells with a CD127$^{high}$KLRG1$^{low}$ phenotype and short-lived effector cells with a CD127$^{low}$KLRG1$^{high}$ phenotype (FIG. 4I and FIG. 22F). These virus-specific CD8 T cells also displayed a similar effector/memory phenotype, as measured by CD62L, CD44, and CCR7 expression (FIGS. 22, G and H). Consistently, after challenge infection at 1 month post-vaccination, HIS virus induced the secondary CD8 T cell responses similarly to WT but more strongly than WSN-CA virus (FIG. 4J and FIG. 22I). Moreover, similar frequencies of influenza-specific CD4 T cells were elicited by the WT and HIS viruses (FIG. 4K). To examine the diversity of the primary and secondary T cell responses, we analyzed the T cell receptor repertoire by sequencing the β T cell receptor (TCRβ) loci of NP-specific CD8 T cells in mice vaccinated with WT or HIS virus. The Vβ usage and clonality for both primary and secondary T cell responses were comparable between the WT and HIS viruses, documenting the diversity of T cell lineages induced by HIS vaccination (FIGS. 4, L and M, and FIG. 23).

We analyzed the potential impact of immune responses on the viral genome at the population level. Our whole-genome fitness profiling provides a data set for examining the genetic flexibility of viral sequences. We calculated the fitness cost of mutations in the previously identified B and T cell epitopes. Mutations on several T cell epitopes, but not on antibody epitopes, were generally correlated with lower fitness scores (FIG. 4N). Our results suggest that an escape from T cell selection will impose a higher fitness cost for the virus, and thus T cell responses will be effective against vaccine escape.

f. HIS Virus Protects Against Homologous and Heterologous Viral Challenge

We examined whether HIS vaccination could offer protection against homologous and heterologous viral challenges. Immunized mice were challenged 28 days post-vaccination with $1\times10^4$ TCID50 of WT virus. Vaccination by HIS virus reduced viral replication by ~3 log, with no sign of weight loss (FIG. 5 and FIG. 24). Complete protection without detectable viral titers in the lung was achieved with one vaccination at a high dose ($1\times10^6$ TCID50) or two vaccinations at a low dose ($1\times10^4$ TCID50) (FIG. 5B and FIG. 24B). Similar protective effects were observed in ferrets, which were challenged with $1\times10^7$ TCID50 of WT virus at day 35 post-vaccination. Nasal washes were collected at days 1, 3, 4, 7, and 9 post-challenge, and no infectious viral particles were detected in nasal washes from HIS-vaccinated ferrets throughout this time period (FIG. 5C).

To test whether HIS vaccination provides protection against heterologous strains, we first challenged immunized mice with PR8 virus and examined viral titer at day 2 post-challenge. HIS vaccination reduced viral titer by ~3 log compared with mock vaccination and significantly more than WSN-CA vaccination (FIG. 24C). We further challenged vaccinated mice with a lethal dose of three different influenza strains: H1N1 subtypes A/PR8/34 and A/Cal/04/09 and H3N2 subtype A/X-31. Protection by HIS vaccination was observed in all measures, including survival rate, percentage of body weight loss, and clinical scores (FIGS. 5, D and E, and FIG. 24D). Strong secondary antigen-specific T cell responses were observed in the challenged mice for all strains (FIG. 25). HIS vaccination also protected ferrets from heterologous A/Cal/07/09 challenge, as shown by viral titer in nasal washes and percentage of body weight loss (FIG. 5F and FIG. 24E).

g. Discussion of Results for the Example

Although NS1 is the best studied IFN antagonist in influenza genome, the anti-IFN function has been recently appreciated in other proteins. It is reported that PB2 and PB1F2 could bind to MAVS and inhibit interferon production; ESIE motif in PB1 and PA can mediate type I interferon response, and NP of newly emerged H7N9 can counteract anti-viral ISG: MxA. Here, using a high-throughput genetic approach, we have identified multiple IFN sensitive mutations in the PB2, PA, PB1 and M1 proteins, suggesting the anti-IFN functions of corresponding WT proteins. As anti-IFN functions are essential for efficient viral replication in vivo, it is reasonable that the functions are distributed in different segments. Identified IFN sensitive mutations also work on different parts of IFN system. Mutations on PB2 and M1 can induce higher IFN production, indicating that they work at the upstream of IFN system. On the other hand, mutation on PB1 and PA cannot induce higher IFN production and response, and the sensitivity still remains in IFN deficient Vero cells, suggesting that they might be interacting with JAK/STAT pathway or a specific anti-viral ISG. Identification of these mutations open the path to dissect the underlying mechanisms.

Conventional approaches to develop vaccines render the virus avirulent but also reduce immunogenicity. We developed a quantitative high-throughput genomics approach to systematically identify and eliminate immune-modulating functions in the virus genome while maintaining replication fitness in vitro. This is a systems-based strategy to enhance viral immunogenicity while attenuating replication and pathogenesis. In this proof-of-principle study, we generated a HIS virus with a combination of eight IFN-sensitive mutations. These mutations also induced higher IFN production and response. We demonstrated that HIS virus is highly attenuated in vivo but is able to induce transient IFN responses, elicit robust and diverse humoral and cellular immunity, and provide protection against homologous and heterologous viral challenges in mice and ferrets.

Recent studies have suggested several strategies to design live attenuated vaccines (14, 15, 33-37). Our method is distinctive in the following aspects: (i) We systematically investigated the whole viral genome, and we eliminated immune-evasion functions at multiple loci to obtain a safe strain that has no detectable replication in vivo; (ii) we selected mutants that induce a higher IFN response, because a transient IFN response has been shown to be essential for adaptive immunity, including the strong and diverse T cell responses; (iii) HIS virus selectively induced a transient IFN response but no other tested inflammatory responses, which reduced potential pathogenesis or side effects for future clinical usage. We have also applied this approach to a DNA virus and generated an effective vaccine candidate.

In general, this unbiased and quantitative high-throughput genomics system can be widely applied to other pathogens to define the impact of genome-wide mutations under certain selection conditions. Similar profiling of a viral genome can be performed with other immune components, such as cytokines, natural killer cells, or T cells, in vitro and in vivo. Inactivating additional immune evasion functions in the virus will further increase the safety and immunogenicity of its derivatives for prevention or therapy.

II. Materials and Methods Used for the Examples in Section I (Influenza A Virus).

a. Viruses, Cells, Mice, and Ferrets

Influenza A/WSN/33 virus (WSN) and Influenza A/PR8/34 virus (PR8) were used to generate WT and mutant viruses. An eight-plasmid reverse genetics system was utilized to reconstitute WT virus (20,41). A live attenuated cold adapted WSN strain (WSN-CA) was generated by introducing 5 mutations in 3 polymerase genes: PB1 (391E, 581G, and 661T), PB2 (265S), and NP (34G). These 5 mutations were derived from A/Ann Arbor/6/60, which was identified in the backbone for vaccine FluMist (28, 42, 43). Influenza A/X-31 (H3N2) and A/Cal/04/09 (H1N1), A/Cal/07/09 (H1N1), in addition to WSN and PR8, were used for the challenge experiments in mice and ferrets.

293T cells were cultured in DMEM (Corning) with 10% FBS (Corning). Madin-Darby Canine Kidney (MDCK) cells were cultured in DMEM with 10% FBS, but changed to OPTI-MEM (Thermo Fisher) with 0.8 mg/ml TPCK trypsin for viral infection with PR8 backgrounds. A549 cells and THP1 cells were cultured in RPMI1640 (Corning) with 10% FBS. THP1 cells with knockout were generated by CRISPR-Cas9 using a lentivirus expressing a gRNA (targets STING or MAVS) and Cas9-T2A cassette (44). THP1 cells were transduced with the lentivirus and selected with 5 μg/ml puromycin (Life Technologies). Human small airway epithelial cells (HSAEC) were cultured in small airway epithelial cell basal media (SABM) with growth supplements (Lonza). Human bronchial epithelial cells (HBEC) were cultured in keratinocyte serum free media include bovine pituitary extract (BPE, 30 Pg/ml) and hrEGF supplements (0.2 ng/ml) (Invitrogen). Human alveolar macrophages were isolated from lungs of de-identified donors and cultured as previously described (45). For culture of human alveolar epithelial cells, the isolated ATII cells were plated in Dulbecco modified Eagle medium (DMEM) with 10% fetal bovine serum (FBS) on rat tail collagen-coated tissue culture plate and after 2 days of adherence, media were switched to DMEM with 5% FBS. AECs were cultured for another 4 days before influenza virus infection. The Committee for Oversight of Research and Clinical Training Involving Decedents and the University of Pittsburgh Institutional Review Board approved the usage of these human tissues.

Female BALB/c mice (Jackson Laboratory) at the age of 6-8 weeks were used to determine safety, pathology, humoral immune responses and protection. Female C57BL/6J mice (Jackson Laboratory) of the same age were used for T cell studies. IFNAR−/− mice in C57BL/6J background were used for viral replication studies (46). Four-six month old female ferrets (body weight around 1 kg) were purchased from Wuxi Cay Ferret Farm (Jiangsu, China) to determine the safety and efficacy of vaccines.

b. Construction of Influenza Mutant Plasmid Library

Interferon sensitivity is defined using a high-throughput genetic system. FIG. 7A illustrates an exemplary single-nucleotide resolution high-throughput genetics approach used to systematically map the interferon sensitive mutations. Thus, we present a novel approach for vaccine development: systematically reprogramming the biological functions after genome-wide functional characterization of the virus.

Libraries of influenza A/WSN/33 mutant viruses were generated using the eight-plasmid transfection system as previously described (18, 21-23, 47). The WSN strain was used to generate the mutant library as it provides flexibility for passaging large complex mutant libraries in a variety of cell lines. In brief, the whole length influenza genome was separated into 52 small fragments of 240 bp each. Random mutagenesis was performed with error-prone polymerase Mutazyme II (Stratagene) for each fragment separately. We have carefully controlled the mutation rate to maximize the proportion of point mutations. 0-3 mutations were expected to be generated for every template. For each small library, the mutated fragment was amplified and gel purified, BsaI or BsmbI (NEB) digested, ligated to the vector and transformed into MegaX DH10B T1R cells (Life Technologies). As each small library was expected to have 1,000 single mutations, 50,000 bacterial colonies were collected to cover the complexity at ~50×. Plasmids from collected bacteria were midi-prepped as the input plasmid library. In each small library, single nucleotide mutation account for 30% of the entire population. Mutant libraries for PB1, PA and M segments were previously constructed (21, 22).

c. Reconstitution, Selection and Tittering of Virus Libraries

To reconstitute the mutant virus library, ~30 million 293T cells were transfected with each plasmid library (one out of 52 small libraries) together with the other 7 plasmids encoding WT viral proteins (32 Pg of DNA in total) using Lipofectamine 2000 (Life Technologies). Media was changed at 24 h post transfection. Viruses were collected at 72 h post transfection. Viral titer (TCID50) was measured using limiting dilution with A549 cells by observing cell cytopathic effect (CPE). To passage viral libraries without IFN treatment, ~10 million A549 cells were infected with individual mutant virus library at an MOI of 0.05. Cells were washed with PBS three times at 2 h post-infection. Viruses were collected at 24 h post-infection from supernatants, cleared of cell debris and stored at −80° C. in aliquots. For selection under exogenous type I interferon treatment, A549 cells were pre-treated with 1000 U/ml IFN-D2 (PBL Assay Science) for 20 h and then infected with viral libraries at an MOI of 0.05. Cells were washed with PBS three times at 2 h post-infection, and 1000 U/ml IFN-D2 was added back into culture media. Similarly, viruses were collected at 24 h post-infection from supernatants, clarified of debris and stored at −80° C. in aliquots.

d. Sequencing Mutant Libraries and Data Analysis

Sequencing libraries were prepared as previously described (21, 22). Briefly, viral RNA was extracted using QIAamp Viral RNA Mini Kit (Qiagen Sciences). DNaseI (Life Technologies) treatment was performed, followed by reverse transcription using Superscript III system (Life Technologies).

Real-time PCR was used to quantify viral copy number. At least 1×106 viral RNA copies were used to amplify the mutated fragment. The amplified fragment was then digested with BpuEI or BpmI and ligated with the sequencing adaptor, which had three-nucleotide multiplexing ID to distinguish among different samples.

Deep sequencing was performed with Illumina PE250. Raw sequencing reads were de-multiplexed using the three-nucleotide ID. Sequencing error was corrected by filtering out low quality reads (quality score <30) and un-matched base-pairs between forward and reverse reads. We achieved at least 20,000×sequencing coverage for each nucleotide position. Mutations were called by comparing sequencing reads with the wild-type sequence. Reads containing two or more mutations were excluded from the downstream analysis, which enables us to eliminate potential complications $$\text{RF score}_{mutant\ i}=\text{Relative Frequency of Mutant } i_{infection}/\text{Relative Frequency of Mutant } i_{plasmid}$$

Where Relative Frequency of Mutant i=Reads of Mutant i/Reads of wild type caused by multiple mutations. Relative fitness score (RF score) in each condition was calculated for individual mutations. To reduce sampling errors in the estimating relative fitness, only those mutations with frequency >0.05% in the input plasmid library were reported.

Where relative frequency of mutant i=reads of mutant i/reads of wild type.

All the data processing and analyses was performed with customized python scripts, which are deposited at https://github.com/YushenDu/Influenza-Vaccine e. Construction of Viruses with Specific Mutation(s)

Viruses with specific mutation(s) were generated using a PCR-based site-directed mutagenesis strategy. To reconstitute mutant viruses on WSN background, 1.5 million 293T cells were transfected with 4 Pg plasmid DNA. Transfections were performed using Lipofectamine 2000 (Life Technologies). Viruses were collected at 72 h post-transfection. Mutant viruses were further amplified in A549 cells. Supernatants were collected, clarified of debris and stored at −80° C. in aliquots. Viral titers were measured by a TCID50 assay with A549 cells. Virion RNA was extracted, and reverse transcribed to cDNA. Coding sequences of all mutants were PCR amplified, and subjected to Sanger DNA sequencing for confirmation. To measure growth kinetics of mutant viruses, ~1 million A549 cells were infected with each mutant virus at an MOI of 0.1 and supernatants were collected at indicated time. To generate mutants on PR8 background, 1.5 million 293T cells were transfected with 4 Pg DNA and co-cultured with MDCK cells. Media was changed to OPTI-MEM with 0.8 mg/ml TPCK Trypsin at 24 h post-transfection. Viruses were collected at 72 h post transfection. Viral titers were measured by TCID50 assay with MDCK cells. Mutant viruses were further amplified in MDCK cells, supernatants were collected, clarified of debris and stored at −80° C. in aliquots.

In one or more examples, using silent mutation as benchmark, we observed that on average, ~60% of missense mutations are deleterious for influenza viral replication and only ~2% are beneficial. Similarly to previous results, the high percentage of deleterious mutations suggested the general conserved nature of an RNA viral genome. However, different proteins in the influenza A genome also showed diverse levels of mutation tolerance. We quantified the average fitness cost as well as the percentage of lethal mutations of every viral protein. Polymerase subunits (PB2, PB1, PA and NP) are highly conserved while NS1 and M2 are relatively mutable.

f. Selection of Possible IFN Sensitive Mutations for Measuring IFN-Sensitivity Using Individually Constructed Mutant Viruses Because anti-IFN function of NS1 protein has been extensively studied, we focused on proteins (PB2, PB1, PA, NP, M1, M2) for further validation. To select possible IFN sensitive mutations, we followed the following criteria: 1) RF scores >0.7 in A549 cells without IFN selection; 2) RF scores <0.3 under interferon selection; 3) Residues that give similar interferon sensitive phenotypes when mutated into different amino acids were preferred. Moreover, we mapped the potential interferon sensitive residues onto protein structures (PDB: 4WSB, 1RUZ, 2IQH, and 1EA3) (38-40, 48-50) and preferentially selected the ones clustered on the protein surface for validation. Up to 7 mutations per segment were selected.

To measure IFN-sensitivity using individually constructed mutant viruses, 1 million A549 cells were pretreated with 1000 U/ml IFN-D2 (PBL Assay Science) for 20 h or left untreated. Then cells were infected with indicated virus at an MOI of 0.1. Cells were washed with PBS three times at 2 h post-infection, and 1000 U/ml IFN-D2 was added back into culture media. Supernatants were collected at 24 h post-infection and viral copy numbers were quantified by real-time PCR. Relative IFN-sensitivity for each mutant was calculated as the fold of viral copy number change with IFN selection, normalized to WT.

In one or more embodiments, well-known interferon sensitive mutations were captured by our interferon screen. For example, amino acids of RNA binding domain of NS1 protein, especially R37, R38, K41, R46 were shown to be highly interferon sensitive. This domain was reported to be important to sequester viral dsRNA from cytoplasmic RNA sensors and inhibit certain ISG functions. Our screen results correlate well with the reported key residues for this function.

g. Polymerase Activity Assay

Plasmid DNAs (100 ng of PB2, PB1, PA, and NP; 50 ng of virus-inducible luciferase reporter and 5 ng PGK-*Renilla* luciferase reporter) were co-transfected into 293T cells in 24-well plates (51). Cells were lysed at 24 h post-transfection and followed by the Dual-Luciferase Assay (Promega).

h. Immunofluorescence Assay

Intracellular localization of IRF3 protein was determined by immunofluorescence. Infected A549 cells were fixed in 2% paraformaldehyde, permeabilized with 0.1% Triton-X100, and blocked with 3% BSA and 10% FBS. Viral NP protein was detected with anti-NP monoclonal antibody (GeneTex). IRF3 was detected with anti-IRF3 rabbit polyclonal antibody (Cell signaling). Hoechst 33342 dye was used for staining DNA.

i. Cell Viability (CCK8) Assay

A549 cells were infected with WT, NS1 R38A/K41A or HIS virus at an MOI of 0.1 in 96-well plates. Mock infection were used as control. 72 h post-infection, CCK8 solution (VitaScientific) were added in each well and incubated for 4 h at 37° C. Signals were detected at OD 450 nm.

j. RNA-Seq Library Preparation and Sequencing

RNA-seq libraries were prepared using a modified method based on the ScriptSeq mRNA-Seq library preparation kit (Epicentre) (48). Multiplex sequencing was performed by 50 bp single-end read with Illumina HiSeq 2000 machine at UCLA Clinical Microarray Core. Raw reads were aligned to the human genome assembly (hg19) or the mouse genome assembly (mm10) using TopHat under default parameter (52, 53). Results were quantified by reads per million total reads (RPM). Differential expression analysis was performed with edgeR (54). Gene ontology enrichment analysis was performed through metascape (55). Genes related to certain cellular pathways were extracted from MsigDB (56,57).

k. Measuring Viral Replication in Mice

To measure viral replication, BALB/c mice were anesthetized with isoflurane (IsoFlo, Henry Schein) and intranasally inoculated with indicated virus in a volume of 30 Pl. Body weight loss was monitored daily for 14 days. To quantify viral growth in mouse lung tissues, mice were intranasally inoculated with indicated virus at a dose of 1×104 TCID50 and sacrificed at day 2 post-infection. DMEM was used as a control for infection. To quantify viral titer by TCID50, lung tissues were harvested, homogenized, and freeze-thawed three times to release the virus. To quantify the viral genome copy number, RNA was extracted from mouse lung tissues using Trizol (Thermo Fisher). Similarly, to quantify the viral growth kinetics and gene expression in mouse lung tissues, lung samples were collected at 2, 6, 24, 48 and 120 h post-infection. Viral copy number and gene expression was quantified by real-time PCR. All mice experiments were performed in accordance with the guidelines of the animal protocols approved by UCLA, CDC China, Trudeau Institute and University of Pittsburgh.

l. Measuring Pathogenesis in Mice

To determine the pathology and cytokine expression, BALB/c mice were intranasally inoculated with indicated virus at a dose of 1×104 TCID50. Bronchoalveolar lavage (BAL) and lung samples were collected at day 2 and day 9 post-infection. Albumin concentration in BAL was determined using mouse albumin ELISA Quantitation kit (Bethyl Alboratories) and cytokine response was analyzed by Lincoplex (BioRad). BAL cell cytospin slides were stained with a HEMA-3 stain kit (Fisher Scientific) for inflammatory cell differential counts. In addition, lung tissues were fixed with 10% neutral buffered formalin (EMD Millipore) and paraffin embedded for histology. Hematoxylin and Eosin (H&E) stained lung tissue slides were scored for their pathology with the following criteria (Score 1-5):

1=No Observable Pathology.

2=perivascular/peribronchus or lung parenchyma inflammatory infiltration <25% of the lobe section.

3=perivascular/peribronchus or lung parenchyma inflammatory infiltration 25%-50% of the lobe section.

4=perivascular/peribronchus or lung parenchyma inflammatory infiltration 50%-75% of the lobe section.

5=perivascular/peribronchus or lung parenchyma inflammatory infiltration >75% of the lobe section. Cytokines in BAL samples were measured by Bio-Plex Pro Mouse Cytokine 23-plex assay according to the product protocol (Bio-Rad)

m. Measuring Antibody and T Cell Responses in Mice

For measuring antibody responses, BALB/c mice were intranasally inoculated with the indicated virus at a dose of 1×104 TCID50. DMEM was used as a control. Mouse sera were collected at days 14, 21 and 28 post-infection. Sera and BAL samples were collected at day 28 post-infection. Sera were used for immunoglobulin G (IgG) antibody detection, hemagglutination inhibition and neutralization assays. BAL samples were used for immunoglobulin A (IgA) antibody detection.

To measure T cell response, C57BL/6J mice were intranasally inoculated with indicated virus at a dose of 1×104 TCID50. To examine primary T cell responses, lungs and spleens were harvested at day 10 post-infection. Fresh cells were used for tetramer staining and flow cytometry. For peptide stimulation of T cells, spleens were harvested at day 28 post-infection. To examine secondary T cell responses, lungs and spleens were harvested at 14 days post challenge of indicated virus at day 28 post-vaccination with HIS virus.

n. Protection from Challenging Infections in Mice

For protection studies, BALB/c mice were intranasally inoculated with the indicated virus at a dose of 1×104 or 1×106 TCID50. DMEM was used as control. Mice were then intranasally challenged with 1×104 TCID50 WT. Viral titers were quantified by both TCID50 and real-time PCR assays at day 2 post challenge.

To examine protection from homologous and heterologous viral challenges, C57BL/6J mice were intranasally vaccinated with HIS virus or PBS as a control. At day 28 post vaccination, A/PR8/34 (H1N1), A/Cal/04/09 (H1N1) and WSN (H1N1) were used for intranasal challenge at a dose of LD90 which was 6000 50% Egg Infective Dose (EID50), 8000 EID50 and 14,000 EID50 respectively. A/X-31(H3N2) was given at 45,000 EID50 (LD50) because it was difficult to reach LD90. Body weight loss was monitored twice daily for 14 days. The following clinical scores were used to quantify the clinical symptoms:

0=no visible signs of disease
1=slight ruffling of fur
2=ruffled fur, reduced mobility
3=ruffled fur, reduced mobility, rapid breathing
4=ruffled fur, minimal mobility, huddled appearance, rapid and/or labored breathing
5=found dead.

o. Enzyme-Linked Immunosorbent Assay (ELISA)

Viral protein specific IgG and IgA antibodies were detected using an enzyme-linked immunosorbent assay (ELISA). 96 well ELISA plates (Costar, Corning) were coated with 1 Pg/ml recombinant viral proteins (HA-WSN, HA-PR8, HA-HK68, HA-Viet04, NP, NA or M1) in bicarbonate/carbonate buffer (pH 9.5) at 4° C. overnight. Wells were washed with PBST between each step for 3-5 times. Wells were then blocked with 10% FBS in PBS for 1 h at room temperature. Serum or BAL samples were diluted in blocking buffer and added to wells for incubation at 4° C. overnight. HRP-conjugated anti-mouse IgG antibody (Cell Signaling) or HRP-conjugated anti-mouse IgA antibody (Thermo Fisher) was diluted in blocking buffer and added into wells for 1 h at room temperature. SIGMA FAST OPD (Sigma) was used to detect the signals at OD 450 nm.

Luminex multiplex assay was performed according to the manufacturer's protocol (Bio-Rad). IFN-D concentration in mouse BAL samples were determined using VeriKine Mouse Interferon Alpha ELISA kit (pbl Assay Science) according to the manufacturer protocol.

p. Hemagglutination Inhibition (HAI) Assay

Mouse sera were pre-treated at 56° C. for 30 min. 4 HA units of WT virus were incubated with 2-fold serially diluted sera at 37° C. for 1 h in V shaped 96-well plate. The starting concentration of sera was 1:4. Washed turkey red blood cells (Lampire) at a concentration of 0.5% were added into each well and incubated at room temperature for 30 min. The HA titer was then read as the highest dilution of serum that prevented hemagglutination.

q. Antibody Neutralization Assay

Mouse sera were pre-treated at 56° C. for 30 min. WT viruses were incubated with serial diluted serum at 37° C. for 1 h. Sera from mock-infected mice were used as control. Viral titer after incubation was measured by TCID50 assay using A549 cells.

r. Determining Mutations on HA Protein Non-Neutralized by Serum Antibodies

Dose response curve of mouse sera against WT viral replication was measured by an antibody neutralizing assay. Reconstituted mutant viral libraries on HA protein were incubated with individual mouse serum (5 mice from WT vaccinated group and 5 mice from HIS vaccinated group) at the concentration of IC80 at 37° C. for 1 h. Sera from unvaccinated mice were used as mock control. After incubation with a serum, mutant libraries were used to infect 30 million A549 cells, and washed with PBS twice at 2 h post-infection. Corresponding serum was added back into the culture media that matched IC80. Supernatants were collected at 48 h post-infection, viral RNA was extracted and reverse transcribed. The relative frequency of each mutant was determined by Illumina MiSeq PE250 as described before.

For each mouse serum selection condition, relative enrichment scores (RE scores) of HA point mutations were calculated by comparing the relative frequencies of the mutations with and without serum selection.

RF score$_{mutant\ i}$=Relative Frequency of Mutant $i_{serum}$/Relative Frequency of Mutant $i_{plasmid}$ Where Relative Frequency of Mutant i=Reads of Mutant i/Reads of wild type.

Mutations with RE score >5 and with RF scores >0.05 were classified as non-neutralized mutations by the corresponding serum antibodies. Mutations that occurred in at least two mouse sera in the WT or HIS group were selected and compared.

s. Quantitation of Viral-Specific CD4 T Cells

Splenocytes were stimulated with WT WSN virus for 16 h at 37° C. with the presence of 1 Pg/ml brefeldin A. Cells were stained with CD3-efluorofore450, CD4-FITC and intracellularly stained with IFNJ-PE. Percentage of IFNJ positive CD3+CD4+ cells was quantified by flow cytometry.

t. Determining the Usage of T Cell Receptor Repertoire

The TCRE loci of influenza NP366-374 specific CD8 T cells from both primary and secondary responses were deep sequenced. For the primary response, mouse lung and spleen tissues were harvested at day 10 post-infection. For the secondary response, vaccinated mice were challenged with WT virus at day 28 post-infection, and tissues were harvested at day 10 post-challenge. To isolate NP-specific CD8 cells, mouse lung and spleen tissues were harvested and single cell suspensions were generated. T cell population was enriched using the EasySep mouse T cell isolation kit (Stemcell) and stained with CD3-efluorofore450, CD8a-FITC and NP366-374 tetramer conjugated with PE. NP positive CD8 T cells were sorted out by FACS. A total of 18 samples were deep sequenced (Adaptivebiotech), including 10 mice for the primary response (5 for WT vaccination and 5 for HIS vaccination), and 8 mice for the secondary response (4 for WT vaccination and 4 for HIS vaccination). VDJ recombination was analyzed for each sample by immunoSEQ Analyzer. Clonality was calculated for NP-specific T cells as the inverse of the normalized Shannon's entropy.

u. Determining Viral Replication and Protection Effects in Ferrets

Ferret experiments were performed in ABSL-2 laboratory in the animal facility at Center for Disease Control and Prevention, China. All animals were determined to be sero-negative by HAI to circulating seasonal influenza viruses. To evaluate the replication of HIS and WT viruses, 18 ferrets were divided into 3 groups (6 ferrets each) and intranasally inoculated with 500 Pl of 1×106 TCID50 HIS or WSN. PBS was used as control. Body weight, body temperature and clinical symptoms were observed and recorded daily. At days 1, 3, 4, 7, 9 and 14 post-inoculation, nasal washes and rectal swabs were collected in 1.5 ml PBS. At day 3 post-inoculation, 3 ferrets in HIS or WSN groups and 1 ferret in PBS group were euthanized and tissue specimens (lungs, tracheas and turbinates) were collected.

To evaluate protection efficiency, 8 ferrets were inoculated with $1\times10^6$ TCID50 HIS. PBS was used as control. At day 35 post-inoculation, ferrets were intranasally challenged with either $1\times10^7$ TCID50 A/WSN/33 (H1N1) or $1\times10^6$ TCID50 A/California/07/09 (H1N1pdm) respectively. Body weight, body temperature and clinical symptoms were recorded daily. At days 1, 3, 4, 7 and 9 post challenge, nasal washes and rectal swabs were collected in 1.5 ml PBS. At day 3 post challenge, 2 ferrets in each group were euthanized. Tissue specimens (lungs, tracheas and turbinates) were collected and homogenized in 1 ml of PBS using stainless steel balls and a tissue lyser (TissueLyserII QIAGEN) operated at 25 Hz for 5 mins. Viral titers in supernatants of homogenized tissues, nasal washes and rectal swabs were examined using TCID50 on MDCK cells. Ferret experiments were approved by Animal Ethics Committee of National Institute for Viral Disease Control and Prevention, China.

v. Viral Titer Assay for Ferret Experiments

Viral titers (TCID50) of nasal washes, rectal swabs and tissue samples were detected in MDCK cells with virus culture medium containing 2 μg/ml TPCK-trypsin in 96-well flat-bottom cell culture plates. 50 μl of serial one-half log 10 dilutions for nasal washes and rectal swabs, or 10 fold dilutions for tissue samples were added to MDCK cells and incubated at 37° C. for 1 hour. 100 μl of virus culture medium was added to each well and incubated at 37° C. for 18 to 20 h. Cells were fixed by precooled 80% acetone for 10 mins, followed by ELISA using 1:4000 anti-influenza A NP monoclonal antibody pool (IRR) and 1:2000 goat anti-mouse IgG conjugated with HRP (KPL). Each sample was titrated in triplicate. TCID50 of each sample was calculated by the Reed Muench method.

w. Analyzing Fitness Cost of Mutations in T Cell and Antibody Epitope Regions

T cell epitopes, linear antibody epitopes and conformational antibody epitope sequences were extracted according to the Immune Epitope Database and Analysis Resource (IEDB) (58). We included the epitopes that with conservation >90% for WSN virus for analysis. For T cells epitopes, only human epitopes were considered. The RF scores for mutations within or outside of epitope regions were compared.

x. Mapping onto Protein Structures, Gene Expression, Viral Replication, Polymerase Activity, We mapped the list of potential interferon sensitive residues onto protein structures. We reasoned that if a residue is interacting with interferon pathway, then it is more likely to be located on the exposable surface. Moreover, it is likely that multiple mutations around the same domain or same pocket showed a similar phenotype. For example, we observed two clusters of interferon sensitive mutations, located on the N terminus of PB2 protein and M1 protein, respectively. Thus, we preferably picked the residues that clustered on the protein surface for validation (FIG. 1D). We constructed 24 single mutations in total and examined their interferon sensitivity in the context of viral replication. R38A-K41A double mutations on NS1 were introduced as positive control. We first evaluated the viral replication of these mutations by infecting A549 cells with MOI 0.1. TCID50 were quantified at 48 h post infection. All the mutations showed to be neutral or nearly neutral for viral replication. Furthermore, we measured the polymerase activity for the mutations in polymerase complex (PB2, PB1, PA and NP) by minigenome replicon assay. Consistent with viral growth, the polymerase activity of the selected mutations are all nearly intact. We further examined the interferon sensitivity of these mutations by infecting them with A549 cells with and without interferon selection. Compared with wild type WSN virus, all the mutants showed higher sensitivity, as the decrease of viral growth is more significant under interferon selection. Although not as dramatic as R38A-K41A mutation on NS1, 8 out of the 24 mutations on internal genes showed higher interferon sensitivity compared with wild type. 8 out of them showed significant higher interferon sensitivity.

To further examine if each mutant can induce higher interferon production or is deficient in inhibiting interferon response, we infected A549 cells at MOI=1 with different mutants and examined gene expression at 6 h post infection by RT-qPCR. Compared with wild type, the three mutations on PB2 (N9D, Q75H, T76A) and three mutations on M1 (N36Y, R72Q, S225T) induced significantly higher IFN-β gene expression (FIG. 1F). The induction can be more dramatically seen with ISG54, a target gene of IRF3 same with IFNb. We also examined the nuclear translocation of IRF3 post infection. Consistent with gene expression results, these 6 mutations that induce higher IFNb expression also induce strong nuclear translocation of IRF3, indicating a stronger IFN production and response. The higher induction of IFN is MAVS dependent and Sting independent, as knocking out MAVS would abolish the induction while no effect with STING knockouts. These results suggested that the three mutations on PB2 (N9D, Q75H, T76A) and three mutations on M1 (N36Y, R72Q, S225T) might lose the function of inhibiting interferon production at early time points post infection. The other two mutations (PB1 L155H, PA E181D), however, did not induce higher interferon production. These two mutations are still IFN sensitive in vero cells which have defect in IFN production, indicating that they might loss the inhibition of downstream interferon pathway (JAK-STAT pathway or ISG functions). siRNA screening or cDNA overexpression screening of JAK-STAT pathway or ISGs can be performed to identify the cellular factor interacting with the mutants.

y. Safety, Efficiency, and In Vitro Growth

Safety and efficiency are two major considerations for vaccine development. Combinations of interferon sensitive mutations generate a virus that is more sensitive to interferons, and enables exploration of potential use as live attenuated vaccine candidate. On one hand, the interferon sensitive phenotype would make the virus highly attenuated in vivo, on the other hand, the higher induction of interferon system might induce stronger adaptive immune response. Moreover, as the combination of multiple mutations are located in different gene segments and are mostly neutral for viral replication without interferon selection, the risk of a revertant due to do novo mutation or gene assortment is greatly reduced.

Another important consideration for generating a live attenuated vaccine candidate is the capacity of viral growth in vitro. The strain should retain sufficient growth capacity in order for mass production. Thus, to generate a combination strain, we first picked those that can induce higher interferon production, then we tried to add additional interferon sensitive mutations while preserving the viral replication capacity in vitro. After testing a plurality of combinations, we selected one of the combinations, which we called HIS strain. It contains 3 mutations from PB2 (N9D, Q75H, T76A), three mutations on M1 (N36Y, R72Q, S225T), and two mutations on NS1 (R38A, K41A). HIS virus is highly sensitive to interferon treatment (FIG. 2C). The interferon sensitivity is significantly higher than NS1 mutations (R38A-K41A), indicating the accumulative effect of mutations on PB2 and M1. We also quantified the viral growth of WT, NS1 mutant and HIS virus in IFN competent A549 cells and IFN deficient vero cells by TCID50 assays. The HIS virus showed about 2 log attenuation compare with WT in A549 cells, which is more deleterious than NS1 double mutations alone. However, the growth of HIS virus is restored in Vero cells, which grow at similar speed and reach similar peak viral load compared with wild type cells. HIS virus induced higher interferon production and response in A549 cells (FIG. 2D,I). At an early time point after infection (6 h), it can induce higher IFNb and ISG54 gene transcription. And at 24 h post infection, the induction of certain ISGs (ISG15, IFI6, RIG-I, Mx1) is also significantly higher than wild type. To examine the global change in gene transcription, we performed mRNA sequencing for WT, NS1 R38A-K41A HIS and mock control virus infected A549 cells at 6 h post infection. Biological duplicates were performed. Raw reads were aligned to human genome assembly, and the expression levels of individual genes were expressed as reads per million total reads (RPMs). An Edge package was used for statistical analysis. Compared with mock infected cells, 381 genes are significantly upregulated (fold change >2 and p<0.01) for HIS infected cells (FIG. 2E), and 181 genes are downregulated. Gene Ontology (GO) enrichment analysis of the upregulated genes revealed that the type I interferon production and response related genes are highly enriched. Top 4 GO terms are all related to interferon related defense response. Up-regulation of interferon production and ISGs are more significant in HIS compare with NS1 mutations. This suggested the key difference for cellular response of HIS and wild type virus relies on the ability of induce interferon response.

To examine if the IFN sensitive phenotype of HIS virus is independent of WSN background, we introduced the same 8 mutations into a PR8 background. As expected, HIS virus on the PR8 background also showed higher IFN sensitivity than WT PR8 or NS1 mutations.

We next investigated the replication and pathogenesis of HIS virus in a mouse model. 6-8 weeks Balb/c mice were intranasal inoculated with WT virus or HIS virus at a dose of $10^5$ or $10^6$ TCID50. Body weight loss was monitored daily for 10 days. $10^6$ TCID50 WT virus resulted in significant weight loss of all animals, while same amount of HIS did not cause weight loss. $10^5$ TCID50 WT virus caused very mild (~5%) weight loss and quickly recovered. Thus, we consistently used $10^5$ TCID50 as the vaccination dose for further studies.

The only FDA-approved LAIV is a recombed virus with internal (PB2, PB1, PA, NP, M and NS) segments derived from A/Ann Arbor/6/60 (H2N2) that is cold adapted, therefore temperature sensitive (TS) and attenuated. The temperature-sensitive phenotype comes form 5 mutations in 3 polymerase genes: PB1 (391E, 581G, and 661T), PB2 (265S), and NP (34G). Similar phenotypes can be achieved in different strains by introducing the same mutations, including A/WSN/33 strain that we used here. Thus, we constructed and used the temperature sensitive WSN (WSN-TS) strain as control. We further investigated the viral replication in lungs of vaccinated mice. Viral titers of mice lung were quantified by TCID50 and viral copy number at day 2 post vaccination (FIG. 3L). Replication of the HIS virus was significantly lower than WT and NS1 R38A-K41A mutation, and comparable with WSN-TS virus. We also performed a time scale viral replication assay for HIS and wild type virus. Mice lung samples were collected at 2, 6, 24, 48 and 120 hours post vaccination and viral copy number were quantified. WT virus showed robust viral replication with viral peak at 48 h. In contrast, HIS virus only showed very limited replication at early time points followed by steady decay of copy number in lung tissues. It suggested HIS virus is highly attenuated in animal models, which is safe as a vaccine candidate. To examine if the attenuation is due to IFN sensitivity, we further tested viral replication in IFNAR-/- mice. The replication of HIS virus was fully rescued back to a WT level in IFNAR-/- mice, indicating that competent IFN response attenuates HIS virus in wild type mice (FIG. 3M).

To further examine global gene transcription change upon infection in vivo, we performed mRNA sequencing of lung samples at 6, 24, 48, 120 hours post infection of HIS and WT virus. Compared with mock infected controls, the IFN pathway was most significantly upregulated at 48 h post infection for wild type virus, correlated with viral replication. Although highly attenuated in replication, HIS virus also showed early but significant upregulation of certain IFN related genes (FIG. 3E,F). The upregulation is most obviously seen in 6 h and 24 h post infection.

z. Adaptive Immune Responses and Protection

As the HIS virus is highly attenuated in vivo, we then examined if it still can induce robust adaptive immune response for protection. We first evaluated the humeral response. Balb/c mice were intranasal infected with $10^5$ TCID50 WT and HIS virus. At 14, 21 and 28 days post infection, serum samples were collected and HA-specific antibody were assessed through ELISA. We purified 4 types of HA protein from different strains of virus: WSN, PR8, HK68, and Viet04. WSN and PR8 belong to H1, HK68 is H3, and Veit04 is H5. According to the classification of HA proteins, H1 and H5 are class I, while H3 belongs to class II. Specific antibodies were detected for both WT and HIS vaccinated mice at all three time points against WSN, PR8 and Veit04 HA protein. The antibody titer kept increasing throughout the days post infection. HIS virus elicits a lower amount of specific antibodies compared with WT, majorly due to the attenuated replication. Notably, the antibody against HK58 HA was under the detection limit for both the WT and HIS virus using ELISA assay, suggesting there might be limited antibody that can recognize conserved epitope across class I and II HA. We also performed neutralization assay by hemagglutinin inhibition (HI) assays (FIG. 4E). 8 HA unit of WSN virus was incubated with serial dilution of heat inactivated serum in 37 degree for 2 h followed by the examination of HI ability. Consistent with ELISA result, the HIS virus elicits a significant amount of neutralizing antibody, although not high as WT.

We then examined the ability of the HIS virus to induce T cell response. 6-8 week female C57/B6 mice were infected with $10^5$ TCID50 of WT and HIS virus or mock infected with DMEM. A Single cell suspension was prepared from mice lung samples and T cell responses were examined by tetramer staining. HIS virus developed similar levels of NP-specific T cells compared with WT although the replication was three logs lower. Furthermore, we evaluate the memory T cell response 1 month post vaccination by peptide stimulation assay. Solenocytes were incubated with viral peptide of known epitopes overnight and the amount of IFN-g secreting CD8 T cells were quantified by intracellular cytokine staining. Again, similar levels of memory T cell response were observed between HIS and WT vaccinated mice. These results suggested HIS stimulate more robust T cell responses because of the knockout of immune evasion functions.

Figure 4Q:
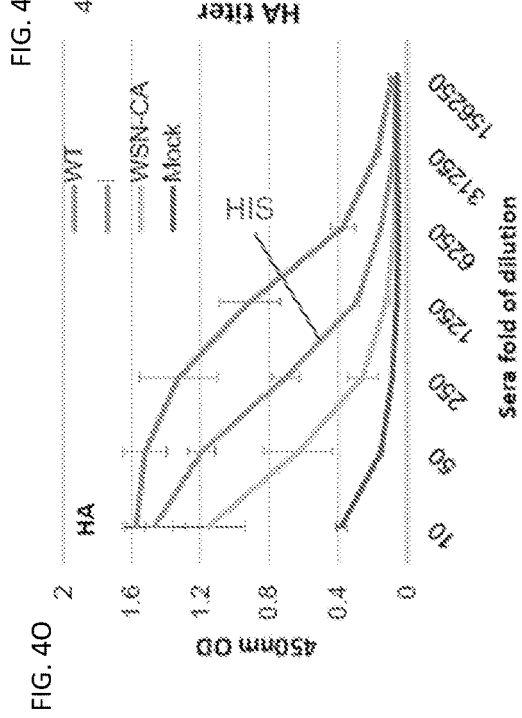
Figure 4S:
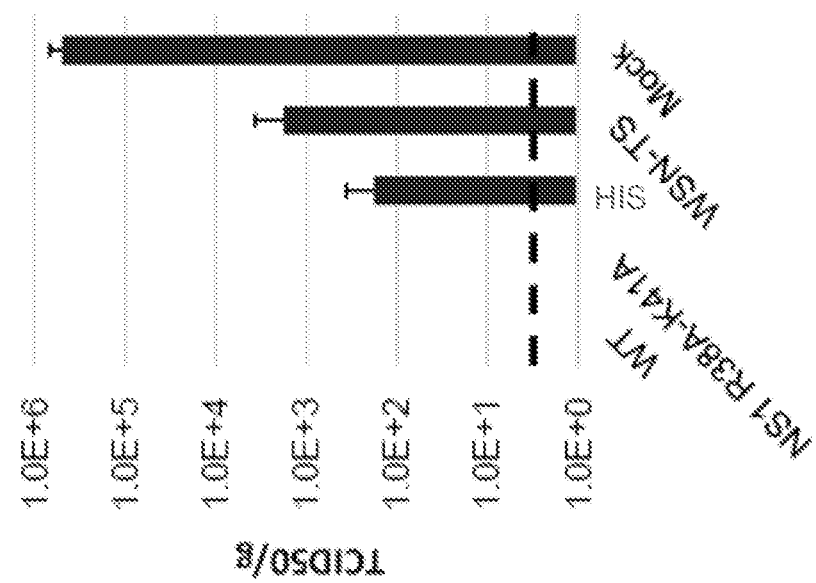
Figure 4R:
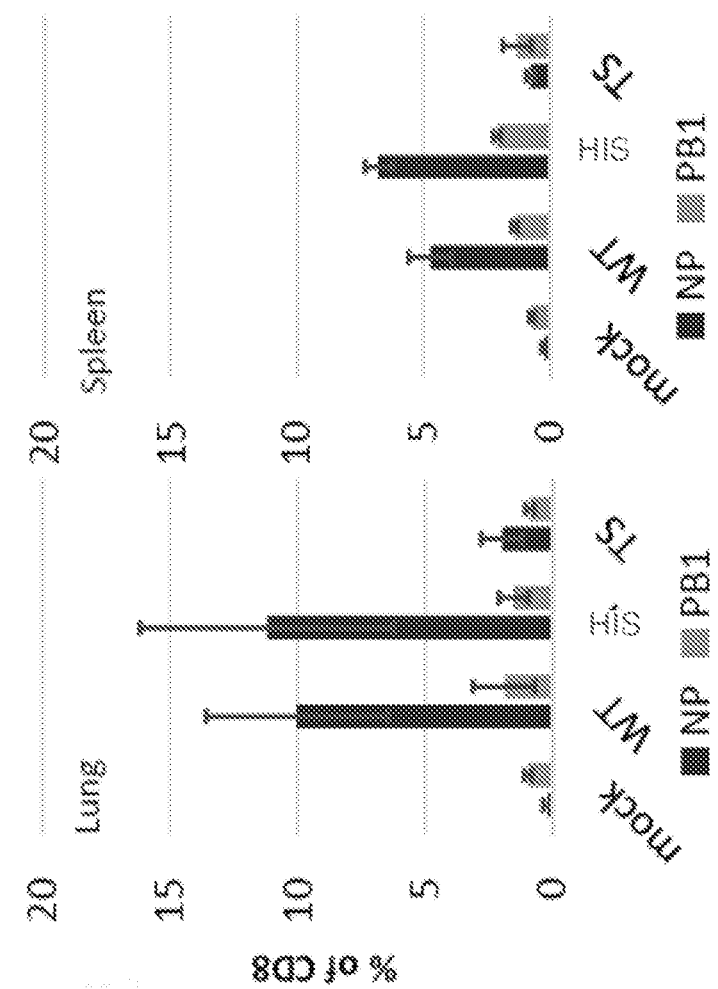

Finally, we examined if HIS virus can protect mice from challenges. 6-8 week female C57/B6 mice were intranasal vaccinated with $10^5$ TCID50 of WT, NS1 R38A-K41A, HIS, WSN-TS virus or mock infected with DMEM. 4 mice were used per group. All mice were challenged with $10^5$ TCID50 of WT virus 21 days post vaccination and viral titer in lung tissues were quantified at day 2 post challenge. By both RT-qPCR and TCID50 assay, we observed a ~3 log titer drop in HIS vaccinated mice compare with mock vaccination. The decrease of viral titer is more significant than WSN-TS vaccinated group (FIG. 4Q).

We then challenged the HIS vaccinated mice with three heterologous strains (PR8, ACal/04/09 and X31) at lethal dose. Strong protection was seen across the board in terms of survival rate, percentage of body weight loss, and clinic scores (FIG. 5D, E).

Although NS1 is the best studied IFN antagonist in influenza genome, the anti-IFN function has been recently appreciated in other proteins. It is reported that PB2 and PB1F2 could bind to MAVS and inhibit interferon production; ESIE motif in PB1 and PA can mediate type I interferon response, and NP of newly emerged H7N9 can counteract anti-viral ISG: MxA. Here, using a high-throughput genetic approach, we have identified multiple IFN sensitive mutations in the PB2, PA, PB1 and M1 proteins, suggesting the anti-IFN functions of corresponding WT proteins. As anti-IFN functions are essential for efficient viral replication in vivo, it is reasonable that the functions are distributed in different segments. Identified IFN sensitive mutations also work on different parts of IFN system. Mutations on PB2 and M1 can induce higher IFN production, indicating that they work at the upstream of IFN system. On the other hand, mutation on PB1 and PA cannot induce higher IFN production and response, and the sensitivity still remains in IFN deficient Vero cells, suggesting that they might be interacting with JAK/STAT pathway or a specific anti-viral ISG.

III. Process Steps a. Identifying Interferon Sensitive Mutations Using a Genetic Platform To systematically identify interferon sensitive mutations across the entire influenza genome, we performed the interferon selection using a high-throughput genetic platform.

FIG. 26 is a flowchart illustrating a method of making a genome using a genetic platform.

The method comprises the following steps.

Block 2600 represents optionally constructing a mutant plasmid library.

In one example, a mutant plasmid library was constructed on the backbone of influenza A/WSN/1933 (H1N1) strain. In order to control mutant library size, the entire viral genome was divided into 240 bp small fragments, and error-prone polymerase was used to introduce random mutations into each small fragment so as to generate a mixed mutant population. In one or more examples, each resulting plasmid population is considered a mutant plasmid library, with ~1000 different mutations, and total of 52 plasmid libraries are established to cover the whole genome.

Block 2602 represents co-transfecting a mutant DNA library with a plurality of plasmids encoding different fragments of a pathogen genome, so as to form a mutant pathogen library. In one or more examples, 30 million 293T cells are transfected with the DNA library together with seven other wild type plasmids to reconstitute the mutant virus library.

Block 2604 represents passaging the mutant pathogen library in host cells with and without interferons, so as to form a plurality of first infected segments obtained from the passaging with the host cells with the interferons and a plurality of second infected segments obtained from the passaging with the host cells without the interferons. In illustrative embodiments described herein, the mutant viral library was passaged in A549 cells under interferon selection at a concentration of 1000 U/ml, virus was collected 24 h post selection, and biological duplicates were also conducted. In one or more examples, 15 million A549 cells were used to passage the viral library with MOI 0.05 for 24 h. In one or more examples, biological duplications are conducted for both transfection and infection steps.

Block 2606 represents gene sequencing each of the infected segments so as to identify single nucleotide mutations or one or more nucleotide mutations.

Block 2608 represents calculating a relative fitness score (RF score) of each single nucleotide mutation, or each of one or more of the nucleotide mutations, in each of the infected segments, wherein the RF score is a ratio of a frequency of the single nucleotide mutation or one or more nucleotide mutations in the infected segment/infection library as compared with the mutant DNA library. For example, the relative fitness (RF) score of a mutant virus may be calculated as the ratio of the relative frequency in the selected virus library to that in the plasmid library. In one or more examples, ~90% of nucleotide positions across the genome were covered, and ~95% of single mutations were detected in the DNA library. In one or more embodiments, to further increase the measurement of viral fitness, filtering was performed to identify mutations that only occur <0.05% in the input library. In one or more embodiments and silent mutations form a normal distribution with RF score centered around 1. In one or more examples, there is a clear separation between silent mutations and lethal mutations, suggesting sufficient selection during passage.

Furthermore, in one or more embodiments, interferon sensitivity may be calculated as the difference of relative fitness with and without interferon selection, and correlation between biological duplicates may be observed.

Block 2610 represents selecting the mutations having an RF score less than 0.2 in the first infected segments and the RF score greater than 0.5 in the second infected segments, so as to form selected mutations. In one or more examples, the basic criteria for selection include RF scores of fitness >0.5; RF scores of fitness under interferon selection <0.2; and preferring residues that give similar interferon sensitive phenotypes when mutated into different amino acids.

Block 2612 represents forming the genome comprising the selected mutations. The genome composition of matter may be embodied in many ways, including, but not limited to, the following embodiments listed below.

1. A genetically engineered pathogen genome, wherein, as compared to wild type pathogen, the genetically engineered genome comprises a combination of nucleotide mutations selected to (1) increase the pathogen's sensitivity to type I interferon, and (2) induce an antibody and/or T cell response to the pathogen when used as an immunogen in vivo that is at least 10% of the antibody and/or T cell response induced when a wild type pathogen genome lacking the plurality of mutations is used as an immunogen in vivo; or suppress replication of the pathogen in a host cell in the presence of type I interferon by at least 50% as compared to replication of the pathogen in the host cell in the absence of the interferon. This genome composition of matter may be embodied in many ways, including, but not limited to, the following embodiments listed below.

2. The composition of matter of embodiment 1 wherein the combination suppresses replication of the pathogen in the host cell comprising interferons by a factor, e.g., of at least 10, at least 100, or by a factor in a range of 10-1000, as compared to replication in the host cell without the interferons.

3. The composition of matter of any of the previous embodiments 1-2, wherein the combination comprises nucleotide mutations each having a relative fitness score (RF) of less than 0.2 in the host cell comprising interferons and the RF score of greater than 0.5 in the host cell without the interferons, the RF score defined as a ratio of a frequency of the nucleotide mutation in the host cell as compared a frequency of the nucleotide mutation in a mutant DNA library.

4. The composition of matter of any of the preceding embodiments 1-3, wherein the pathogen is an influenza A virus and the combination at least sustains the antibody response to the virus.

5. The composition of matter of any of the preceding embodiments 1-4, wherein the mutations do not comprise mutations that only occur in less than e.g., 0.1% or 1% or 0.1%-5% of the mutant DNA library.

6. The composition of matter of any of the preceding embodiments 1-5, wherein each of the nucleotide mutations are located in different segments of the genome.

7. The composition of matter of any of the preceding embodiments 1-6, wherein the combination is selected from a set of mutations at, e.g., >50%, >60%, >70%, >80%, >90%, or 50-95% of the nucleotide positions in the genome.

8. The composition of matter of any of the preceding embodiments 1-7, wherein the nucleotide mutations comprise single, double, or triple nucleotide mutations, so that the combination is selected with single, double, or triple nucleotide resolution.

9. The composition of matter of any of the preceding embodiments 1-8, wherein the nucleotide mutations alter an amino acid sequence of a polypeptide encoded by the genome (e.g., with single amino acid resolution, e.g., so that a protein can be encoded with single amino acid resolution).

10. The composition of matter of any of the preceding embodiments 1-9, wherein the combination comprises e.g., at least 4 nucleotide mutations, at least 5 nucleotide mutations, at least 6 nucleotide mutations, at least 7 nucleotide mutations, or a number of nucleotide mutations in a range of 4-8.

11. The composition of matter of any of the preceding embodiments 1-10, wherein the pathogen is an influenza virus (e.g. influenza A).

12. The composition of matter of embodiment 11, wherein the pathogen is an influenza A virus, and the influenza A virus genome encodes a mutation comprising at least one amino acid substitution in PB2 at amino acid position N9, Q75 or T76; at least one amino acid substitution in M1 at amino acid position N36, R72 or S225, and/or at least one amino acid substitution in NS1 at amino acid position R38 or K41.

13. The composition of embodiment 12, wherein the pathogen is an influenza A virus, and the influenza A virus genome encodes a mutation comprising at least one amino acid substitution in PB2 selected from N9D, Q75H and T76A; at least one amino acid substitution in M1 selected from N36Y, R72Q and S225T, and/or at least one amino acid substitution in NS1 selected from R38A and K41A.

14. The composition of matter of any of the preceding embodiments 1-13, wherein the pathogen comprises a protein including residues and the genome encodes the protein so as to form clustered residues on a surface of the protein.

15. The composition of matter of any of the preceding embodiments 1-14, wherein the genetically engineered genome comprises a combination of nucleotide mutations selected to suppress replication of the pathogen in a host cell in the presence of type I interferon so that vaccination of a mouse with $1 \times 10^7$ pfu of the composition of matter does not result in death of the mouse.

Block 2614 represents optionally fabricating a vaccine, therapeutic agent, or other pharmaceutical composition comprising the composition of matter of Block 2612.

Thus, FIG. 26 further illustrates a method of making a genome, comprising systematically identifying immune evasion functions of a genome; and eliminating the immune evasion functions so as to tune a replication fitness of the genome and an antibody response to a pathogen comprising the genome.

Exemplary approaches described herein can be used to identify mutations that impact the production of INFs and the sensitivity to IFNs at single nucleotide or single amino acid resolution. In one or more embodiments, the high resolution enabled us to re-engineer the virus with precision that was not previously possible. For example, we are able to rationally change one amino acid at a defined location. Deletion mutation, on the other hand, as described in U.S. Pat. No. 9,387,240 (50) may impact other functions of the viral protein. However, as illustrated herein, we identified and utilized (e.g., 8) mutations that are different from the mutations described in the U.S. Pat. No. 9,387,240 (50). Each of the 8 mutations are very specific for INF induction and do not impact other functions. Moreover, the embodiments of the influenza A mutant described in the examples section herein are strongly suppressed in vivo and did not result in any death of vaccinated mice even at $1 \times 10^7$ pfu. However, the U.S. Pat. No. 9,387,240 (50) describes 2 mice were dead after being vaccinated with NS1-99 at $5 \times 10^6$ pfu.

b. Method of Fabricating a Composition of Matter and Generating an Immune Response FIG. 27 illustrates a method of making a composition of matter, e.g., including the composition of matter of block 2612 in FIG. 26.

Block 2700 represents mutating the genome of the wild type influenza A virus so as to generate an influenza A viral genome having a plurality of mutations selected to (a) increase the influenza A virus sensitivity to type I interferon; and (b) induce an antibody and/or T cell response to the influenza A virus when used as an immunogen in vivo that is at least 5%, 10% 25% or 50% of the antibody and/or T cell response induced when a wild type influenza A viral genome lacking the plurality of mutations is used as an immunogen in vivo.

Block 2702 represents the end result, a composition of matter comprising an influenza A viral genome having a plurality of mutations selected to (a) increase the influenza A virus sensitivity to type I interferon; and (b) induce an antibody and/or T cell response to the influenza A virus as described in Block 2700. This genome composition of matter may be embodied in many ways including, but not limited to, the examples listed below.

1. The composition of matter, wherein at least one of the plurality of mutations is at least one single nucleotide mutation in the influenza A: PA, PB1, PB2, NS1 or M1 genes.
2. The composition of any of the preceding embodiments, wherein the at least one mutation is found at amino acid position N9, Q75, or T76 in PB2, and/or found at amino acid position N36, R72, 5225 in M1, and/or found at acid position R3A, K41 in NS1.
3. The composition of any of the preceding embodiments 1-2, wherein the at least one mutation is selected from at least one of N9D, Q75H, T76A in PB2, and/or selected from at least one of N36Y, R72Q, S225T in M1, and/or selected from at least one of R38A, K41A in NS1.

The method illustrated in FIG. 27 can be used to generate an immune response to influenza A in a human, a pig or a bird (e.g. a duck) by administering to the human, a pig or a bird a composition as disclosed herein.

Advantages and Improvements

With rapid genome replication, high mutation rate and genome assortment, influenza viruses constantly evolve and adapt to diverse selection pressures, including different host responses. The type I interferon system (IFN), one of the most critical components of innate immune responses, plays essential roles for limiting influenza replication. It is also the bridge between innate immune responses and adaptive immune responses. Determining which viral proteins, more specifically which domain or residues are involved in managing interferon responses, is crucial for better understanding the mechanisms of viral-host interactions and informative for vaccine design.

As these proteins are essential for viral replication, generating mutations is the most direct way to examine their potential anti-IFN function in the context of viral replication. Specifically, using the fact that type I IFN system is the key player of innate immune response, we engineered a virus to be IFN sensitive by mutating IFN evasion genes and so as to efficiently attenuate the virus in vivo. As the IFNs are critical for the development of T cell and B cell response, the IFN inducing strains used as a vaccine stimulated a more robust adaptive immune response (despite reduced replication of the virus). Moreover, the anti-IFN functions of the virus are usually on multi-loci: by selecting a combination of mutations that are introduced into the vaccine strain, the level of replication and the ability to induce protective immune response can be fine tuned in order to maximize the efficacy and limit the risk.

Finally, since NS1 is the major IFN counteracter among influenza genome, different versions of the truncated NS1 protein (deltaFlu) are also being used as vaccine candidates and show impressive CD4, CD8 T cell development and antibody production. However, one limitation is that by focusing on one protein, there is risk of a revertant by gene reassortment. Embodiments of the present invention, on the other hand, use a genome wide screen to systematically identify IFN sensitive mutations across the whole genome that are neutral in viral replication. By combining together multiple mutations located in different gene segments, the risk of a revertant due to do novo mutation or gene assortment is reduced while maintaining the efficiency of vaccination.

Thus, we disclose here a framework for developing a live attenuated vaccine: systematically identifying immune evasion functions on the virus genome, then eliminating the immune evasion functions while maintaining and/or tuning the replication fitness. This systematic method is a generally applicable way for developing live attenuated vaccines and/or therapeutic agents that stimulate antibody responses to viruses in general (including, but not limited to, influenza, Zika, and NiV viruses) as well as other types of pathogens. A therapeutic agent comprising a pathogen genetically engineered according to the method(s) described herein would be particularly useful for patients infected with drug resistant virus and such a patient population would be suitable for the first group of clinical trials. Moreover, the method(s) described herein are suitable for use in human and agricultural (e.g., poultry, pig) applications.

Further information on one or more embodiments of the present invention can be found in reference (47).

IV. Sequences for Proteins and Viruses Described Herein.

```
a. Influenza A WSN strain HIS according to embodiments of
the present invention First segment (WSN flu1)
                                                        (SEQ ID NO: 1)
TCAATTATATTCAATATGGAAAGAATAAAAGAACTAAGGAATCTAATGTCGCAGTCTCGC

ACTCGCGAGATACTCACAAAAACCACCGTGGACCATATGGCCATAATCAAGAAGTACACA

TCAGGAAGACAGGAGAAGAACCCAGCACTTAGGATGAAATGGATGATGGCAATGAAATAT

CCAATTACAGCAGACAAGAGGATAACGGAAATGATTCCTGAGAGAAATGAGCAGGGACAA

ACTTTATGGAGTAAAATGAATGACGCCGGATCAGACCGAGTGATGGTATCACCTCTGGCT

GTGACATGGTGGAATAGGAATGGACCAGTGACAAGTACAGTTCATTATCCAAAAATCTAC

AAAACTTATTTTGAAAAAGTCGAAAGGTTAAAACATGGAACCTTTGGCCCTGTCCATTTT

AGAAACCAAGTCAAAATACGTCGAAGAGTTGACATAAATCCTGGTCATGCAGATCTCAGT

GCCAAAGAGGCACAGGATGTAATCATGGAAGTTGTTTTCCCTAACGAAGTGGGAGCCAGG

ATACTAACATCGGAATCGCAACTAACGACAACCAAAGAGAAGAAAGAAGAACTCCAGGGT

TGCAAAATTTCTCCTCTGATGGTGGCATACATGTTGGAGAGAGAACTGGTCCGCAAAACG
```

-continued

AGATTCCTCCCAGTGGCTGGTGGAACAAGCAGTGTGTACATTGAAGTGTTGCATTTGACC

CAAGGAACATGCTGGGAACAGATGTACACTCCAGGAGGGGAGGCGAGGAATGATGATGTT

GATCAAAGCTTAATTATTGCTGCTAGAAACATAGTAAGAAGAGCCACAGTATCAGCAGAT

CCACTAGCATCTTTATTGGAGATGTGCCACAGCACGCAGATTGGTGGAATAAGGATGGTA

AACATCCTTAGGCAGAACCCAACAGAAGAGCAAGCCGTGGATATTTGCAAGGCTGCAATG

GGACTGAGAATTAGCTCATCCTTCAGTTTTGGTGGATTCACATTTAAGAGAACAAGCGGA

TCATCAGTCAAGAGAGAGGAAGAGGTGCTTACGGGCAATCTTCAGACATTGAAGATAAGA

GTGCATGAGGGATATGAAGAGTTCACAATGGTTGGGAGAAGAGCAACAGCTATACTCAGA

AAAGCAACCAGGAGATTGATTCAGCTGATAGTGAGTGGGAGAGACGAACAGTCGATTGCC

GAAGCAATAATTGTGGCCATGGTATTTTCACAAGAGGATTGTATGATAAAAGCAGTTAGA

GGTGACCTGAATTTCGTCAATAGGGCGAATCAGCGATTGAATCCCATGCACCAACTTTTG

AGACATTTTCAGAAGGATGCAAAGGTGCTCTTTCAAAATTGGGGAATTGAATCCATCGAC

AATGTGATGGGAATGATCGGGATATTGCCCGACATGACTCCAAGCACCGAGATGTCAATG

AGAGGAGTGAGAATCAGCAAAATGGGGGTAGATGAGTATTCCAGCGCGGAGAAGATAGTG

GTGAGCATTGACCGTTTTTTGAGAGTTAGGGACCAACGTGGGAATGTACTACTGTCTCCC

GAGGAGATCAGTGAAACACAGGGAACAGAGAAACTGACAATAACTTACTCATCGTCAATG

ATGTGGGAGATTAATGGTCCTGAATCAGTGTTGGTCAATACCTATCAGTGGATCATCAGA

AACTGGGAAACTGTTAAAATTCAGTGGTCCCAGAATCCTACAATGCTGTACAATAAAATG

GAATTTGAGCCATTTCAGTCTTTAGTTCCAAAGGCCGTTAGAGGCCAATACAGTGGGTTT

GTGAGAACTCTGTTCCAACAAATGAGGGATGTGCTTGGGACATTTGATACCGCTCAGATA

ATAAAACTTCTTCCCTTCGCAGCCGCTCCACCAAAGCAAAGTAGAACGCAGTTCTCCTCA

TTGACTATAAATGTGAGGGGATCAGGAATGAGAATACTTGTAAGGGGCAATTCTCCAGTA

TTCAACTACAACAAGACCACTAAAAGACTCACAGTTCTCGGAAAGGATGCTGGCCCTTTA

ACTGAAGACCCAGATGAAGGCACAGCTGGAGTTGAGTCCGCAGTTCTGAGAGGATTCCTC

ATTCTGGGCAAAGAAGACAGGAGATATGGACCAGCATTAAGCATAAATGAACTGAGCAAC

CTTGCGAAAGGAGAGAAGGCTAATGTGCTAATTGGGCAAGGAGACGTGGTGTTGGTAATG

AAACGGAAACGGAACTCTAGCATACTTACTGACAGCCAGACAGCGACCAAAAGAATTCGG

ATGGCCATCAATTAGTGTCGAATAGTTTAAAAA

Second segment (WSN_flu2)

(SEQ ID NO: 8)

ATTTGAATGGATGTCAATCCGACTTTACTTTTCTTAAAAGTGCCAGCACAAAATGCTATA

AGCACAACTTTCCCTTATACTGGAGACCCTCCTTACAGCCATGGGACAGGAACAGGATAC

ACCATGGATACTGTCAACAGGACACATCAGTACTCAGAAAGGGGAAGATGGACAACAAAC

ACCGAAACTGGAGCACCGCAACTCAACCCGATTGATGGGCCACTGCCAGAAGACAATGAA

CCAAGTGGTTATGCCCAAACAGATTGTGTATTGGAAGCAATGGCCTTCCTTGAGGAATCC

CATCCTGGTATCTTTGAGACCTCGTGTCTTGAAACGATGGAGGTTGTTCAGCAAACACGA

GTGGACAAGCTGACACAAGGCCGACAGACCTATGACTGGACTCTAAATAGGAACCAGCCT

GCTGCAACAGCATTGGCCAACACAATAGAAGTGTTCAGATCAAATGGCCTCACGGCCAAT

GAATCTGGAAGGCTCATAGACTTCCTTAAGGATGTAATGGAGTCAATGAACAAAGAAGAA

ATGGAGATCACAACTCATTTTCAGAGAAAAAGACGAGTGAGAGACAATATGACTAAGAAA

ATGGTGACACAGAGAACAATAGGTAAAAGGAAGCAGAGATTGAACAAAAGGAGTTATCTA

-continued

```
ATTAGGGCATTAACCCTGAACACAATGACCAAAGATGCTGAGAGAGGGAAGCTAAAACGG

AGAGCAATTGCAACCCCAGGGATGCAAATAAGGGGGTTTGTATACTTTGTTGAGACACTA

GCAAGGAGTATATGTGAGAAACTTGAACAATCAGGATTGCCAGTTGGAGGCAATGAGAAG

AAAGCAAAGTTGGCAAATGTTGTAAGGAAGATGATGACCAATTCTCAGGACACTGAAATT

TCTTTCACCATCACTGGAGATAACACCAAATGGAACGAAAATCAGAACCCTCGGATGTTT

TTGGCCATGATCACATATATAACCAGAAATCAGCCCGAATGGTTCAGAAATGTTCTAAGT

ATTGCTCCAATAATGTTCTCAAACAAAATGGCGAGACTGGGAAAGGGGTACATGTTTGAG

AGCAAGAGTATGAAAATTAGAACTCAAATACCTGCAGAAATGCTAGCAAGCATCGATTTG

AAATACTTCAATGATTCAACTAGAAAGAAGATTGAAAAAATCCGGCCGCTCTTAATAGAT

GGGACTGCATCATTGAGCCCTGGAATGATGATGGGCATGTTCAATATGTTAAGTACTGTA

TTAGGAGTCTCCATCCTGAATCTTGGACAAAAGAGACACACCAAGACTACTTACTGGTGG

GATGGTCTTCAATCTTCTGATGATTTTGCTCTGATTGTGAATGCACCCAATCATGAAGGG

ATTCAAGCCGGAGTCAACAGGTTTTATCGAACCTGTAAGCTACTTGGAATTAATATGAGC

AAGAAAAAGTCTTACATAAACAGAACAGGTACATTTGAATTCACAAGTTTTTTCTATCGT

TATGGGTTTGTTGCCAATTTCAGCATGGAGCTTCCCAGCTTTGGGGTGTCTGGGATCAAC

GAGTCTGCGGACATGAGTATTGGAGTTACTGTCATCAAAAACAATATGATAAACAATGAT

CTTGGTCCAGCAACCGCTCAAATGGCCCTTCAGCTGTTCATCAAAGATTACAGGTACACG

TACCGGTGCCATAGAGGTGACACACAAATACAAACCCGAAGATCATTTGAAATAAAGAAA

CTGTGGGAGCAAACCCATTCCAAAGCTGGACTGCTGGTCTCCGACGGAGGCCCAAATTTA

TACAACATTAGAAATCTCCACATTCCTGAAGTCTGCTTGAAATGGGAATTAATGGATGAG

GATTACCAGGGGCGTTTATGCAACCCACTGAACCCATTTGTCAACCATAAAGACATTGAA

TCAGTGAACAATGCAGTGATAATGCCAGCACATGGTCCAGCCAAAAACATGGAGTATGAT

GCTGTTGCAACAACACACTCCTGGATCCCCAAAAGAAATCGATCCATCTTGAATACAAGC

CAAAGAGGAATACTTGAAGATGAACAAATGTACCAAAAGTGCTGCAACTTATTTGAAAAA

TTCTTCCCCAGCAGTTCATACAGAAGACCAGTCGGGATATCCAGTATGGTGGAGGCTATG

GTTTCCAGAGCCCGAATTGATGCACGAATTGATTTCGAATCTGGAAGGATAAAGAAAGAG

GAGTTCACTGAGATCATGAAGATCTGTTCCACCATTGAAGAGCTCAGACGGCAAAAATAG

TGAATTTAGCTTGTCCTTCATGA
```

Third segment (WSN flu3)

(SEQ ID NO: 9)
```
CTGATTCAAAATGGAAGATTTTGTGCGACAATGCTTCAATCCGATGATTGTCGAGCTTGC

GGAAAAGGCAATGAAAGAGTATGGAGAGGACCTGAAAATCGAAACAAACAAATTTGCAGC

AATATGCACTCACTTGGAAGTGTGCTTCATGTATTCAGATTTTCACTTCATCGATGAGCA

AGGCGAGTCAATAGTCGTAGAACTTGGCGATCCAAATGCACTTTTGAAGCACAGATTTGA

AATAATCGAGGGAAGAGATCGCACAATAGCCTGGACAGTAATAAACAGTATTTGCAACAC

TACAGGGGCTGAGAAACCAAAGTTTCTACCAGATTTGTATGATTACAAGGAAGAATAGATT

CATCGAAATTGGAGTAACAAGGAGAGAAGTTCACATATACTATCTGGAAAAGGCCAATAA

AATTAAATCTGAGAAGACACACATCCACATTTTCTCATTCACTGGGGAGGAAATGGCCAC

AAAGGCCGACTACACTCTCGATGAAGAAAGCAGGGCTAGGATCAAAACCAGGCTATTCAC

CATAAGACAAGAAATGGCTAGCAGAGGCCTCTGGGATTCCTTTCGTCAGTCCGAGAGAGG

CGAAGAGACAATTGAAGAAAGATTTGAAATCACAGGAACAATGCGCAAGCTTGCCGACCA

AAGTCTCCCGCCAAACTTCTCCAGCCTTGAAAAATTTAGAGCCTATGTGGATGGATTCGA
```

-continued

ACCGAACGGCTACATTGAGGGCAAGCTTTCTCAAATGTCCAAAGAAGTAAATGCTAGAAT

TGAACCTTTTTTGAAATCAACACCACGACCACTTAGACTTCCGGATGGGCCTCCCTGTTC

TCAGCGGTCCAAATTCCTGCTGATGGATGCCTTAAAATTAAGCATTGAGGACCCAAGTCA

TGAGGGAGAGGGGATACCGCTATATGATGCAATCAAATGCATGAGAACATTCTTTGGATG

GAAGGAACCCAATGTTGTTAAACCACACGAAAAGGGAATAAATCCAAATTATCTTCTGTC

ATGGAAGCAAGTACTGGCAGAACTGCAGGACATTGAGAATGAGGAGAAAATTCCAAGGAC

TAAAAATATGAAGAAAACGAGTCAGTTAAAGTGGGCACTTGGTGAGAACATGGCACCAGA

AAAGGTAGACTTTGACGATTGTAAAGATGTAGGCGATTTGAAGCAATATGATAGTGATGA

ACCAGAATTGAGGTCGCTTGCAAGTTGGATTCAGAATGAGTTCAACAAGGCATGTGAACT

GACCGATTCAAGCTGGATAGAGCTCGATGAGATTGGAGAAGATGCGGCTCCAATTGAACA

CATTGCAAGCATGAGAAGGAATTATTTCACAGCAGAGGTGTCTCATTGCAGAGCCACAGA

ATACATAATGAAGGGGGTGTACATCAATACTGCCTTGCTTAATGCATCCTGTGCAGCAAT

GGATGATTTCCAATTAATTCCAATGATAAGCAAGTGTAGAACTAAGGAGGGAAGGCGAAA

GACCAATTTGTACGGTTTCATCATAAAAGGAAGATCCCACTTAAGGAATGACACCGATGT

GGTAAACTTTGTGAGCATGGAGTTTTCCCTCACTGACCCAAGACTTGAACCACACAAATG

GGAGAAGTACTGTGTTCTTGAGGTAGGAGATATGCTTCTAAGAAGTGCCATAGGCCATGT

GTCAAGGCCTATGTTCTTGTATGTGAGGACAAATGGAACCTCAAAAATTAAAATGAAATG

GGGGATGGAAATGAGGCGTTGCCTCCTTCAGTCACTTCAACAAATCGAGAGTATGATTGA

AGCTGAGTCCTCTGTCAAGGAGAAAGACATGACCAAAGAGTTCTTTGAAAACAAATCAGA

AACATGGCCCGTTGGAGAGTCCCCCAAAGGAGTGGAGGAAGGTTCCATTGGGAAGGTCTG

CAGAACTTTATTGGCAAAGTCGGTATTCAACAGCTTGTATGCATCTCCACAACTAGAAGG

ATTTTCAGCTGAATCAAGAAAACTGCTTCTTATCGTTCAGGCTCTTAGGGACAACCTGGA

ACCTGGGACCTTTGATCTTGGGGGCTATATGAAGCAATTGAGGAGTGCCTGATTAATGA

TCCCTGGGTTTTGCTTAATGCTTCTTGGTTCAACTCCTTCCTCACACATGCATTGAGATA

GTTGTGGCAATGCTACTATTTGCTATCCATACTGTCCAAAAA

Fourth segment (WSN flu4)

(SEQ ID NO: 10)

CCAAAATGAAGGCAAAACTACTGGTCCTGTTATATGCATTTGTAGCTACAGATGCAGACA

CAATATGTATAGGCTACCATGCGAACAACTCAACCGACACTGTTGACACAATACTCGAGA

AGAATGTGGCAGTGACACATTCTGTTAACCTGCTCGAAGACAGCCACAACGGGAAACTAT

GTAAATTAAAAGGAATAGCCCCACTACAATTGGGGAAATGTAACATCACCGGATGGCTCT

TGGGAAATCCAGAATGCGACTCACTGCTTCCAGCGAGATCATGGTCCTACATTGTAGAAA

CACCAAACTCTGAGAATGGAGCATGTTATCCAGGAGATCTCATCGACTATGAGGAACTGA

GGGAGCAATTGAGCTCAGTATCATCATTAGAAAGATTCGAAATATTTCCCAAGGAAAGTT

CATGGCCCAACCACACATTCAACGGAGTAACAGTATCATGCTCCCATAGGGGAAAAAGCA

GTTTTTACAGAAATTTGCTATGGCTGACGAAGAAGGGGGATTCATACCCAAAGCTGACCA

ATTCCTATGTGAACAATAAAGGGAAAGAAGTCCTTGTACTATGGGGTGTTCATCACCCGT

CTAGCAGTGATGAGCAACAGAGTCTCTATAGTAATGGAAATGCTTATGTCTCTGTAGCGT

CTTCAAATTATAACAGGAGATTCACCCCGGAAATAGCTGCAAGGCCCAAAGTAAGAGATC

AACATGGGAGGATGAACTATTACTGGACCTTGCTAGAACCCGGAGACACAATAATATTTG

AGGCAACTGGTAATCTAATAGCACCATGGTATGCTTTCGCACTGAGTAGAGGGTTTGAGT

-continued

CCGGCATCATCACCTCAAACGCGTCAATGCATGAGTGTAACACGAAGTGTCAAACACCCC

AGGGAGCTATAAACAGCAATCTCCCTTTCCAGAATATACACCCAGTCACAATAGGAGAGT

GCCCAAAATATGTCAGGAGTACCAAATTGAGGATGGTTACAGGACTAAGAAACATCCCAT

CCATTCAATACAGAGGTCTATTTGGAGCCATTGCTGGTTTTATTGAGGGGGGATGGACTG

GAATGATAGATGGATGGTATGGTTATCATCATCAGAATGAACAGGGATCAGGCTATGCAG

CGGATCAAAAAAGCACACAAAATGCCATTAACGGGATTACAAACAAGGTGAACTCTGTTA

TCGAGAAAATGAACACTCAATTCACAGCTGTGGGTAAAGAATTCAACAACTTAGAAAAAA

GGATGGAAAATTTAAATAAAAAAGTTGATGATGGGTTTCTGGACATTTGGACATATAATG

CAGAATTGTTAGTTCTACTGGAAAATGAAAGGACTTTGGATTTCCATGACTTAAATGTGA

AGAATCTGTACGAGAAAGTAAAAAGCCAATTAAAGAATAATGCCAAAGAAATCGGAAATG

GGTGTTTTGAGTTCTACCACAAGTGTGACAATGAATGCATGGAAAGTGTAAGAAATGGGA

CTTATGATTATCCAAAATATTCAGAAGAATCAAAGTTGAACAGGGAAAAGATAGATGGAG

TGAAATTGGAATCAATGGGGGTGTATCAGATTCTGGCGATCTACTCAACTGTCGCCAGTT

CACTGGTGCTTTTGGTCTCCCTGGGGGCAATCAGTTTCTGGATGTGTTCTAATGGGTCTT

TGCAGTGCAGAATATGCATCTGAGATTAGGATTTCAGAAATATAA

Fifth segment (WSN flu5)

(SEQ ID NO: 11)

TAGATAATCACTCACAGAGTGACATCGAAATCATGGCGACCAAAGGCACCAAACGATCTT

ACGAACAGATGGAGACTGATGGAGAACGCCAGAATGCCACTGAAATCAGAGCATCTGTCG

GAAAAATGATTGATGGAATTGGACGATTCTACATCCAAATGTGCACCGAACTTAAACTCA

GTGATTATGAGGGACGGCTGATTCAGAACAGCTTAACAATAGAGAGAATGGTGCTCTCTG

CTTTTGACGAGAGGAGGAATAAATATCTAGAAGAACATCCCAGTGCGGGGAAAGATCCTA

AGAAAACTGGAGGACCTATATACAGGAGAGTAGATGGAAAGTGGAGGAGAGAACTCATCC

TTTATGACAAAGAAGAAATAAGACGAATCTGGCGCCAAGCTAATAATGGTGACGATGCAA

CGGCTGGTCTGACTCACATGATGATCTGGCACTCCAATTTGAATGATGCAACTTACCAGA

GGACAAGAGCTCTTGTTCGCACAGGAATGGATCCCAGGATGTGCTCACTGATGCAGGGTT

CAACCCTCCCTAGGAGGTCTGGGGCCGCAGGTGCTGCAGTCAAAGGAGTTGGAACAATGG

TGATGGAATTGATCAGAATGATCAAACGTGGGATCAATGATCGGAACTTCTGGAGGGGTG

AGAATGGACGGAGAACAAGGATTGCTTATGAAAGAATGTGCAACATTCTCAAAGGGAAAT

TTCAAACAGCTGCACAAAGAACAATGGTGGATCAAGTGAGAGAGAGCCGGAATCCAGGAA

ATGCTGAGTTCGAAGATCTCATCTTTTTAGCACGGTCTGCACTCATATTGAGAGGGTCAG

TTGCTCACAAGTCCTGCCTGCCTGCCTGTGTGTATGGATCTGCCGTAGCCAGTGGATACG

ACTTTGAAAGAGAGGGATACTCTCTAGTCGGAATAGACCCTTTCAGACTGCTTCAAAACA

GCCAAGTATACAGCCTAATCAGACCAAATGAGAATCCAGCACACAAGAGTCAACTGGTGT

GGATGGCATGCCATTCTGCTGCATTTGAAGATCTAAGAGTATCAAGCTTCATCAGAGGGA

CGAAAGTGGTCCCAAGAGGGAAGCTTTCCACTAGAGGAGTTCAAATTGCTTCCAATGAAA

ACATGGAGACTATGGAATCAAGTACCCTTGAACTGAGAAGCAGATACTGGGCCATAAGGA

CCAGAAGTGGAGGGAACACCAATCAACAGAGGGCTTCCTCGGGCCAAATCAGCATACAAC

CTACGTTCTCAGTACAGAGAAATCTCCCTTTTGACAGACCAACCATTATGGCAGCATTCA

CTGGGAATACAGAGGGGAGAACATCTGACATGAGAACCGAAATCATAAGGCTGATGGAAA

-continued

```
GTGCAAGACCAGAAGATGTGTCTTTCCAGGGGCGGGGAGTCTTCGAGCTCTCGGACGAAA

AGGCAACGAGCCCGATCGTGCCCTCCTTTGACATGAGTAATGAAGGATCTTATTTCTTCG

GAGACAATGCAGAGGAGTACGACAATTAAAGAAAAAT
```

Sixth segment (WSN flu6)
(SEQ ID NO: 12)

GAGTTTAAATGAATCCAAACCAGAAAATAATAACCATTGGGTCAATCTGTATGGTAGTCG

GAATAATTAGCCTAATATTGCAAATAGGAAATATAATCTCAATATGGATTAGCCATTCAA

TTCAAACCGGAAATCAAAACCATACTGGAATATGCAACCAAGGCAGCATTACCTATAAAG

TTGTTGCTGGGCAGGACTCAACTTCAGTGATATTAACCGGCAATTCATCTCTTTGTCCCA

TCCGTGGGTGGGCTATACACAGCAAAGACAATGGCATAAGAATTGGTTCCAAAGGAGACG

TTTTTGTCATAAGAGAGCCTTTTATTTCATGTTCTCACTTGGAATGCAGGACCTTTTTTC

TGACTCAAGGCGCCTTACTGAATGACAAGCATTCAAGGGGGACCTTTAAGGACAGAAGCC

CTTATAGGGCCTTAATGAGCTGCCCTGTCGGTGAAGCTCCGTCCCCGTACAATTCAAGGT

TTGAATCGGTTGCTTGGTCAGCAAGTGCATGTCATGATGGAATGGGCTGGCTAACAATCG

GAATTTCTGGTCCAGATGATGGAGCAGTGGCTGTATTAAAATACAACCGCATAATAACTG

AAACCATAAAAAGTTGGAGGAAGAATATATTGAGAACACAAGAGTCTGAATGTACCTGTG

TAAATGGTTCATGTTTTACCATAATGACCGATGGCCCAAGTGATGGGCTGGCCTCGTACA

AAATTTTCAAGATCGAGAAGGGGAAGGTTACTAAATCGATAGAGTTGAATGCACCTAATT

CTCACTACGAGGAATGTTCCTGTTACCCTGATACCGGCAAAGTGATGTGTGTGTGCAGAG

ACAATTGGCACGGTTCGAACCGACCATGGGTGTCCTTCGACCAAAACCTAGATTATAAAA

TAGGATACATCTGCAGTGGGGTTTTCGGTGACAACCCGCGTCCCAAAGATGGAACAGGCA

GCTGTGGCCCAGTGTCTGCTGATGGAGCAAACGGAGTAAAGGGATTTTCATATAAGTATG

GCAATGGTGTTTGGATAGGAAGGACTAAAAGTGACAGTTCCAGACATGGGTTTGAGATGA

TTTGGGATCCTAATGGATGGACAGAGACTGATAGTAGGTTCTCTATGAGACAAGATGTTG

TGGCAATAACTAATCGGTCAGGGTACAGCGGAAGTTTCGTTCAACATCCTGAGCTAACAG

GGCTAGACTGTATGAGGCCTTGCTTCTGGGTTGAATTAATCAGGGGGCTACCTGAGGAGG

ACGCAATCTGGACTAGTGGGAGCATCATTTCTTTTTGTGGTGTGAATAGTGATACTGTAG

ATTGGTCTTGGCCAGACGGTGCTGAGTTGCCGTTCACCATTGACAAGTAG

Seventh segment (WSN flu7)

(SEQ ID NO: 13)

GTAGATATTGAAAGATGAGTCTTCTAACCGAGGTCGAAACGTACGTTCTCTCTATCGTCC

CGTCAGGCCCCCTCAAAGCCGAGATCGCACAGAGACTTGAAGATGTCTTTGCAGGGAAGA

ACACCGATCTTGAGGTTCTCATGGAATGGCTAAAGACAAGACCAATCCTGTCACCTCTGA

CTAAGGGGATTTTAGGATTTGTGTTCACGCTCACCGTGCCCAGTGAGCGGGGACTGCAGC

GTAGACGCTTTGTCCAAAATGCTCTTAATGGGAACGGAGATCCAAATAACATGGACAAAG

CAGTTAAACTGTATAGGAAGCTTAAGAGGGAGATAACATTCCATGGGGCCAAAGAAATAG

CACTCAGTTATTCTGCTGGTGCACTTGCCTGTTGTATGGGCCTCATATACAACAGGATGG

GGGCTGTGACCACTGAAGTGGCATTTGGCCTGGTATGCGCAACCTGTGAACAGATTGCTG

ACTCCCAGCATCGGTCTCATAGGCAAATGGTGACAACAACCAATCCACTAATCAGACATG

AGAACAGAATGGTTCTAGCCAGCACTACAGCTAAGGCTATGGAGCAAATGGCTGGATCGA

GTGAGCAAGCAGCAGAGGCCATGGATATTGCTAGTCAGGCCAGGCAAATGGTGCAGGCGA

TGAGAACCGTTGGGACTCATCCTAGCTCCAGTGCTGGTCTAAAAGATGATCTTCTTGAAA

ATTTACAGGCCTATCAGAAACGAATGGGGGTGCAGATGCAACGATTCAAGTGATCCTCTC

-continued

```
GTCATTGCAGCAAATATCATTGGAATCTTGCACTTGATATTGTGGATTCTTGATCGTCTT

TTTTTCAAATGCATTTATCGTCGCTTTAAATACGGTTTGAAAAGAGGGCCTTCTACCGAA

GGAGTGCCAGAGTCTATGAGGGAAGAATATCGAAAGGAACAGCAGAATGCTGTGGATGTT

GACGATGGTCATTTTGTCAACATAGAGCTGGAGTAA
```

Eighth segment (WSN flu8)
(SEQ ID NO: 14)
```
TGACAAAGACATAATGGATCCAAACACTGTGTCAAGCTTTCAGGTAGATTGCTTTCTTTG

GCATGTCCGCAAAAGAGTTGCAGACCAAGAACTAGGTGATGCCCCATTCCTTGATCGGCT

TCGCCGAGATCAGAAGTCCCTAAGAGGAAGAGGCAGCACTCTTGGTCTGGACATCGAAAC

AGCCACCCGTGCTGGAAAGCAAATAGTGGAGCGGATTCTGAAGGAAGAATCTGATGAGGC

ACTCAAAATGACCATGGCCTCTGTACCTGCATCGCGCTACCTAACTGACATGACTCTTGA

GGAAATGTCAAGGCACTGGTTCATGCTCATGCCCAAGCAGAAAGTGGCAGGCCCTCTTTG

TATCAGAATGGACCAGGCGATCATGGATAAGAACATCATACTGAAAGCGAACTTCAGTGT

GATTTTTGACCGGCTGGAGACTCTAATATTACTAAGGGCCTTCACCGAAGAGGGACAAT

TGTTGGCGAAATTTCACCACTGCCCTCTCTTCCAGGACATACTGATGAGGATGTCAAAAA

TGCAGTTGGGGTCCTCATCGGAGGACTTGAATGGAATAATAACACAGTTCGAGTCTCTGA

AACTCTACAGAGATTCGCTTGGAGAAGCAGTAATGAGAATGGGAGACCTCCACTCACTCC

AAAACAGAAACGGAAAATGGCGGGAACAATTAGGTCAGAAGTTTGAAGAAATAAGGTGGT

TGATTGAAGAAGTGAGACACAGACTGAAGATAACAGAGAATAGTTTTGAGCAAATAACAT

TTATGCAAGCCTTACAACTATTGCTTGAAGTGGAGCAAGAGATAAGAACTTTCTCGTTTC

AGCTTATTTAATAA
``` b. PB1 (polymerase basic protein 1)
(SEQ ID NO: 2)
```
MDVNPTLLFLKVPAQNAISTTFPYTGDPPYSHGTGTGYTMDTVNRTHQYSER

GRWTTNTETGAPQLNPIDGPLPEDNEPSGYAQTDCVLEAMAFLEESHPGIFET

SCLETMEVVQQTRVDKLTQGRQTYDWTLNRNQPAATALANTIEVERSNGLT

ANESGRLIDELKDVMESMNKEEMEITTHFQRKRRVRDNMTKKMVTQRTIGK

RKQRLNKRSYLIRALTLNTMTKDAERGKLKRRAIATPGMQIRGEVYFVETLA

RSICEKLEQSGLPVGGNEKKAKLANVVRKMMTNSQDTEISFTITGDNTKWNE

NQNPRMFLAMITYITRNQPEWERNVLSIAPIMFSNKMARLGKGYMFESKSMK

LRTQIPAEMLASIDLKYENDSTRKKIEKIRPLLIDGTASLSPGMMMGMFNMLS

TVLGVSILNLGQKRHTKTTYWWDGLQSSDDFALIVNAPNHEGIQAGVNRFYR

TCKLLGINMSKKKSYINRTGTFEFTSFFYRYGFVANFSMELPSFGVSGINESAD

MSIGVTVIKNNMINNDLGPATAQMALQLFIKDYRYTYRCHRGDTQIQTRRSF

EIKKLWEQTHSKAGLLVSDGGPNLYNIRNLHIPEVCLKWELMDEDYQGRLCN

PLNPFVNHKDIESVNNAVIMPAHGPAKNMEYDAVATTHSWIPKRNRSILNTS

QRGILEDEQMYQKCCNLFEKFFPSSSYRRPVGISSMVEAMVSRARIDARIDFES

GRIKKEEFTEIMKICSTIEELRRQK
``` c. PB2 (polymerase basic protein 2)
(SEQ ID NO: 3)
```
MERIKELRNLMSQSRTREILTKTTVDHMAIIKKYTSGRQEKNPALRMKWMM

AMKYPITADKRITEMIPERNEQGQTLWSKMNDAGSDRVMVSPLAVTWWNR

NGPVTSTVHYPKIYKTYFEKVERLKHGTFGPVHFRNQVKIRRRVDINPGHADL
```

```
-continued
SAKEAQDVIMEVVFPNEVGARILTSESQLTTTKEKKEELQGCKISPLMVAYML

ERELVRKTRFLPVAGGTSSVYIEVLHLTQGTCWEQMYTPGGEARNDDVDQSL

IIAARNIVRRATVSADPLASLLEMCHSTQIGGVRMVNILRQNPTEEQAVDICK

AAMGLRISSSFSFGGFTFKRTSGSSVKREEEVLTGNLQTLKIRVHEGYEEFTM

VGRRATAILRKATRRLIQLIVSGRDEQSIAEAIIVAMVFSQEDCMIKAVRGDLN

FVNRANQRLNPMHQLLRHFQKDAKVLFQNWGIESIDNVMGMIGILPDMTPST

EMSMRGVRISKMGVDEYSSAEKIVVSIDRFLRVRDQRGNVLLSPEEVSETQGT

EKLTITYSSSMMWEINGPESVLVNTYQWIIRNWETVKIQWSQNPTMLYNKME

FEPFQSLVPKAVRGQYSGFVRTLFQQMRDVLGTFDTAQIIKLLPFAAAPPKQS

GMQFSSLTINVRGSGMRILVRGNSPVFNYNKTTKRLTVLGKDAGPLTEDPDE

GTAGVESAVLRGFLILGKEDRRYGPALSINELSNLAKGEKANVLIGQGDVVL

VMKRKRNSSILTDSQTATKRIRMAIN d. PA (polymerase acidic protein)
                                            (SEQ ID NO: 4)
MEDFVRQCFNPMIVELAEKAMKEYGEDLKIETNKFAAICTHLQLEGFSAESR

KLLLIVQALRDNLEPGTFDLGGLYEAIEECLINDPWVLLNASWFNSFLTHALR e. M1 (Matrix protein 1)
                                            (SEQ ID NO: 5)
MSLLTEVETYVLSIVPSGPLKAEIAQRLEDVFAGKNTDLEVLMEWLKTRPILS

PLTKGILGFVFTLTVPSERGLQRRRFVQNALNGNGDPNNMDKAVKLYRKLKR

EITFHGAKEIALSYSAGALASCMGLIYNRMGAVTTEVAFGLVCATCEQIADSQ

HRSHRQMVTTTNPLIRHENRMVLASTTAKAMEQMAGSSEQAAEAMDIASQA

RQMVQAMRTIGTHPSSSAGLKDDLLENLQAYQKRMGVQMQRFK f. M2 Matrix protein 2
                                            (SEQ ID NO: 6)
MSLLTEVETPIRNEWGCRCNDSSDPLVIAANIIEILHLILWILDRLFFKCIYRRFK

YGLKRGPSTEGVPESMREEYRKEQQNAVDVDDGHFVNIELE g. NS1 Non-structural protein 1
                                            (SEQ ID NO: 7)
MDPNTVSSFQVDCFLWHVRKRVADQELGDAPFLDRLRRDQKSLRGRGSTLG

LDIETATRAGKQIVERILKEESDEALKMTMASVPASRYLTDMTLEEMSRHWF

MLMPKQKVAGPLCIRMDQAIMDKNIILKANFSVIFDRLETLILLRAFTEEGTIV

GEISPLP SLPGHTDEDVKNAVGVLIGGLEWNNNTVRVSETLQRFAWRSSNEN

GRPPLTPKQKRKMAGTIRSEV
```

REFERENCES

Note: This application references a number of different publications as indicated throughout the specification by reference numbers enclosed in brackets, e.g., (x). A list of these different publications ordered according to these reference numbers can be found below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

1. M. T. Osterholm, N. S. Kelley, A. Sommer, E. A. Belongia Lancet Infect. Dis. 12, 36-44 (2012).
2. A. C. Tricco et al., BMC Med. 11, 153 (2013).
3. M. Darvishian, M. J. Bijlsma, E. Hak, E. R. van den Heuvel, Lancet Infect. Dis. 14, 1228-1239 (2014).
4. A. Garcia-Sastre, Virus Res. 162, 12-18 (2011).
5. J. M. González-Navajas, J. Lee, M. David, E. Raz, Nat. Rev. Immunol. 12, 125-135 (2012).
6. A. Iwasaki, P. S. Pillai, Nat. Rev. Immunol. 14, 315-328 (2014).
7. J. W. Schoggins et al., Nature 472, 481-485 (2011).
8. J. P. Huber, J. D. Farrar, Immunology 132, 466-474 (2011).
9. A. Le Bon et al., Immunity 14, 461-470 (2001).
10. R. M. Welsh, K. Bahl, H. D. Marshall, S. L. Urban, PLOS Pathog. 8, e1002352 (2012).
11. A. Le Bon, D. F. Tough, Curr. Opin. Immunol. 14, 432-436 (2002).

12. J. Crouse, U. Kalinke, A. Oxenius, Nat. Rev. Immunol. 15, 231-242 (2015).
13. F. Krammer, P. Palese, Nat. Rev. Drug Discov. 14, 167-182 (2015).
14. J. Talon et al., Proc. Natl. Acad. Sci. U.S.A. 97, 4309-4314 (2000).
15. C. Mössier et al., Vaccine 31, 6194-6200 (2013).
16. K. M. Graef et al., J. Virol. 84, 8433-8445 (2010).
17. M. Perez-Cidoncha et al Virol. 88, 4632-4646 (2014).
18. N. C. Wu et al., Sci. Rep. 4, 4942 (2014).
19. N. C. Wu et al., J. Virol. 88, 10157-10164 (2014).
20. E. Hoffmann, G. Neumann, Y. Kawaoka, G. Hobom, R. G. Webster, Proc. Natl. Acad. Sci. U.S.A. 97, 6108-6113 (2000).
21. Y. Du et al., MBio 7, e01801-16 (2016).
22. N. C. Wu et al., PLOS Genet. 11, e1005310 (2015).
23. N. C. Wu et al., BMC Genomics 17, 46 (2016).
24. S. F. Elena, P. Carrasco, J.-A. Darós, R. Sanjuan, EMBO Rep. 7, 168-173 (2006).
25. E. Visher, S. E. Whitefield, J. T. McCrone, W. Fitzsimmons, A. S. Lauring, PLOS Pathog. 12, e1005856 (2016).
26. B. G. Hale, R. A. Albrecht, A. Garcia-Sastre, Future Microbiol. 5, 23-41 (2010).
27. B. G. Hale, R. E. Randall, J. Ortin, D. Jackson, J. Gen. Virol. 89, 2359-2376 (2008).
28. H. F. Maassab, M. L. Bryant, Rev. Med. Virol. 9, 237-244 (1999).
29. H. Jin, H. Zhou, B. Lu, G. Kemble, J. Virol. 78, 995-998 (2004).
30. M. J. Memoli et al., MBio 7, e00417-e16 (2016).
31. D. M. Carragher, D. A. Kaminski, A. Moquin, L. Hartson, T. D. Randall, J. Immunol. 181, 4168-4176 (2008).
32. M. B. Doud, S. E. Hensley, J. D. Bloom, PLOS Pathog. 13, e1006271 (2017).
33. S. Mueller et al., Nat. Biotechnol. 28, 723-726 (2010).
34. L. Si et al., Science 354, 1170-1173 (2016).
35. C.-Y. Wu et al., Proc. Natl. Acad. Sci. U.S.A. 114, 280-285 (2017).
36. L. Wang et al., Cell Host Microbe 21, 334-343 (2017).
37. J. Steel et al., J. Virol. 83, 1742-1753 (2009).
38. A. Pflug, D. Guilligay, S. Reich, S. Cusack, Nature 516, 355-360 (2014).
39. S. Reich et al., Nature 516, 361-366 (2014).
40. S. J. Gamblin et al., Science 303, 1838-1842 (2004)
41. PB1 sequence found at website having the address www.fludb.org/brc/proteinSequence.spg?ncbiProteinId=ABF47963&decorator=influenza
42. PB2 sequence found at web site having the address www.fludb.org/brc/proteinSequence.spg?ncbiProteinId=ACF54608&decorator=influenza
43. PA sequence found at web site having the address www.fludb.org/brc/proteinSequence.spg?ncbiProteinId=BAA01431&decorator=influenza
44. M1 sequence found at website having the address www.fludb.org/brc/proteinSequence.spg?ncbiProteinId=AAA91325&decorator=influenza
45. M2 sequence found at website having the address www.fludb.org/brc/proteinSequence.spg?ncbiProteinId=AAA91324&decorator=influenza
46. NS1 sequence found at web site having the address www.fludb.org/brc/proteinSequence.spg?ncbiProteinId=ACF54603&decorator=influenza.
47. Genome-wide identification of interferon-sensitive mutations enables influenza vaccine design by Yushen Du[1] et. al., *Science* 19 Jan. 2018: Vol. 359, Issue 6373, pp. 290-296 DOI: 10.1126/science.aan8806, including supplementary information.
48. H. Jin et al., Multiple amino acid residues confer temperature sensitivity to human influenza virus vaccine strains (flumist) derived from cold-adapted a/ann arbor/6/60. *Virology.* 306, 18-24 (2003).
49. Vincent A L[1], Ma W, Lager K M, Richt J A, Janke B H, Sandbulte M R, Gauger P C, Loving C L, Webby R J, Garcia-Sastre A. Live attenuated influenza vaccine provides superior protection from heterologous infection in pigs with maternal antibodies without inducing vaccine-associated enhanced respiratory disease. J Virol. 2012 October; 86(19):10597-605. doi: 10.1128/JVI.01439-12. Epub 2012 Jul. 18.
50. U.S. Pat. No. 9,387,240.
51. complete sequence for influenza A wild type strain A/WSN/1933 can be found at www.fludb.org/brc/fluStrainDetails.spg?strainName=A/WSN/1933(H1N1)&decorator=influenza.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

The invention claimed is:

1. A composition of matter, comprising:
   a genetically engineered influenza A virus genome comprises a combination of nucleotide mutations at more than two amino acid positions selected from:
   at least one amino acid substitution in SEQ ID NO: 3 at amino acid position N9, Q75 or T76; and/or
   at least one amino acid substitution in SEQ ID NO: 5 at amino acid position N36, R72 or S225.

2. The composition of matter of claim 1, wherein the genetically engineered influenza A virus genome further comprises at least one amino acid substitution in SEQ ID NO: 7 at amino acid position R38 or K41.

3. The composition of matter of claim 1, wherein each of the nucleotide mutations are located in different segments of the genome.

4. The composition of claim 1, wherein the combination of nucleotide mutations at more than two amino acid positions comprises at least 4 nucleotide mutations.

5. A vaccine or therapeutic agent comprising the composition of matter of claim 1.

6. The composition of matter of claim 1, wherein the genetically engineered influenza A virus genome comprises the combination of nucleotide mutations at more than two amino acid positions which increase an influenza A virus sensitivity to type I interferon.

7. The composition of claim 6, wherein genetically engineered influenza A genome further comprises mutations in at least one single nucleotide in the influenza A: SEQ ID NO: 4 or SEQ ID NO: 2.

8. The composition of claim 1, wherein the at least one mutation is: found at amino acid position N9, Q75, and T76 in SEQ ID NO: 3, and/or found at amino acid position N36, R72, and S225 in SEQ ID NO: 5.

9. The composition of claim 1, wherein the at least one mutation is:
   selected from at least one of N9D, Q75H, or T76A in SEQ ID NO: 3, and/or selected from at least one of N36Y, R72Q, or S225T in SEQ ID NO: 5.

* * * * *